(12) United States Patent
Cao

(10) Patent No.: US 7,259,236 B2
(45) Date of Patent: Aug. 21, 2007

(54) RBP1L1, A NOVEL RETINOBLASTOMA BINDING PROTEIN-RELATED GENE ENCODING AN ANTIGENIC EPITOPE AND METHODS OF USING THEREOF

(75) Inventor: Jia-ning Cao, Santa Monica, CA (US)

(73) Assignee: Regents of the University of California, Oakland, CA (US)

( * ) Notice: Subject to any disclaimer, the term of this patent is extended or adjusted under 35 U.S.C. 154(b) by 536 days.

(21) Appl. No.: 10/471,934

(22) PCT Filed: Mar. 13, 2002

(86) PCT No.: PCT/US02/07433

§ 371 (c)(1),
(2), (4) Date: Feb. 17, 2004

(87) PCT Pub. No.: WO02/072610

PCT Pub. Date: Sep. 19, 2002

(65) Prior Publication Data

US 2004/0249142 A1 Dec. 9, 2004

Related U.S. Application Data

(60) Provisional application No. 60/275,518, filed on Mar. 14, 2001.

(51) Int. Cl.
*C07K 7/06* (2006.01)
(52) U.S. Cl. .................................... 530/328; 530/300
(58) Field of Classification Search ................ 530/300, 530/328

See application file for complete search history.

(56) References Cited

U.S. PATENT DOCUMENTS 6,399,373 B1 * 6/2002 Bougueleret ................ 435/330

FOREIGN PATENT DOCUMENTS

WO WO 0000607 A1 * 1/2000
WO WO 0073801 A2 * 12/2000

OTHER PUBLICATIONS

Degruijl et al. Nature Medicine 5(10): 1124-1125, Oct. 1999.*
Bodey et al. Anticancer Research 20: 2665-2676, 2000.*
Mellman I. The Scientist 20(1): 47, 2006.*
Benet et al. Pharmacological Basis of Therapeutics, 8th ed., pp. 3-13, and 16-32 enclosed.*
Burgess et al. Journal of Cell Biology 111: 2129-2138, 1990.*
Lazar et al. Molecular and Cellular Biology 8(3): 1247-1252, 1988.*
Ibragimova et al. Biophysical Journal 77: 2191-2198, 1999.*
Fu et al. EMBO Journal 15: 4392-4401, 1996.*
Vallejo et al. Biochimie 82: 1129-1133, 2000.*
Powell et al. Pharmacogenesis 8: 411-421, 1998, abstract only enclosed.*
Jang et al. Clinical and Experimental Metastasis 15: 469-483, 1997, abstract only enclosed.*

* cited by examiner

*Primary Examiner*—Larry R. Helms
*Assistant Examiner*—Brad Duffy
(74) *Attorney, Agent, or Firm*—Suzannah K. Sunby, Esq.; Smith, Gambrell & Russell, LLP

(57) ABSTRACT

Disclosed herein is a novel retinoblastoma binding protein-related gene that encodes an antigenic epitope, IKPSLG-SKK (SEQ ID NO:3), which is differentially expressed in cancers, such as breast, lung, colon, pancreas, and ovarian cancer. Polynucleotides that encode and polypeptides that comprise the antigenic epitope and variants thereof are disclosed. Also, disclosed are methods of using the polynucleotides and polypeptides of the present invention in immunotherapies and immunoassays.

4 Claims, 10 Drawing Sheets

```
RBP1L1  MKALDEPPYLTVGTDVSAKYRGAFCEAKIKTAKRLIVKVKVTFPHDSSTVEVQDDHIKGPLKVGAIVEVKNLDGAYQEAVINKLTDASWYTVVFDDGDEKTLRRSSLCLKGERHFAESETL  120
RBP1    MKAADEPAYLTVGTDVSAKYRGAFCEAKIKTAKRLIVKVKVTFPHDSSTVEVQDDHIKGPLKVGAIVEVKNLDGAYQEAVINKLTDASWYTVVFDDGDERTLRRTSLCLKGERHFAESETL  120

RBP1L1  DQLPLTNPEHFGTPVIGKKTNRGRRS-NHIPEEESSSSSSDEDEDDRKQID--ELLGKVVCVDYISLDKKKALWFPALVVCPDCSDEIAVKKDNILVRSFKDGKFTSVPRKDVHRITSDT  237
RBP1    DQLPLTNPEHFGTPVIAKKTNRGRSSLPVTEDEKEEESEEEDEDKRRLN-DELLGKVVSVVSATER---TEWYPALVISPSCNDDITVKKDQCLVRSFIDSKPYSIARKDIKEVDILN   236

RBP1L1  APRPDAVLKQAFEQALEFHKSRTIPANWKTELKEDSSSSEAEEEE---BEEDDREKEKEEDNSSEEEE-EIEPFPEERENFLQQLYIKFMEDRGTPINKQPVLGYRNLNLFKLFRLVHKLGGF  353
RBP1    LPESELSTKPGLQKASIFLKTRVVPDNWKQDISEILESSSSDDEDGPAEENDEEKEKEKEAKKTEEEVPEEEILDPEERDNFLQQLYKFMEDRGTPINKPPVLGYKDLNLFKLFRLVYHQGGC  356

RBP1L1  DNIESGAVWKQVYQDLGIPVLNSAAGYNVKCAYKKYLYGFEEYCRSANIEFQMALPEK-VVNKQCKECENVKEIKVKEENETEIKEIKMEEERNLIPREE---------------  452
RBP1    DNIDSGAVWKQIYMDLGIPILNSAASYNLKTAYRKVLYGFEEYCRSANIQFRTVHHEPKVKEEKDLEESMEEALKLDQEMPLTEVKSEPEENIDSNSESEREEIELKSPRGRRRIARD  476

RBP1L1  -------------------KPIEDEIERKENIKPSLGSKKNLLESIPTHSDQEKEVNIKKPEDNENLIDDKDDDTTRVDESLNIKVEAEEEKAKSG----------  528
RBP1    VNSIKKEIEEKTEDKLKONDTENKDVDDDYETAEKKENELLLGRKNTPKQKEKKIKKQEDSDKDSDEEEEKSQEREETESKCDSEGEEDEEDMEPCLTG-----  576

RBP1L1  -------------------YDEWIKADKIVRPADKNVPKIKHRRKKIKNKLDKEKDKEYSPKNCKLRRLSKPPFQTNPS  589
RBP1    -------------TKVKVKYGRGKTQKIYEASIKSTEIDDGEVLYLVHYYGWNVSYDEWVKADRIIWPLDKGGPKKKQKKAKNKEDSEKDKRDEERQKSKRGRPPLKSTLSSNM  679

RBP1L1  PEMVSKLDLTDAKNSDTAHIKSIEITSIINGLQASESSAEDSEQEDERGAQDMDNNGKEESKIDHLTNNRNDLISKEEQNSSSLLEENKVHADLVISKPVSKSPERLRKDIEVLSEDTDY  709
RBP1    PYGLSKTANSEGK-SDSCSSDSETEDALRKNLINEELSLKDELEKNENLNDD------KLDEENFKISAHILKENDRTQMPLETLKLEVGENEQIVQLFGNKMEKAEEVKEAEKS  789

RBP1L1  EE-DEVTKKRDVKKDTTDKSSKPQIK-RGKRRYCNTEECLKTGSPGKKEEKAKNKESLCMENSSNSSSDEDEE--TKAKMTPTKKYNGLEEKRKSLRITGFYSGFSEVABKRIKLLNNS  826
RBP1    PKGKGRRSKTKDLSLEIIKISSFGQNE---------AGSEPHIEAHSLELSSLDNKNFSSATEDEIDQCVKEKKLRKLIGQSSPEKKIRIENGMEMTNTVSQERTSDCIGS  893

RBP1L1  DERLQNSRAKDRKDVWSSIQGGWPKKTLKELFSDSDTBAAASPHPAPEEGVAEESLQTVAEEESCSPSVELEKPPVNVDSKPIEEETVEVNDRKAFPSSGSNSVLNTPPTTPSPSS  946
RBP1    B-------GMKNLMFKQHFERENEGMPSLIAES-NQCIQQLTSERFDSPAEETVNLPLKEDEDAMPLIGPETLVCHEVDLDDLDEK-DKTSIEDVAVESSESNSLVSIPPALRP----  998

RBP1L1  VTVTEGSRQQSSVTVSEPLAPNQEEVRSIKSETDSTIEVDSVAGELQDLQSEGNSSPAGFDASVSSSSNQPEPEHPEKACTGQKRVKDAQGGGSSSKKQKRSHKATVNNKKGKGTNS  1066
RBP1    ----VVQHNFSVASPLTLSQDESRSVK-ESDITIEVDSIAEESQEGLCE-RESANGFETNVASGTCSIIVQERESR-EKGQKRPSDGNSLMAKKQKRTPKRTSAAAKNEKNGTG-QS  1106

RBP1L1  SDSEELSAGESITKSQPVKSVSTGMKSHSTKSPARTQSPGKCGKNGDKDPDLKEPSNRLPKVYKWSFQMSDLENWTSAERITILQEKLQEIRKHYLSLKSEVASIDRRRKRLKKKERESA  1186
RBP1    SDSEDLPVLDNSSKCTPVKHLNVSKPQKLARSPARISP---HIKDGEKDKHREKHPNSSPRTYKWSFQLNELDNWNSTERISFLQEKLQEIRKYMSLKSEVATIDRRRKRLKKKDREVS  1223

RBP1L1  ATSSSSPSSSSITAAAMLTLAEPSMSSASQNGMSVECR                                                                                1226
RBP1    HAGASMSSASSDTG-------MSPSSSSPPQNVLAVECR                                                                               1255
```

Figure 3

SEQUENCE LISTING

```
<160> NUMBER OF SEQ ID NOS: 33

<210> SEQ ID NO 1
<211> LENGTH: 5802
<212> TYPE: DNA
<213> ORGANISM: Homo sapiens
<220> FEATURE:
<221> NAME/KEY: CDS
<222> LOCATION: (463)..(4143)

<400> SEQUENCE: 1
cgatgtttgc ccgtcagtcg agtccggagt gaggagctcg gtcgccgaag cggagggaga      60
ctcttgagct tcatcttgcc gccgccacgg ccaccgcctg gacctttgcc cggagggagc     120
tgcagagggt ccatcgccgc cgtcctctgg agggcagcgc gattgggggc ccggacctcc     180
agtccggggg ggattttttcg tcgtccccct cccccaacc agggagcccg agcggccgcc     240
aaacaaaggt accagtcgcc gccgcgggag gaggaggagc cggagcctct gcctcacagc     300
cgctggaccc gccgccttct tccccatctc tccccgggc ctgctggttt tggggggggag     360 aaggagagag gggactctgg acgtgccagg gtcaaatctc gcctccgagg aagtgcaac      420 tgaacctggt gttttaaagg ataccttggt cccaaagtca tc atg aag gcc ctt        474
                                                Met Lys Ala Leu
                                                1 gat gag cct ccc tat ttg aca gtg ggc act gat gtg agt gct aaa tac        522
Asp Glu Pro Pro Tyr Leu Thr Val Gly Thr Asp Val Ser Ala Lys Tyr
5                   10                  15                  20 aga gga gcc ttt tgt gaa gcc aag atc aag aca gca aaa aga ctt gtc        570
Arg Gly Ala Phe Cys Glu Ala Lys Ile Lys Thr Ala Lys Arg Leu Val
                25                  30                  35 aaa gtc aag gtg aca ttt aga cat gat tct tca aca gtg gaa gtt cag        618
Lys Val Lys Val Thr Phe Arg His Asp Ser Ser Thr Val Glu Val Gln
            40                  45                  50 gat gac cac ata aag ggc cca cta aag gta gga gct att gtg gaa gtg        666
Asp Asp His Ile Lys Gly Pro Leu Lys Val Gly Ala Ile Val Glu Val
        55                  60                  65 aag aat ctt gat ggt gca tat cag gaa gct gtt atc aat aaa cta aca        714
Lys Asn Leu Asp Gly Ala Tyr Gln Glu Ala Val Ile Asn Lys Leu Thr
    70                  75                  80 gat gcg agt tgg tac act gta gtt ttt gat gac gga gat gag aag aca        762
Asp Ala Ser Trp Tyr Thr Val Val Phe Asp Asp Gly Asp Glu Lys Thr
85                  90                  95                 100 ctg aga cga tct tca ctg tgc ctg aaa gga gag agg cat ttt gcc gaa        810
Leu Arg Arg Ser Ser Leu Cys Leu Lys Gly Glu Arg His Phe Ala Glu
                105                 110                 115 agt gaa aca tta gac cag ctc cca ctc acc aac cct gag cat ttt ggc        858
Ser Glu Thr Leu Asp Gln Leu Pro Leu Thr Asn Pro Glu His Phe Gly
```

-continued

```
                    120                      125                      130
act cca gtc ata gga aag aaa aca aat aga gga aga aga tct aat cat        906
Thr Pro Val Ile Gly Lys Lys Thr Asn Arg Gly Arg Arg Ser Asn His
        135                      140                      145 ata cca gag gaa gag tct tca tca tcc tcc agt gat gaa gat gag gat        954
Ile Pro Glu Glu Glu Ser Ser Ser Ser Ser Ser Asp Glu Asp Glu Asp
    150                      155                      160 gat agg aaa cag att gat gag cta cta ggc aaa gtt gta tgt gta gat       1002
Asp Arg Lys Gln Ile Asp Glu Leu Leu Gly Lys Val Val Cys Val Asp
165                      170                      175                      180 tac att agt ttg gat aaa aag aaa gca ctg tgg ttt cct gca ttg gtg       1050
Tyr Ile Ser Leu Asp Lys Lys Lys Ala Leu Trp Phe Pro Ala Leu Val
                185                      190                      195 gtt tgt cct gat tgt agt gat gag att gct gta aaa aag gac aat att       1098
Val Cys Pro Asp Cys Ser Asp Glu Ile Ala Val Lys Lys Asp Asn Ile
            200                      205                      210 ctt gtt cga tct ttc aaa gat gga aaa ttt act tca gtt cca aga aaa       1146
Leu Val Arg Ser Phe Lys Asp Gly Lys Phe Thr Ser Val Pro Arg Lys
        215                      220                      225 gat gtc cat gaa att act agt gac act gca cca aag cct gat gct gtt       1194
Asp Val His Glu Ile Thr Ser Asp Thr Ala Pro Lys Pro Asp Ala Val
    230                      235                      240 tta aag caa gcc ttt gaa cag gca ctt gaa ttt cac aaa agt aga act       1242
Leu Lys Gln Ala Phe Glu Gln Ala Leu Glu Phe His Lys Ser Arg Thr
245                      250                      255                      260 att cct gct aac tgg aag act gaa ttg aaa gaa gat agc tct agc agt       1290
Ile Pro Ala Asn Trp Lys Thr Glu Leu Lys Glu Asp Ser Ser Ser Ser
                265                      270                      275 gaa gca gag gaa gaa gag gag gag gaa gat gat gaa aaa gaa aag gag       1338
Glu Ala Glu Glu Glu Glu Glu Glu Asp Asp Glu Lys Glu Lys Glu
            280                      285                      290 gat aat agc agt gaa gaa gaa gaa gaa ata gaa cca ttt cca gaa gaa       1386
Asp Asn Ser Ser Glu Glu Glu Glu Glu Ile Glu Pro Phe Pro Glu Glu
        295                      300                      305 agg gag aac ttt ctt cag caa ttg tac aaa ttt atg gaa gat aga ggt       1434
Arg Glu Asn Phe Leu Gln Gln Leu Tyr Lys Phe Met Glu Asp Arg Gly
    310                      315                      320 aca cct att aac aaa caa cct gta ctt gga tat cga aat ttg aat ctc       1482
Thr Pro Ile Asn Lys Gln Pro Val Leu Gly Tyr Arg Asn Leu Asn Leu
325                      330                      335                      340 ttt aag tta ttc aga ctt gta cac aaa ctt gga gga ttt gat aat att       1530
Phe Lys Leu Phe Arg Leu Val His Lys Leu Gly Gly Phe Asp Asn Ile
                345                      350                      355 gaa agt gga gct gtt tgg aaa caa gtc tac caa gat ctt gga atc cct       1578
Glu Ser Gly Ala Val Trp Lys Gln Val Tyr Gln Asp Leu Gly Ile Pro
            360                      365                      370 gtc tta aat tca gct gca gga tac aat gtt aaa tgt gct tat aaa aaa       1626
Val Leu Asn Ser Ala Ala Gly Tyr Asn Val Lys Cys Ala Tyr Lys Lys
        375                      380                      385 tac tta tat ggt ttt gag gag tac tgt aga tca gcc aac att gaa ttt       1674
Tyr Leu Tyr Gly Phe Glu Glu Tyr Cys Arg Ser Ala Asn Ile Glu Phe
    390                      395                      400 cag atg gca ttg cca gag aaa gtt gtt aac aag caa tgt aag gag tgt       1722
Gln Met Ala Leu Pro Glu Lys Val Val Asn Lys Gln Cys Lys Glu Cys
405                      410                      415                      420 gaa aat gta aaa gaa ata aaa gtt aag gag gaa aat gaa aca gag atc       1770
Glu Asn Val Lys Glu Ile Lys Val Lys Glu Glu Asn Glu Thr Glu Ile
                425                      430                      435 aaa gaa ata aag atg gag gag gag agg aat ata ata cca aga gaa gaa       1818
```

-continued

```
Lys Glu Ile Lys Met Glu Glu Arg Asn Ile Ile Pro Arg Glu
            440                 445             450 aag cct att gag gat gaa att gaa aga aaa gaa aat att aag ccc tct      1866
Lys Pro Ile Glu Asp Glu Ile Glu Arg Lys Glu Asn Ile Lys Pro Ser
        455                 460                 465 ctg gga agt aaa aag aat tta tta gaa tct ata cct aca cat tct gat      1914
Leu Gly Ser Lys Lys Asn Leu Leu Glu Ser Ile Pro Thr His Ser Asp
    470                 475                 480 cag gaa aaa gaa gtt aac att aaa aaa cca gaa gac aat gaa aat ctg      1962
Gln Glu Lys Glu Val Asn Ile Lys Lys Pro Glu Asp Asn Glu Asn Leu
485                 490                 495                 500 gat gac aaa gat gat gac aca act agg gta gat gaa tcc ctc aac ata      2010
Asp Asp Lys Asp Asp Asp Thr Thr Arg Val Asp Glu Ser Leu Asn Ile
                505                 510                 515 aag gta gaa gct gag gaa gaa aaa gca aaa tct gga tac gat gaa tgg      2058
Lys Val Glu Ala Glu Glu Glu Lys Ala Lys Ser Gly Tyr Asp Glu Trp
        520                 525                 530 att aaa gca gat aaa ata gta aga cct gct gat aaa aat gtg cca aag      2106
Ile Lys Ala Asp Lys Ile Val Arg Pro Ala Asp Lys Asn Val Pro Lys
    535                 540                 545 ata aaa cat cgg aag aaa ata aag aat aaa tta gac aaa gaa aaa gac      2154
Ile Lys His Arg Lys Lys Ile Lys Asn Lys Leu Asp Lys Glu Lys Asp
550                 555                 560 aaa gat gaa aaa tac tct cca aaa aac tgt aaa ctt cgg cgc ttg tcc      2202
Lys Asp Glu Lys Tyr Ser Pro Lys Asn Cys Lys Leu Arg Arg Leu Ser
565                 570                 575                 580 aaa cca cca ttt cag aca aat cca tct cct gaa atg gta tcc aaa ctg      2250
Lys Pro Pro Phe Gln Thr Asn Pro Ser Pro Glu Met Val Ser Lys Leu
                585                 590                 595 gat ctc act gat gcc aaa aac tct gat act gct cat att aag tcc ata      2298
Asp Leu Thr Asp Ala Lys Asn Ser Asp Thr Ala His Ile Lys Ser Ile
            600                 605                 610 gaa att act tcg atc ctt aat gga ctt caa gct tct gaa agt tct gct      2346
Glu Ile Thr Ser Ile Leu Asn Gly Leu Gln Ala Ser Glu Ser Ser Ala
        615                 620                 625 gaa gac agt gag cag gaa gat gag aga ggt gct caa gac atg gat aat      2394
Glu Asp Ser Glu Gln Glu Asp Glu Arg Gly Ala Gln Asp Met Asp Asn
    630                 635                 640 aat ggc aaa gaa gaa tct aag att gat cat ttg acc aac aac aga aat      2442
Asn Gly Lys Glu Glu Ser Lys Ile Asp His Leu Thr Asn Asn Arg Asn
645                 650                 655                 660 gat ctt att tca aag gag gaa cag aac agt tca tct ttg cta gaa gaa      2490
Asp Leu Ile Ser Lys Glu Glu Gln Asn Ser Ser Ser Leu Leu Glu Glu
                665                 670                 675 aac aaa gtt cat gca gat ttg gta ata tcc aaa cca gtg tca aaa tct      2538
Asn Lys Val His Ala Asp Leu Val Ile Ser Lys Pro Val Ser Lys Ser
            680                 685                 690 cca gaa aga tta agg aaa gat ata gaa gta tta tcc gaa gat act gat      2586
Pro Glu Arg Leu Arg Lys Asp Ile Glu Val Leu Ser Glu Asp Thr Asp
        695                 700                 705 tat gaa gaa gat gaa gtc aca aaa aag aga aag gat gtc aag aag gac      2634
Tyr Glu Glu Asp Glu Val Thr Lys Lys Arg Lys Asp Val Lys Lys Asp
    710                 715                 720 aca aca gat aaa tct tca aaa cca caa ata aaa cgt ggt aaa aga agg      2682
Thr Thr Asp Lys Ser Ser Lys Pro Gln Ile Lys Arg Gly Lys Arg Arg
725                 730                 735                 740 tat tgc aat aca gaa gag tgt cta aaa act gga tca cct ggc aaa aag      2730
Tyr Cys Asn Thr Glu Glu Cys Leu Lys Thr Gly Ser Pro Gly Lys Lys
                745                 750                 755
```

-continued

| | | |
|---|---|---|
| gaa gag aag gcc aag aac aaa gaa tca ctt tgc atg gaa aac agt agc<br>Glu Glu Lys Ala Lys Asn Lys Glu Ser Leu Cys Met Glu Asn Ser Ser<br>760                             765                              770 | 2778 |
| aac agc tct tca gat gaa gat gaa gaa gaa aca aaa gca aag atg aca<br>Asn Ser Ser Ser Asp Glu Asp Glu Glu Glu Thr Lys Ala Lys Met Thr<br>775                             780                             785 | 2826 |
| cca act aag aaa tac aat ggt ttg gag gaa aaa aga aaa tct cta cgg<br>Pro Thr Lys Lys Tyr Asn Gly Leu Glu Glu Lys Arg Lys Ser Leu Arg<br>790                             795                             800 | 2874 |
| aca act ggt ttc tat tca gga ttt tca gaa gtg gca gaa aaa agg att<br>Thr Thr Gly Phe Tyr Ser Gly Phe Ser Glu Val Ala Glu Lys Arg Ile<br>805                           810                           815                     820 | 2922 |
| aaa ctt tta aat aac tct gat gaa aga ctt caa aac agc agg gcc aaa<br>Lys Leu Leu Asn Asn Ser Asp Glu Arg Leu Gln Asn Ser Arg Ala Lys<br>825                           830                             835 | 2970 |
| gat cga aaa gat gtc tgg tca agt att cag gga cag tgg cct aaa aaa<br>Asp Arg Lys Asp Val Trp Ser Ser Ile Gln Gly Gln Trp Pro Lys Lys<br>840                           845                           850 | 3018 |
| acg ctg aaa gag ctt ttt tca gac tct gat act gag gct gca gct tcc<br>Thr Leu Lys Glu Leu Phe Ser Asp Ser Asp Thr Glu Ala Ala Ala Ser<br>855                           860                            865 | 3066 |
| cca ccg cat cct gcc cca gag gag ggg gtg gca gag gag tca ctg cag<br>Pro Pro His Pro Ala Pro Glu Glu Gly Val Ala Glu Glu Ser Leu Gln<br>870                           875                           880 | 3114 |
| act gtg gct gaa gag gag agt tgt tca ccc agt gta gaa cta gaa aaa<br>Thr Val Ala Glu Glu Glu Ser Cys Ser Pro Ser Val Glu Leu Glu Lys<br>885                           890                           895                     900 | 3162 |
| cca cct cca gtc aat gtc gat agt aaa ccc att gaa gaa gaa aca gta<br>Pro Pro Pro Val Asn Val Asp Ser Lys Pro Ile Glu Glu Glu Thr Val<br>                           905                           910                           915 | 3210 |
| gag gtc aat gac aga aaa gca gaa ttt cca agt agt ggc agt aat tca<br>Glu Val Asn Asp Arg Lys Ala Glu Phe Pro Ser Ser Gly Ser Asn Ser<br>920                           925                             930 | 3258 |
| gtg cta aat acc cct cct act aca cct gaa tcg cct tca tca gtc act<br>Val Leu Asn Thr Pro Pro Thr Thr Pro Glu Ser Pro Ser Ser Val Thr<br>935                           940                             945 | 3306 |
| gta aca gaa ggc agc cgg cag cag tct tct gta aca gta tca gaa cca<br>Val Thr Glu Gly Ser Arg Gln Gln Ser Ser Val Thr Val Ser Glu Pro<br>950                           955                           960 | 3354 |
| ctg gct cca aac caa gaa gag gtt cga agt atc aag agt gaa act gat<br>Leu Ala Pro Asn Gln Glu Glu Val Arg Ser Ile Lys Ser Glu Thr Asp<br>965                           970                           975                     980 | 3402 |
| agc aca att gag gtg gat agt gtt gct ggg gag ctc caa gac ctc cag<br>Ser Thr Ile Glu Val Asp Ser Val Ala Gly Glu Leu Gln Asp Leu Gln<br>                           985                           990                     995 | 3450 |
| tct gaa ggg aat agc tcg cca gca ggt ttt gat gcc agt gtg agc tca<br>Ser Glu Gly Asn Ser Ser Pro Ala Gly Phe Asp Ala Ser Val Ser Ser<br>              1000                     1005                     1010 | 3498 |
| agc agt agt aat cag cca gaa cca gaa cat cct gaa aaa gcc tgt aca<br>Ser Ser Ser Asn Gln Pro Glu Pro Glu His Pro Glu Lys Ala Cys Thr<br>1015                       1020                     1025 | 3546 |
| ggt cag aaa aga gtg aaa gat gct cag gga gga gga agt tca tca aaa<br>Gly Gln Lys Arg Val Lys Asp Ala Gln Gly Gly Gly Ser Ser Ser Lys<br>1030                       1035                     1040 | 3594 |
| aag cag aaa aga agc cat aaa gca aca gtg gta aac aac aaa aag aag<br>Lys Gln Lys Arg Ser His Lys Ala Thr Val Val Asn Asn Lys Lys Lys<br>1045                       1050                     1055                     1060 | 3642 |
| gga aaa ggc aca aat agt agt gat agt gaa gaa ctt tca gct ggt gaa<br>Gly Lys Gly Thr Asn Ser Ser Asp Ser Glu Glu Leu Ser Ala Gly Glu<br>1065                       1070                     1075 | 3690 |

-continued

| | |
|---|---|
| agt ata act aag agt cag cca gtc aaa tca gtt tcc act gga atg aag<br>Ser Ile Thr Lys Ser Gln Pro Val Lys Ser Val Ser Thr Gly Met Lys<br>        1080                    1085                  1090 | 3738 |
| tct cat agt acc aaa tct ccc gca agg acg cag tct cca gga aaa tgt<br>Ser His Ser Thr Lys Ser Pro Ala Arg Thr Gln Ser Pro Gly Lys Cys<br>              1095                    1100                  1105 | 3786 |
| gga aag aat ggt gat aag gat cct gat ctc aag gaa ccc agt aat cga<br>Gly Lys Asn Gly Asp Lys Asp Pro Asp Leu Lys Glu Pro Ser Asn Arg<br>   1110                    1115                    1120 | 3834 |
| tta ccc aaa gtt tac aaa tgg agt ttt cag atg tcg gac ctg gaa aat<br>Leu Pro Lys Val Tyr Lys Trp Ser Phe Gln Met Ser Asp Leu Glu Asn<br>1125                  1130                  1135                  1140 | 3882 |
| atg aca agt gcc gaa cgc atc aca att ctt caa gaa aaa ctt caa gaa<br>Met Thr Ser Ala Glu Arg Ile Thr Ile Leu Gln Glu Lys Leu Gln Glu<br>        1145                    1150                  1155 | 3930 |
| atc aga aaa cat tat ctg tca tta aaa tct gaa gta gct tcc att gat<br>Ile Arg Lys His Tyr Leu Ser Leu Lys Ser Glu Val Ala Ser Ile Asp<br>    1160                    1165                    1170 | 3978 |
| cgg agg aga aag cgt tta aag aag aaa gag aga gaa agt gct gct aca<br>Arg Arg Arg Lys Arg Leu Lys Lys Lys Glu Arg Glu Ser Ala Ala Thr<br>           1175                    1180                  1185 | 4026 |
| tcc tca tcc tcc tct tca cct tca tcc agc tcc ata aca gct gct gct<br>Ser Ser Ser Ser Ser Ser Pro Ser Ser Ser Ser Ile Thr Ala Ala Ala<br>   1190                    1195                    1200 | 4074 |
| atg tta act tta gct gaa ccg tca atg tcc agc gca tca caa aat gga<br>Met Leu Thr Leu Ala Glu Pro Ser Met Ser Ser Ala Ser Gln Asn Gly<br>1205                  1210                  1215                  1220 | 4122 |
| atg tca gtt gag tgc agg tga cagcaggact tgctaaggca ctttgcactt<br>Met Ser Val Glu Cys Arg<br>           1225 | 4173 |
| aatggctgtt gagggccact ttttttttat actgcacagt ggcacaaaaa aatatcagac | 4233 |
| aagcactatt ttatatttaa aaattgtttc ttgacaagcc gacttggcac ttaagtgcac | 4293 |
| ttttgtatga agaaaagtac aatgaactgc ttttcctcaa gcaataattg tttccaactt | 4353 |
| gtctgggaat tgtgtgtctg gtaactggaa ggccttccac tgtggcaaat ggaggcttct | 4413 |
| cactgcctgt agagacaata cagtaagcat agttaagggg tgggtcagaa catgttaaga | 4473 |
| taacttactg tatatgtatt cccttgtatt ttgttaaagc tggaacattt gatattttc | 4533 |
| catttattta tgaaaaaata tgaacctatt ttcatttgta caaggtaatt gttttttaaa | 4593 |
| gcaagtcacc ttagggtggc tttaattgta taagtcaagc acatgtaata aattcaaaac | 4653 |
| ctgcagttaa caggatatta gacattaatc ctggtaacca aatattaaag attctcttta | 4713 |
| aaaaagactg aacatgttta caggtttgaa ttaggctaaa aggtcttgca gtggcttttc | 4773 |
| atggcccttc aaattggaat ggaactactg tactttgcca ttttctata aatcagtatt | 4833 |
| ttttttttaat tttgatatac attgtgtgaa aaaagaaaat ggctaataaa ctgtattaaa | 4893 |
| tcttaaacaa tgtataaaga ttgtacttag ccagttcaaa ggtatattta ttcataatga | 4953 |
| attataacag ttatattttt gtgttttctt gtaaatgttt cttttccctt aaatacagat | 5013 |
| aattcatttg tattgcttat tttattatga gctacaacaa aaggacttca ggaacaagta | 5073 |
| atgtattagt atggttcaag attgttgata ggaactgtct caaaaggatg gtggttattt | 5133 |
| taaatataaa tagctaatgg gggtggtagg cctataaaat taaatgcctt gtataagatc | 5193 |
| caaaatgaat gcaaaattgt tttcacttgt attgacttta tgttgtatga ttccaatctc | 5253 |
| tgttctgttt ggcacttgta tttaattctt cacctttgta agacatttgt atattgtgga | 5313 |

```
tgtgttcatt caagctattt aatatctggc actgttaata cacagtactt tattgtacag      5373
actgttttac tgttttaatt gtagttctgt gtactttttt tggatggggc tggcatgttt      5433
tctttgtttc ctggcaatac gacgtgggaa tttcaatgcg ttttgttgta gatgctaacg      5493
tgtcagaatc ctttacattc aacttttcta agaaaagcat tttcagtctt gtagtgtgtg      5553
cttacagtaa ctaattttgt tgaaaatggt ttcaagttat tcaaatttgt acaggactgt      5613
aaagatttgt tgacagcaaa atgttgaaga aaaaagctta tagaataaaa gctataaagt      5673
atatattagg atctgcaaac aatgaagaat tatgtaatat attgtacaaa tgtaaagcaa      5733
aggctttgaa ataaaatgcc attgtttgtg aatccttaaa aaaaaaaaaa aaaaaaaaa      5793 aaaaaaaaa                                                              5802
```

<210> SEQ ID NO 2
<211> LENGTH: 1226
<212> TYPE: PRT
<213> ORGANISM: Homo sapiens

<400> SEQUENCE: 2

```
Met Lys Ala Leu Asp Glu Pro Pro Tyr Leu Thr Val Gly Thr Asp Val
  1               5                  10                  15

Ser Ala Lys Tyr Arg Gly Ala Phe Cys Glu Ala Lys Ile Lys Thr Ala
             20                  25                  30

Lys Arg Leu Val Lys Val Lys Val Thr Phe Arg His Asp Ser Ser Thr
         35                  40                  45

Val Glu Val Gln Asp Asp His Ile Lys Gly Pro Leu Lys Val Gly Ala
     50                  55                  60

Ile Val Glu Val Lys Asn Leu Asp Gly Ala Tyr Gln Glu Ala Val Ile
 65                  70                  75                  80

Asn Lys Leu Thr Asp Ala Ser Trp Tyr Thr Val Phe Asp Asp Gly
                 85                  90                  95

Asp Glu Lys Thr Leu Arg Arg Ser Leu Cys Leu Lys Gly Glu Arg
            100                 105                 110

His Phe Ala Glu Ser Glu Thr Leu Asp Gln Leu Pro Leu Thr Asn Pro
        115                 120                 125

Glu His Phe Gly Thr Pro Val Ile Gly Lys Lys Thr Asn Arg Gly Arg
    130                 135                 140

Arg Ser Asn His Ile Pro Glu Glu Ser Ser Ser Ser Ser Ser Asp
145                 150                 155                 160

Glu Asp Glu Asp Asp Arg Lys Gln Ile Asp Glu Leu Leu Gly Lys Val
                165                 170                 175

Val Cys Val Asp Tyr Ile Ser Leu Asp Lys Lys Ala Leu Trp Phe
            180                 185                 190

Pro Ala Leu Val Val Cys Pro Asp Cys Ser Asp Glu Ile Ala Val Lys
        195                 200                 205

Lys Asp Asn Ile Leu Val Arg Ser Phe Lys Asp Gly Lys Phe Thr Ser
    210                 215                 220

Val Pro Arg Lys Asp Val His Glu Ile Thr Ser Asp Thr Ala Pro Lys
225                 230                 235                 240

Pro Asp Ala Val Leu Lys Gln Ala Phe Glu Gln Ala Leu Glu Phe His
                245                 250                 255

Lys Ser Arg Thr Ile Pro Ala Asn Trp Lys Thr Glu Leu Lys Glu Asp
            260                 265                 270

Ser Ser Ser Ser Glu Ala Glu Glu Glu Glu Glu Glu Asp Asp Glu
        275                 280                 285
```

```
Lys Glu Lys Glu Asp Asn Ser Ser Glu Glu Glu Glu Ile Glu Pro
    290                 295                 300

Phe Pro Glu Glu Arg Glu Asn Phe Leu Gln Gln Leu Tyr Lys Phe Met
305                 310                 315                 320

Glu Asp Arg Gly Thr Pro Ile Asn Lys Gln Pro Val Leu Gly Tyr Arg
                325                 330                 335

Asn Leu Asn Leu Phe Lys Leu Phe Arg Leu Val His Lys Leu Gly Gly
            340                 345                 350

Phe Asp Asn Ile Glu Ser Gly Ala Val Trp Lys Gln Val Tyr Gln Asp
        355                 360                 365

Leu Gly Ile Pro Val Leu Asn Ser Ala Ala Gly Tyr Asn Val Lys Cys
    370                 375                 380

Ala Tyr Lys Lys Tyr Leu Tyr Gly Phe Glu Glu Tyr Cys Arg Ser Ala
385                 390                 395                 400

Asn Ile Glu Phe Gln Met Ala Leu Pro Glu Lys Val Val Asn Lys Gln
                405                 410                 415

Cys Lys Glu Cys Glu Asn Val Lys Glu Ile Lys Val Lys Glu Glu Asn
            420                 425                 430

Glu Thr Glu Ile Lys Glu Ile Lys Met Glu Glu Arg Asn Ile Ile
        435                 440                 445

Pro Arg Glu Glu Lys Pro Ile Glu Asp Glu Ile Glu Arg Lys Glu Asn
    450                 455                 460

Ile Lys Pro Ser Leu Gly Ser Lys Lys Asn Leu Leu Glu Ser Ile Pro
465                 470                 475                 480

Thr His Ser Asp Gln Glu Lys Glu Val Asn Ile Lys Lys Pro Glu Asp
                485                 490                 495

Asn Glu Asn Leu Asp Asp Lys Asp Asp Asp Thr Arg Val Asp Glu
            500                 505                 510

Ser Leu Asn Ile Lys Val Glu Ala Glu Glu Lys Ala Lys Ser Gly
        515                 520                 525

Tyr Asp Glu Trp Ile Lys Ala Asp Lys Ile Val Arg Pro Ala Asp Lys
    530                 535                 540

Asn Val Pro Lys Ile Lys His Arg Lys Lys Ile Lys Asn Lys Leu Asp
545                 550                 555                 560

Lys Glu Lys Asp Lys Asp Glu Lys Tyr Ser Pro Lys Asn Cys Lys Leu
                565                 570                 575

Arg Arg Leu Ser Lys Pro Pro Phe Gln Thr Asn Pro Ser Pro Glu Met
            580                 585                 590

Val Ser Lys Leu Asp Leu Thr Asp Ala Lys Asn Ser Asp Thr Ala His
        595                 600                 605

Ile Lys Ser Ile Glu Ile Thr Ser Ile Leu Asn Gly Leu Gln Ala Ser
    610                 615                 620

Glu Ser Ser Ala Glu Asp Ser Glu Gln Glu Asp Glu Arg Gly Ala Gln
625                 630                 635                 640

Asp Met Asp Asn Asn Gly Lys Glu Glu Ser Lys Ile Asp His Leu Thr
                645                 650                 655

Asn Asn Arg Asn Asp Leu Ile Ser Lys Glu Glu Gln Asn Ser Ser Ser
            660                 665                 670

Leu Leu Glu Glu Asn Lys Val His Ala Asp Leu Val Ile Ser Lys Pro
        675                 680                 685

Val Ser Lys Ser Pro Glu Arg Leu Arg Lys Asp Ile Glu Val Leu Ser
    690                 695                 700
```

-continued

```
Glu Asp Thr Asp Tyr Glu Glu Asp Glu Val Thr Lys Lys Arg Lys Asp
705                 710                 715                 720

Val Lys Lys Asp Thr Thr Asp Lys Ser Ser Lys Pro Gln Ile Lys Arg
            725                 730                 735

Gly Lys Arg Arg Tyr Cys Asn Thr Glu Glu Cys Leu Lys Thr Gly Ser
        740                 745                 750

Pro Gly Lys Lys Glu Glu Lys Ala Lys Asn Lys Glu Ser Leu Cys Met
    755                 760                 765

Glu Asn Ser Ser Asn Ser Ser Ser Asp Glu Asp Glu Glu Thr Lys
770                 775                 780

Ala Lys Met Thr Pro Thr Lys Lys Tyr Asn Gly Leu Glu Glu Lys Arg
785                 790                 795                 800

Lys Ser Leu Arg Thr Thr Gly Phe Tyr Ser Gly Phe Ser Glu Val Ala
            805                 810                 815

Glu Lys Arg Ile Lys Leu Leu Asn Asn Ser Asp Glu Arg Leu Gln Asn
        820                 825                 830

Ser Arg Ala Lys Asp Arg Lys Asp Val Trp Ser Ser Ile Gln Gly Gln
    835                 840                 845

Trp Pro Lys Lys Thr Leu Lys Glu Leu Phe Ser Asp Ser Asp Thr Glu
850                 855                 860

Ala Ala Ala Ser Pro Pro His Pro Ala Pro Glu Glu Gly Val Ala Glu
865                 870                 875                 880

Glu Ser Leu Gln Thr Val Ala Glu Glu Ser Cys Ser Pro Ser Val
            885                 890                 895

Glu Leu Glu Lys Pro Pro Pro Val Asn Val Asp Ser Lys Pro Ile Glu
        900                 905                 910

Glu Glu Thr Val Glu Val Asn Asp Arg Lys Ala Glu Phe Pro Ser Ser
    915                 920                 925

Gly Ser Asn Ser Val Leu Asn Thr Pro Pro Thr Thr Pro Glu Ser Pro
930                 935                 940

Ser Ser Val Thr Val Thr Glu Gly Ser Arg Gln Gln Ser Ser Val Thr
945                 950                 955                 960

Val Ser Glu Pro Leu Ala Pro Asn Gln Glu Glu Val Arg Ser Ile Lys
            965                 970                 975

Ser Glu Thr Asp Ser Thr Ile Glu Val Asp Ser Val Ala Gly Glu Leu
        980                 985                 990

Gln Asp Leu Gln Ser Glu Gly Asn Ser Ser Pro Ala Gly Phe Asp Ala
    995                 1000                1005

Ser Val Ser Ser Ser Ser Asn Gln Pro Glu Pro Glu His Pro Glu
1010                1015                1020

Lys Ala Cys Thr Gly Gln Lys Arg Val Lys Asp Ala Gln Gly Gly Gly
1025                1030                1035                1040

Ser Ser Ser Lys Lys Gln Lys Arg Ser His Lys Ala Thr Val Val Asn
            1045                1050                1055

Asn Lys Lys Lys Gly Lys Gly Thr Asn Ser Ser Asp Ser Glu Glu Leu
        1060                1065                1070

Ser Ala Gly Glu Ser Ile Thr Lys Ser Gln Pro Val Lys Ser Val Ser
    1075                1080                1085

Thr Gly Met Lys Ser His Ser Thr Lys Ser Pro Ala Arg Thr Gln Ser
1090                1095                1100

Pro Gly Lys Cys Gly Lys Asn Gly Asp Lys Asp Pro Asp Leu Lys Glu
1105                1110                1115                1120

Pro Ser Asn Arg Leu Pro Lys Val Tyr Lys Trp Ser Phe Gln Met Ser
```

-continued

```
                1125                1130                1135
Asp Leu Glu Asn Met Thr Ser Ala Glu Arg Ile Thr Ile Leu Gln Glu
        1140                1145                1150
Lys Leu Gln Glu Ile Arg Lys His Tyr Leu Ser Leu Lys Ser Glu Val
        1155                1160                1165
Ala Ser Ile Asp Arg Arg Lys Arg Leu Lys Lys Glu Arg Glu
        1170                1175                1180
Ser Ala Ala Thr Ser Ser Ser Ser Ser Pro Ser Ser Ser Ile
1185                1190                1195                1200
Thr Ala Ala Ala Met Leu Thr Leu Ala Glu Pro Ser Met Ser Ser Ala
        1205                1210                1215
Ser Gln Asn Gly Met Ser Val Glu Cys Arg
        1220                1225

<210> SEQ ID NO 3
<211> LENGTH: 9
<212> TYPE: PRT
<213> ORGANISM: Homo sapiens

<400> SEQUENCE: 3

Ile Lys Pro Ser Leu Gly Ser Lys Lys
  1               5

<210> SEQ ID NO 4
<211> LENGTH: 1255
<212> TYPE: PRT
<213> ORGANISM: Homo sapiens

<400> SEQUENCE: 4

Met Lys Ala Ala Asp Glu Pro Ala Tyr Leu Thr Val Gly Thr Asp Val
  1               5                  10                  15
Ser Ala Lys Tyr Arg Gly Ala Phe Cys Glu Ala Lys Ile Lys Thr Val
                 20                  25                  30
Lys Arg Leu Val Lys Val Lys Val Leu Leu Lys Gln Asp Asn Thr Thr
         35                  40                  45
Gln Leu Val Gln Asp Asp Gln Val Lys Gly Pro Leu Arg Val Gly Ala
     50                  55                  60
Ile Val Glu Thr Arg Thr Ser Asp Gly Ser Phe Gln Glu Ala Ile Ile
 65                  70                  75                  80
Ser Lys Leu Thr Asp Ala Ser Trp Tyr Thr Val Phe Asp Asp Gly
                 85                  90                  95
Asp Glu Arg Thr Leu Arg Arg Thr Ser Leu Cys Leu Lys Gly Glu Arg
                100                 105                 110
His Phe Ala Glu Ser Glu Thr Leu Asp Gln Leu Pro Leu Thr Asn Pro
        115                 120                 125
Glu His Phe Gly Thr Pro Val Ile Ala Lys Lys Thr Asn Arg Gly Arg
    130                 135                 140
Arg Ser Ser Leu Pro Val Thr Glu Asp Glu Lys Glu Glu Ser Ser
145                 150                 155                 160
Glu Glu Glu Asp Glu Asp Lys Arg Arg Leu Asn Asp Glu Leu Leu Gly
                165                 170                 175
Lys Val Val Ser Val Val Ser Ala Thr Glu Arg Thr Glu Trp Tyr Pro
            180                 185                 190
Ala Leu Val Ile Ser Pro Ser Cys Asn Asp Asp Ile Thr Val Lys Lys
        195                 200                 205
Asp Gln Cys Leu Val Arg Ser Phe Ile Asp Ser Lys Phe Tyr Ser Ile
```

-continued

```
            210                 215                 220
Ala Arg Lys Asp Ile Lys Glu Val Asp Ile Leu Asn Leu Pro Glu Ser
225                 230                 235                 240

Glu Leu Ser Thr Lys Pro Gly Leu Gln Lys Ala Ser Ile Phe Leu Lys
                245                 250                 255

Thr Arg Val Val Pro Asp Asn Trp Lys Met Asp Ile Ser Glu Ile Leu
                260                 265                 270

Glu Ser Ser Ser Asp Asp Glu Asp Gly Pro Ala Glu Glu Asn Asp
            275                 280                 285

Glu Glu Lys Glu Lys Glu Ala Lys Lys Thr Glu Glu Val Pro Glu
            290                 295                 300

Glu Glu Leu Asp Pro Glu Glu Arg Asp Asn Phe Leu Gln Gln Leu Tyr
305                 310                 315                 320

Lys Phe Met Glu Asp Arg Gly Thr Pro Ile Asn Lys Pro Pro Val Leu
                325                 330                 335

Gly Tyr Lys Asp Leu Asn Leu Phe Lys Leu Phe Arg Leu Val Tyr His
                340                 345                 350

Gln Gly Gly Cys Asp Asn Ile Asp Ser Gly Ala Val Trp Lys Gln Ile
                355                 360                 365

Tyr Met Asp Leu Gly Ile Pro Ile Leu Asn Ser Ala Ala Ser Tyr Asn
370                 375                 380

Leu Lys Thr Ala Tyr Arg Lys Tyr Leu Tyr Gly Phe Glu Glu Tyr Cys
385                 390                 395                 400

Arg Ser Ala Asn Ile Gln Phe Arg Thr Val His His Glu Pro Lys
                405                 410                 415

Val Lys Glu Glu Lys Lys Asp Leu Glu Glu Ser Met Glu Glu Ala Leu
                420                 425                 430

Lys Leu Asp Gln Glu Met Pro Leu Thr Glu Val Lys Ser Glu Pro Glu
                435                 440                 445

Glu Asn Ile Asp Ser Asn Ser Glu Ser Glu Arg Glu Glu Ile Glu Leu
                450                 455                 460

Lys Ser Pro Arg Gly Arg Arg Ile Ala Arg Asp Val Asn Ser Ile
465                 470                 475                 480

Lys Lys Glu Ile Glu Glu Lys Thr Glu Asp Lys Leu Lys Asp Asn
                485                 490                 495

Asp Thr Glu Asn Lys Asp Val Asp Asp Tyr Glu Thr Ala Glu Lys
                500                 505                 510

Lys Glu Asn Glu Leu Leu Leu Gly Arg Lys Asn Thr Pro Lys Gln Lys
                515                 520                 525

Glu Lys Lys Ile Lys Lys Gln Glu Asp Ser Asp Lys Asp Ser Asp Glu
                530                 535                 540

Glu Glu Glu Lys Ser Gln Glu Arg Glu Glu Thr Glu Ser Lys Cys Asp
545                 550                 555                 560

Ser Glu Gly Glu Glu Asp Glu Glu Asp Met Glu Pro Cys Leu Thr Gly
                565                 570                 575

Thr Lys Val Lys Val Lys Tyr Gly Arg Gly Lys Thr Gln Lys Ile Tyr
                580                 585                 590

Glu Ala Ser Ile Lys Ser Thr Glu Ile Asp Asp Gly Glu Val Leu Tyr
                595                 600                 605

Leu Val His Tyr Tyr Gly Trp Asn Val Ser Tyr Asp Glu Trp Val Lys
                610                 615                 620

Ala Asp Arg Ile Ile Trp Pro Leu Asp Lys Gly Gly Pro Lys Lys Lys
625                 630                 635                 640
```

-continued

```
Gln Lys Lys Lys Ala Lys Asn Lys Glu Asp Ser Glu Lys Asp Glu Lys
            645                 650                 655
Arg Asp Glu Glu Arg Gln Lys Ser Lys Arg Gly Arg Pro Pro Leu Lys
        660                 665                 670
Ser Thr Leu Ser Ser Asn Met Pro Tyr Gly Leu Ser Lys Thr Ala Asn
    675                 680                 685
Ser Glu Gly Lys Ser Asp Ser Cys Ser Ser Asp Ser Glu Thr Glu Asp
690                 695                 700
Ala Leu Glu Lys Asn Leu Ile Asn Glu Glu Leu Ser Leu Lys Asp Glu
705                 710                 715                 720
Leu Glu Lys Asn Glu Asn Leu Asn Asp Asp Lys Leu Asp Glu Glu Asn
                725                 730                 735
Pro Lys Ile Ser Ala His Ile Leu Lys Glu Asn Asp Arg Thr Gln Met
            740                 745                 750
Gln Pro Leu Glu Thr Leu Lys Leu Glu Val Gly Glu Asn Gly Gln Ile
        755                 760                 765
Val Gln Ile Phe Gly Asn Lys Met Glu Lys Ala Glu Glu Val Lys Lys
    770                 775                 780
Glu Ala Glu Lys Ser Pro Lys Gly Lys Gly Arg Arg Ser Lys Thr Lys
785                 790                 795                 800
Asp Leu Ser Leu Glu Ile Ile Lys Ile Ser Ser Phe Gly Gln Asn Glu
                805                 810                 815
Ala Gly Ser Glu Pro His Ile Glu Ala His Ser Leu Glu Leu Ser Ser
            820                 825                 830
Leu Asp Asn Lys Asn Phe Ser Ser Ala Thr Glu Asp Glu Ile Asp Gln
        835                 840                 845
Cys Val Lys Glu Lys Lys Leu Lys Arg Lys Ile Leu Gly Gln Ser Ser
    850                 855                 860
Pro Glu Lys Lys Ile Arg Ile Glu Asn Gly Met Glu Met Thr Asn Thr
865                 870                 875                 880
Val Ser Gln Glu Arg Thr Ser Asp Cys Ile Gly Ser Glu Gly Met Lys
                885                 890                 895
Asn Leu Asn Phe Glu Gln His Phe Glu Arg Glu Asn Glu Gly Met Pro
            900                 905                 910
Ser Leu Ile Ala Glu Ser Asn Gln Cys Ile Gln Gln Leu Thr Ser Glu
        915                 920                 925
Arg Phe Asp Ser Pro Ala Glu Glu Thr Val Asn Ile Pro Leu Lys Glu
    930                 935                 940
Asp Glu Asp Ala Met Pro Leu Ile Gly Pro Glu Thr Leu Val Cys His
945                 950                 955                 960
Glu Val Asp Leu Asp Asp Leu Asp Glu Lys Asp Lys Thr Ser Ile Glu
                965                 970                 975
Asp Val Ala Val Glu Ser Ser Glu Ser Asn Ser Leu Val Ser Ile Pro
            980                 985                 990
Pro Ala Leu Pro Pro Val Val Gln His Asn Phe Ser Val Ala Ser Pro
        995                1000                1005
Leu Thr Leu Ser Gln Asp Glu Ser Arg Ser Val Lys Glu Ser Asp Ile
    1010                1015                1020
Thr Ile Glu Val Asp Ser Ile Ala Glu Glu Ser Gln Glu Gly Leu Cys
1025                1030                1035                1040
Glu Arg Glu Ser Ala Asn Gly Phe Glu Thr Asn Val Ala Ser Gly Thr
                1045                1050                1055
```

-continued

```
Cys Ser Ile Ile Val Gln Glu Arg Glu Ser Arg Glu Lys Gly Gln Lys
        1060                1065                1070

Arg Pro Ser Asp Gly Asn Ser Leu Met Ala Lys Lys Gln Lys Arg Thr
        1075                1080                1085

Pro Lys Arg Thr Ser Ala Ala Ala Lys Asn Glu Lys Asn Gly Thr Gly
        1090                1095                1100

Gln Ser Ser Asp Ser Glu Asp Leu Pro Val Leu Asp Asn Ser Ser Lys
1105                1110                1115                1120

Cys Thr Pro Val Lys His Leu Asn Val Ser Lys Pro Gln Lys Leu Ala
            1125                1130                1135

Arg Ser Pro Ala Arg Ile Ser Pro His Ile Lys Asp Gly Glu Lys Asp
        1140                1145                1150

Lys His Arg Glu Lys His Pro Asn Ser Ser Pro Arg Thr Tyr Lys Trp
        1155                1160                1165

Ser Phe Gln Leu Asn Glu Leu Asp Asn Met Asn Ser Thr Glu Arg Ile
        1170                1175                1180

Ser Phe Leu Gln Glu Lys Leu Gln Glu Ile Arg Lys Tyr Tyr Met Ser
1185                1190                1195                1200

Leu Lys Ser Glu Val Ala Thr Ile Asp Arg Arg Arg Lys Arg Leu Lys
        1205                1210                1215

Lys Lys Asp Arg Glu Val Ser His Ala Gly Ala Ser Met Ser Ser Ala
        1220                1225                1230

Ser Ser Asp Thr Gly Met Ser Pro Ser Ser Ser Pro Pro Gln Asn
        1235                1240                1245

Val Leu Ala Val Glu Cys Arg
        1250                1255

<210> SEQ ID NO 5
<211> LENGTH: 7
<212> TYPE: PRT
<213> ORGANISM: Homo sapiens

<400> SEQUENCE: 5

Lys Ala Ser Ile Phe Leu Lys
 1               5

<210> SEQ ID NO 6
<211> LENGTH: 10
<212> TYPE: PRT
<213> ORGANISM: Homo sapiens

<400> SEQUENCE: 6

Gly Leu Gln Lys Ala Ser Ile Phe Leu Lys
 1               5                  10

<210> SEQ ID NO 7
<211> LENGTH: 10
<212> TYPE: PRT
<213> ORGANISM: Homo sapiens

<400> SEQUENCE: 7

Lys Ala Ser Ile Phe Leu Lys Thr Arg Val
 1               5                  10

<210> SEQ ID NO 8
<211> LENGTH: 29
<212> TYPE: DNA
<213> ORGANISM: Homo sapiens

<400> SEQUENCE: 8
```

```
atggaggagg agaggaatat aataccaag                                    29

<210> SEQ ID NO 9
<211> LENGTH: 28
<212> TYPE: DNA
<213> ORGANISM: Homo sapiens

<400> SEQUENCE: 9
ctgaaatggt ggtttggaca agcgccga                                     28

<210> SEQ ID NO 10
<211> LENGTH: 31
<212> TYPE: DNA
<213> ORGANISM: Homo sapiens

<400> SEQUENCE: 10
agagtcacca tgaaggccct tgatgatgag c                                 31

<210> SEQ ID NO 11
<211> LENGTH: 28
<212> TYPE: DNA
<213> ORGANISM: Homo sapiens

<400> SEQUENCE: 11
tgggattata ttcctctcct cctccatc                                     28

<210> SEQ ID NO 12
<211> LENGTH: 30
<212> TYPE: DNA
<213> ORGANISM: Homo sapiens

<400> SEQUENCE: 12
atacggcatc aggctttggt gcagtgtcac                                   30

<210> SEQ ID NO 13
<211> LENGTH: 29
<212> TYPE: DNA
<213> ORGANISM: Homo sapiens

<400> SEQUENCE: 13
agggaatagc tcgccagcag gttttgatg                                    29

<210> SEQ ID NO 14
<211> LENGTH: 30
<212> TYPE: DNA
<213> ORGANISM: Homo sapiens

<400> SEQUENCE: 14
tcggcacttg tcatattttc caggtccgac                                   30

<210> SEQ ID NO 15
<211> LENGTH: 5804
<212> TYPE: DNA
<213> ORGANISM: Homo sapiens

<400> SEQUENCE: 15
agcgatgttt gcccgtcagt cgagtccgga gtgaggagct cggtcgccga agcggaggga    60
gactcttgag cttcatcttg ccgccgccac ggccaccgcc tggacctttg cccggaggga   120
gctgcagagg gtccatcgcc gccgtcctct ggagggcagc gcgattgggg gcccggacct   180
ccagtccggg ggggattttt cgtcgtcccc ctccccccaa ccagggagcc cgagcggccg   240
```

```
ccaaacaaag gtaccagtcg ccgccgcggg aggaggagga gccggagcct ctgcctcaca      300
gccgctggac ccgccgcctt cttccccatc tctccccegg gcctgctggt tttgggggg      360 agaaggagag agggactct  ggacgtgcca gggtcaaatc tcgcctccga ggaaggtgca     420
actgaacctg gtgttttaaa ggataccttg gtcccaaagt catcatgaag gcccttgatg    480
agcctcccta tttgacagtg ggcactgatg tgagtgctaa atacagagga gccttttgtg    540
aagccaagat caagacagca aaaagacttg tcaaagtcaa ggtgacattt agacatgatt    600
cttcaacagt ggaagttcag gatgaccaca taaagggccc actaaaggta ggagctattg    660
tggaagtgaa gaatcttgat ggtgcatatc aggaagctgt tatcaataaa ctaacagatg    720
cgagttggta cactgtagtt tttgatgacg gagatgagaa gacactgaga cgatcttcac    780
tgtgcctgaa aggagagagg cattttgccg aaagtgaaac attagaccag ctcccactca    840
ccaaccctga gcattttggc actccagtca taggaaagaa aacaaataga ggaagaagat    900
ctaatcatat accagaggaa gagtcttcat catcctccag tgatgaagat gaggatgata    960
ggaaacagat tgatgagcta ctaggcaaag ttgtatgtgt agattacatt agtttggata    1020
aaaagaaagc actgtggttt cctgcattgg tggtttgtcc tgattgtagt gatgagattg    1080
ctgtaaaaaa ggacaatatt cttgttcgat cttcaaaga tggaaaattt acttcagttc     1140
caagaaaaga tgtccatgaa attactagtg acactgcacc aaagcctgat gctgttttaa    1200
agcaagcctt tgaacaggca cttgaatttc acaaaagtag aactattcct gctaactgga    1260
agactgaatt gaaagaagat agctctagca gtgaagcaga ggaagaagag gaggaggaag    1320
atgatgaaaa agaaaaggag gataatagca gtgaagaaga agaagaaata gaaccatttc    1380
cagaagaaag ggagaacttt cttcagcaat tgtacaaatt tatggaagat agaggtacac    1440
ctattaacaa acaacctgta cttggatatc gaaatttgaa tctctttaag ttattcagac    1500
ttgtacacaa acttggagga tttgataata ttgaaagtgg agctgtttgg aaacaagtct    1560
accaagatct tggaatccct gtcttaaatt cagctgcagg atacaatgtt aaatgtgctt    1620
ataaaaaata cttatatggt tttgaggagt actgtagatc agccaacatt gaatttcaga    1680
tggcattgcc agagaaagtt gttaacaagc aatgtaagga gtgtgaaaat gtaaaagaaa    1740
taaaagttaa ggaggaaaat gaaacagaga tcaaagaaat aaagatggag gaggagagga    1800
atataatacc aagagaagaa aagcctattg aggatgaaat tgaaagaaaa gaaaatatta    1860
agccctctct gggaagtaaa aagaatttat tagaatctat acctacacat tctgatcagg    1920
aaaaagaagt taacattaaa aaaccagaag acaatgaaaa tctggatgac aaagatgatg    1980
acacaactag ggtagatgaa tccctcaaca taaaggtaga agctgaggaa gaaaaagcaa    2040
aatctggata cgatgaatgg attaaagcag ataaaatagt aagacctgct gataaaaatg    2100
tgccaaagat aaaacatcgg aagaaaataa agaataaatt agacaaagaa aaagacaaag    2160
atgaaaaata ctctccaaaa aactgtaaac ttcggcgctt gtccaaacca ccatttcaga    2220
caaatccatc tcctgaaatg gtatccaaac tggatctcac tgatgccaaa aactctgata    2280
ctgctcatat taagtccata gaaattactt cgatccttaa tggacttcaa gcttctgaaa    2340
gttctgctga agacagtgag caggaagatg agagaggtgc tcaagacatg gataataatg    2400
gcaaagaaga atctaagatt gatcatttga ccaacaacag aaatgatctt atttcaaagg    2460
aggaacagaa cagttcatct ttgctagaag aaaacaaagt tcatgcagat ttggtaatat    2520
ccaaaccagt gtcaaaatct ccagaaagat taaggaaaga tatagaagta ttatccgaag    2580
atactgatta tgaagaagat gaagtcacaa aaaagagaaa ggatgtcaag aaggacacaa    2640
```

```
cagataaatc ttcaaaacca caaataaaac gtggtaaaag aaggtattgc aatacagaag    2700
agtgtctaaa aactggatca cctggcaaaa aggaagagaa ggccaagaac aaagaatcac    2760
tttgcatgga aaacagtagc aacagctctt cagatgaaga tgaagaagaa acaaaagcaa    2820
agatgacacc aactaagaaa tacaatggtt tggaggaaaa aagaaaatct ctacggacaa    2880
ctggtttcta ttcaggattt tcagaagtgg cagaaaaaag gattaaactt ttaaataact    2940
ctgatgaaag acttcaaaac agcagggcca agatcgaaa agatgtctgg tcaagtattc     3000
agggacagtg gcctaaaaaa acgctgaaag agctttttc agactctgat actgaggctg     3060
cagcttcccc accgcatcct gccccagagg aggggtggc agaggagtca ctgcagactg     3120
tggctgaaga ggagagttgt tcacccagtg tagaactaga aaaccaccct ccagtcaatg    3180
tcgatagtaa acccattgaa gaagaaacag tagaggtcaa tgacagaaaa gcagaatttc    3240
caagtagtgg cagtaattca gtgctaaata cccctcctac tacacctgaa tcgccttcat    3300
cagtcactgt aacagaaggc agccggcagc agtcttctgt aacagtatca gaaccactgg    3360 ctccaaaacca agaagaggtt cgaagtatca agagtgaaac tgatagcaca attgaggtgg    3420
atagtgttgc tggggagctc caagacctcc agtctgaagg aatagctcg ccagcaggtt     3480 ttgatgccag tgtgagctca agcagtagta atcagccaga accagaacat cctgaaaaag    3540
cctgtacagg tcagaaaaga gtgaaagatg ctcagggagg aggaagttca tcaaaaaagc    3600
agaaaagaag ccataaagca acagtggtaa acaacaaaaa gaagggaaaa ggcacaaata    3660
gtagtgatag tgaagaactt tcagctggtg aaagtataac taagagtcag ccagtcaaat    3720
cagtttccac tggaatgaag tctcatagta ccaaatctcc cgcaaggacg cagtctccag    3780
gaaaatgtgg aaagaatggt gataaggatc ctgatctcaa ggaacccagt aatcgattac    3840
ccaaagttta caaatggagt tttcagatgt cggacctgga aaatatgaca agtgccgaac    3900
gcatcacaat tcttcaagaa aaacttcaag aaatcagaaa acattatctg tcattaaaat    3960
ctgaagtagc ttccattgat cggaggagaa agcgtttaaa gaagaaagag agagaaagtg    4020
ctgctacatc ctcatcctcc tcttcacctt catccagctc cataacagct gctgctatgt    4080
taactttagc tgaaccgtca atgtccagcg catcacaaaa tggaatgtca gttgagtgca    4140
ggtgacagca ggacttgcta aggcactttg cacttaatgg ctgttgaggg ccactttttt    4200
tttatactgc acagtggcac aaaaaaatat cagacaagca ctatttata tttaaaaatt     4260 gtttcttgac aagccgactt ggcacttaag tgcacttttg tatgaagaaa agtacaatga    4320
actgcttttc ctcaagcaat aattgttttcc aacttgtctg ggaattgtgt gtctggtaac    4380
tggaaggcct tccactgtgg caaatggagg cttctcactg cctgtagaga caatacagta    4440
agcatagtta agggtgggt cagaacatgt taagataact tactgtatat gtattccctt      4500
gtattttgtt aaagctggaa catttgatat ttttccattt atttatgaaa aaatatgaac    4560
ctattttcat ttgtacaagg taattgtttt ttaaagcaag tcaccttagg gtggctttaa    4620
ttgtataagt caagcacatg taataaattc aaaacctgca gttaacagga tattagacat    4680
taatcctggt aaccaaatat taaagattct ctttaaaaaa gactgaacat gtttacaggt    4740
ttgaattagg ctaaaaggtc ttgcagtggc ttttcatggc ccttcaaatt ggaatggaac    4800
tactgtactt tgccatttttt ctataaatca gtatttttt ttaattttga tatacattgt    4860
gtgaaaaaag aaaatggcta ataaactgta ttaaatctta aacaatgtat aaagattgta    4920
cttagccagt tcaaaggtat atttattcat aatgaattat aacagttata tttttgtgtt    4980
```

-continued

```
ttcttgtaaa tgtttctttt cccttaaata cagataattc atttgtattg cttattttat    5040
tatgagctac aacaaaagga cttcaggaac aagtaatgta ttagtatggt tcaagattgt    5100
tgataggaac tgtctcaaaa ggatggtggt tattttaaat ataaatagct aatgggggtg    5160
gtaggcctat aaaattaaat gccttgtata agatccaaaa tgaatgcaaa attgttttca    5220
cttgtattga ctttatgttg tatgattcca atctctgttc tgtttggcac ttgtatttaa    5280
ttcttcacct ttgtaagaca tttgtatatt gtggatgtgt tcattcaagc tatttaatat    5340
ctggcactgt taatacacag tactttattg tacagactgt tttactgttt taattgtagt    5400
tctgtgtact ttttttggat ggggctggca tgttttcttt gtttcctggc aatacgacgt    5460
gggaatttca atgcgttttg ttgtagatgc taacgtgtca gaatccttta cattcaactt    5520
ttctaagaaa agcattttca gtcttgtagt gtgtgcttac agtaactaat tttgttgaaa    5580
atggtttcaa gttattcaaa tttgtacagg actgtaaaga tttgttgaca gcaaaatgtt    5640
gaagaaaaaa gcttatagaa taaaagctat aagtatata ttaggatctg caaacaatga    5700
agaattatgt aatatattgt acaaatgtaa agcaaaggct ttgaaataaa atgccattgt    5760
ttgtgaatcc ttaaaaaaaa aaaaaaaaaa aaaaaaaaaa aaaa                     5804
```

<210> SEQ ID NO 16
<211> LENGTH: 1226
<212> TYPE: PRT
<213> ORGANISM: Homo sapiens

<400> SEQUENCE: 16

```
Met Lys Ala Leu Asp Glu Pro Pro Tyr Leu Thr Val Gly Thr Asp Val
  1               5                  10                  15

Ser Ala Lys Tyr Arg Gly Ala Phe Cys Glu Ala Lys Ile Lys Thr Ala
             20                  25                  30

Lys Arg Leu Val Lys Val Lys Val Thr Phe Arg His Asp Ser Ser Thr
         35                  40                  45

Val Glu Val Gln Asp Asp His Ile Lys Gly Pro Leu Lys Val Gly Ala
     50                  55                  60

Ile Val Glu Val Lys Asn Leu Asp Gly Ala Tyr Gln Glu Ala Val Ile
 65                  70                  75                  80

Asn Lys Leu Thr Asp Ala Ser Trp Tyr Thr Val Phe Asp Asp Gly
             85                  90                  95

Asp Glu Lys Thr Leu Arg Arg Ser Ser Leu Cys Leu Lys Gly Glu Arg
            100                 105                 110

His Phe Ala Glu Ser Glu Thr Leu Asp Gln Leu Pro Leu Thr Asn Pro
        115                 120                 125

Glu His Phe Gly Thr Pro Val Ile Gly Lys Lys Thr Asn Arg Gly Arg
    130                 135                 140

Arg Ser Asn His Ile Pro Glu Glu Ser Ser Ser Ser Ser Ser Ser Asp
145                 150                 155                 160

Glu Asp Glu Asp Asp Arg Lys Gln Ile Asp Glu Leu Leu Gly Lys Val
                165                 170                 175

Val Cys Val Asp Tyr Ile Ser Leu Asp Lys Lys Ala Leu Trp Phe
            180                 185                 190

Pro Ala Leu Val Val Cys Pro Asp Cys Ser Asp Glu Ile Ala Val Lys
        195                 200                 205

Lys Asp Asn Ile Leu Val Arg Ser Phe Lys Asp Gly Lys Phe Thr Ser
    210                 215                 220

Val Pro Arg Lys Asp Val His Glu Ile Thr Ser Asp Thr Ala Pro Lys
```

-continued

```
             225                 230                 235                 240
Pro Asp Ala Val Leu Lys Gln Ala Phe Glu Gln Ala Leu Glu Phe His
                 245                 250                 255
Lys Ser Arg Thr Ile Pro Ala Asn Trp Lys Thr Glu Leu Lys Glu Asp
                 260                 265                 270
Ser Ser Ser Glu Ala Glu Glu Glu Glu Glu Glu Asp Asp Glu
             275                 280                 285
Lys Glu Lys Glu Asp Asn Ser Ser Glu Glu Glu Glu Ile Glu Pro
             290                 295                 300
Phe Pro Glu Glu Arg Glu Asn Phe Leu Gln Gln Leu Tyr Lys Phe Met
305                 310                 315                 320
Glu Asp Arg Gly Thr Pro Ile Asn Lys Gln Pro Val Leu Gly Tyr Arg
                 325                 330                 335
Asn Leu Asn Leu Phe Lys Leu Phe Arg Leu Val His Lys Leu Gly Gly
                 340                 345                 350
Phe Asp Asn Ile Glu Ser Gly Ala Val Trp Lys Gln Val Tyr Gln Asp
                 355                 360                 365
Leu Gly Ile Pro Val Leu Asn Ser Ala Ala Gly Tyr Asn Val Lys Cys
             370                 375                 380
Ala Tyr Lys Lys Tyr Leu Tyr Gly Phe Glu Glu Tyr Cys Arg Ser Ala
385                 390                 395                 400
Asn Ile Glu Phe Gln Met Ala Leu Pro Glu Lys Val Val Asn Lys Gln
                 405                 410                 415
Cys Lys Glu Cys Glu Asn Val Lys Glu Ile Lys Val Lys Glu Glu Asn
                 420                 425                 430
Glu Thr Glu Ile Lys Glu Ile Lys Met Glu Glu Arg Asn Ile Ile
             435                 440                 445
Pro Arg Glu Glu Lys Pro Ile Glu Asp Glu Ile Glu Arg Lys Glu Asn
             450                 455                 460
Ile Lys Pro Ser Leu Gly Ser Lys Lys Asn Leu Glu Ser Ile Pro
465                 470                 475                 480
Thr His Ser Asp Gln Glu Lys Glu Val Asn Ile Lys Lys Pro Glu Asp
                 485                 490                 495
Asn Glu Asn Leu Asp Asp Lys Asp Asp Asp Thr Thr Arg Val Asp Glu
                 500                 505                 510
Ser Leu Asn Ile Lys Val Glu Ala Glu Glu Lys Ala Lys Ser Gly
             515                 520                 525
Tyr Asp Glu Trp Ile Lys Ala Asp Lys Ile Val Arg Pro Ala Asp Lys
             530                 535                 540
Asn Val Pro Lys Ile Lys His Arg Lys Lys Ile Lys Asn Lys Leu Asp
545                 550                 555                 560
Lys Glu Lys Asp Lys Asp Glu Lys Tyr Ser Pro Lys Asn Cys Lys Leu
                 565                 570                 575
Arg Arg Leu Ser Lys Pro Pro Phe Gln Thr Asn Pro Ser Pro Glu Met
             580                 585                 590
Val Ser Lys Leu Asp Leu Thr Asp Ala Lys Asn Ser Asp Thr Ala His
             595                 600                 605
Ile Lys Ser Ile Glu Ile Thr Ser Ile Leu Asn Gly Leu Gln Ala Ser
             610                 615                 620
Glu Ser Ser Ala Glu Asp Ser Glu Gln Glu Asp Glu Arg Gly Ala Gln
625                 630                 635                 640
Asp Met Asp Asn Asn Gly Lys Glu Glu Ser Lys Ile Asp His Leu Thr
                 645                 650                 655
```

-continued

Asn Asn Arg Asn Asp Leu Ile Ser Lys Glu Glu Gln Asn Ser Ser Ser
            660                 665                 670

Leu Leu Glu Glu Asn Lys Val His Ala Asp Leu Val Ile Ser Lys Pro
        675                 680                 685

Val Ser Lys Ser Pro Glu Arg Leu Arg Lys Asp Ile Glu Val Leu Ser
    690                 695                 700

Glu Asp Thr Asp Tyr Glu Glu Asp Glu Val Thr Lys Lys Arg Lys Asp
705                 710                 715                 720

Val Lys Lys Asp Thr Thr Asp Lys Ser Lys Pro Gln Ile Lys Arg
                725                 730                 735

Gly Lys Arg Arg Tyr Cys Asn Thr Glu Glu Cys Leu Lys Thr Gly Ser
                740                 745                 750

Pro Gly Lys Lys Glu Glu Lys Ala Lys Asn Lys Glu Ser Leu Cys Met
            755                 760                 765

Glu Asn Ser Ser Asn Ser Ser Ser Asp Glu Asp Glu Glu Thr Lys
        770                 775                 780

Ala Lys Met Thr Pro Thr Lys Lys Tyr Asn Gly Leu Glu Glu Lys Arg
785                 790                 795                 800

Lys Ser Leu Arg Thr Thr Gly Phe Tyr Ser Gly Phe Ser Glu Val Ala
                805                 810                 815

Glu Lys Arg Ile Lys Leu Leu Asn Asn Ser Asp Glu Arg Leu Gln Asn
            820                 825                 830

Ser Arg Ala Lys Asp Arg Lys Asp Val Trp Ser Ser Ile Gln Gly Gln
        835                 840                 845

Trp Pro Lys Lys Thr Leu Lys Glu Leu Phe Ser Asp Ser Asp Thr Glu
    850                 855                 860

Ala Ala Ala Ser Pro Pro His Pro Ala Pro Glu Gly Val Ala Glu
865                 870                 875                 880

Glu Ser Leu Gln Thr Val Ala Glu Glu Ser Cys Ser Pro Ser Val
                885                 890                 895

Glu Leu Glu Lys Pro Pro Pro Val Asn Val Asp Ser Lys Pro Ile Glu
            900                 905                 910

Glu Glu Thr Val Glu Val Asn Asp Arg Lys Ala Glu Phe Pro Ser Ser
        915                 920                 925

Gly Ser Asn Ser Val Leu Asn Thr Pro Thr Thr Pro Glu Ser Pro
    930                 935                 940

Ser Ser Val Thr Val Thr Glu Gly Ser Arg Gln Gln Ser Ser Val Thr
945                 950                 955                 960

Val Ser Glu Pro Leu Ala Pro Asn Gln Glu Glu Val Arg Ser Ile Lys
                965                 970                 975

Ser Glu Thr Asp Ser Thr Ile Glu Val Asp Ser Val Ala Gly Glu Leu
            980                 985                 990

Gln Asp Leu Gln Ser Gly Asn Ser Pro Ala Gly Phe Asp Ala
        995                 1000                1005

Ser Val Ser Ser Ser Ser Asn Gln Pro Glu Pro Glu His Pro Glu
    1010                1015                1020

Lys Ala Cys Thr Gly Gln Lys Arg Val Lys Asp Ala Gln Gly Gly Gly
1025                1030                1035                1040

Ser Ser Ser Lys Lys Gln Lys Arg Ser His Lys Ala Thr Val Val Asn
                1045                1050                1055

Asn Lys Lys Lys Gly Lys Gly Thr Asn Ser Ser Asp Ser Glu Glu Leu
            1060                1065                1070

-continued

```
Ser Ala Gly Glu Ser Ile Thr Lys Ser Gln Pro Val Lys Ser Val Ser
    1075                1080                1085
Thr Gly Met Lys Ser His Ser Thr Lys Ser Pro Ala Arg Thr Gln Ser
    1090                1095                1100
Pro Gly Lys Cys Gly Lys Asn Gly Asp Lys Asp Pro Asp Leu Lys Glu
1105                1110                1115                1120
Pro Ser Asn Arg Leu Pro Lys Val Tyr Lys Trp Ser Phe Gln Met Ser
                1125                1130                1135
Asp Leu Glu Asn Met Thr Ser Ala Glu Arg Ile Thr Ile Leu Gln Glu
            1140                1145                1150
Lys Leu Gln Glu Ile Arg Lys His Tyr Leu Ser Leu Lys Ser Glu Val
        1155                1160                1165
Ala Ser Ile Asp Arg Arg Arg Lys Arg Leu Lys Lys Lys Glu Arg Glu
    1170                1175                1180
Ser Ala Ala Thr Ser Ser Ser Ser Ser Pro Ser Ser Ser Ser Ser Ile
1185                1190                1195                1200
Thr Ala Ala Ala Met Leu Thr Leu Ala Glu Pro Ser Met Ser Ser Ala
                1205                1210                1215
Ser Gln Asn Gly Met Ser Val Glu Cys Arg
            1220                1225
```

<210> SEQ ID NO 17
<211> LENGTH: 23
<212> TYPE: DNA
<213> ORGANISM: Homo sapiens

<400> SEQUENCE: 17
tgacggatcc tgcggccgca aag                                    23

<210> SEQ ID NO 18
<211> LENGTH: 27
<212> TYPE: DNA
<213> ORGANISM: Homo sapiens

<400> SEQUENCE: 18
tctggaattc cttcccagag agagggc                                27

<210> SEQ ID NO 19
<211> LENGTH: 25
<212> TYPE: DNA
<213> ORGANISM: Homo sapiens

<400> SEQUENCE: 19
tctggaattc attcttttta cttcc                                  25

<210> SEQ ID NO 20
<211> LENGTH: 29
<212> TYPE: DNA
<213> ORGANISM: Homo sapiens

<400> SEQUENCE: 20
tctggaattc cctgatcaga atgtgtagg                              29

<210> SEQ ID NO 21
<211> LENGTH: 30
<212> TYPE: DNA
<213> ORGANISM: Homo sapiens

<400> SEQUENCE: 21
tctggaattc cccagatttt cattgtcttc                             30

<210> SEQ ID NO 22
<211> LENGTH: 27
<212> TYPE: DNA
<213> ORGANISM: Homo sapiens

<400> SEQUENCE: 22
tctggaattc cctaccctag ttgtgtc                                27

<210> SEQ ID NO 23
<211> LENGTH: 27
<212> TYPE: DNA
<213> ORGANISM: Homo sapiens

<400> SEQUENCE: 23
tctggaattc gctttaatcc attcatc                                27

<210> SEQ ID NO 24
<211> LENGTH: 27
<212> TYPE: DNA
<213> ORGANISM: Homo sapiens

<400> SEQUENCE: 24
tctggaattc gcttttctt cctcagc                                 27

<210> SEQ ID NO 25
<211> LENGTH: 10
<212> TYPE: PRT
<213> ORGANISM: Homo sapiens

<400> SEQUENCE: 25

Ile Lys Pro Ser Leu Gly Ser Lys Lys Asn
 1               5                  10

<210> SEQ ID NO 26
<211> LENGTH: 9
<212> TYPE: PRT
<213> ORGANISM: Homo sapiens

<400> SEQUENCE: 26

Lys Pro Ser Leu Gly Ser Lys Lys Asn
 1               5

<210> SEQ ID NO 27
<211> LENGTH: 8
<212> TYPE: PRT
<213> ORGANISM: Homo sapiens

<400> SEQUENCE: 27

Ile Lys Pro Ser Leu Gly Ser Lys
 1               5

<210> SEQ ID NO 28
<211> LENGTH: 7
<212> TYPE: PRT
<213> ORGANISM: Homo sapiens

<400> SEQUENCE: 28

Lys Pro Ser Leu Gly Ser Lys
 1               5

<210> SEQ ID NO 29
<211> LENGTH: 7
<212> TYPE: PRT

```
<213> ORGANISM: Homo sapiens

<400> SEQUENCE: 29

Pro Ser Leu Gly Ser Lys Lys
 1               5

<210> SEQ ID NO 30
<211> LENGTH: 7
<212> TYPE: PRT
<213> ORGANISM: Homo sapiens

<400> SEQUENCE: 30

Ile Lys Pro Ser Leu Gly Ser
 1               5

<210> SEQ ID NO 31
<211> LENGTH: 7
<212> TYPE: PRT
<213> ORGANISM: Homo sapiens

<400> SEQUENCE: 31

Ser Leu Gly Ser Lys Lys Asn
 1               5

<210> SEQ ID NO 32
<211> LENGTH: 8
<212> TYPE: PRT
<213> ORGANISM: Homo sapiens

<400> SEQUENCE: 32

Lys Pro Ser Leu Gly Ser Lys Lys
 1               5

<210> SEQ ID NO 33
<211> LENGTH: 8
<212> TYPE: PRT
<213> ORGANISM: Homo sapiens

<400> SEQUENCE: 33

Pro Ser Leu Gly Ser Lys Lys Asn
 1               5
```

RBP1L1, A NOVEL RETINOBLASTOMA BINDING PROTEIN-RELATED GENE ENCODING AN ANTIGENIC EPITOPE AND METHODS OF USING THEREOF

CROSS REFERENCE TO RELATED APPLICATIONS

This application claims the benefit of U.S. Provisional Patent Application No. 60/275,518 filed 14 Mar. 2001, which names Jia-ning Cao as the inventor and is herein incorporated by reference in its entirety.

STATEMENT REGARDING FEDERALLY SPONSORED RESEARCH OR DEVELOPMENT

This invention was made with Government support under Grant Nos. CA 12582, CA 56059, and CA 13579 awarded by National Institutes of Health/National Cancer Institute.

BACKGROUND OF THE INVENTION

1. Field of the Invention

This invention relates generally to methods of detecting or diagnosing a plurality of different cancers. In particular, the present invention relates to a retinoblastoma binding protein-related gene that is differentially expressed in cancer cells as compared to normal cells.

2. Description of the Related Art

Breast, lung, colon, pancreas, and ovarian cancers are aggressive forms of cancer, difficult to diagnose, or both. In order to detect breast cancer by physical examination, a breast tumor must be of a large enough size and mammography is limited by the skill of the observer, the quality of the mammogram, often result in over 80% false positives and over 10% false negatives. See Wright, et al. (1995) Lancet 346:29-32. Generally, there are no observable clinical symptoms of lung cancer until the advanced stage. In fact, only 16% of lung cancers are discovered before the disease has spread. Likewise, colon cancer is difficult to diagnose as clinical symptoms such as rectal bleeding, pain, abdominal distension, or weight loss are observable only after the disease is advanced and not surgically curable. Fecal occult blood tests are difficult to conduct due to lack of compliance, are poorly sensitive, exhibit little predicative value, and often lead to colonoscopic examination which is an expensive and invasive procedure. Pancreatic cancer produces few specific symptoms in its early stages and usually is detected at an advanced and incurable stage. Thus, pancreatic cancer exhibits the lowest survival rate of any major cancer. Specifically, the average survival after diagnosis is less than 6 months and fewer than 5% of patients survive 5 years. See Rosenberg, L. (1997) Pancreatol. 22:81-93; and Flanders and Foulkes (1996) J. Med. Genet. 33:889-898). Likewise, ovarian cancer is difficult to diagnose and effective treatment depends on early detection.

Molecular identification of tumor antigens that can elicit both antibody and cellular immune responses in humans has been an important focus in the development of therapeutic methods that are active and specific against various cancers and tumors. Many strategies have been used to characterize and detect tumor antigens. See e.g. DePlaen et al. (1988) PNAS USA 85:2275-2280; Mandelboim, et al. (1994) Nature 369:69; and Sahin, et al. (1995) PNAS USA 92:11810-11913.

Numerous human tumor antigens have been identified. See e.g., Van der Bruggen, et al. (1991) Science 254:1643-1647 (MAGE-1); Brichard, et al. (1993) J. Exp. Med. 178:489-495; Coulie, et al. (1994) J. Exp. Med. 180:35-42; Kawakami, et al. (1994) PNAS USA 91:3515-3519; Clark, et al. (1994) Nature Genetics 7:502-508 (SSX-2); Crew, et al. (1995) EMBO J. 144:2333-2340 (SSX-1); DeLeeuw, et al. (1996) Cytogenet. Genet. 73:179-183 (SSX-3); Gure, et al. (1997) Int. J. Cancer, 72:965-971 (SSX4); Meuwissen, et al. (1992) EMBO J. 11(13):5091-5100 (SCP-1); Tureci, et al. (1996) Cancer Res. 56:4766-4772 (HOM-MEL-40); Chen, et al. (1997) PNAS USA 94:1914-1918 (NY-ESO-1); Boel, et al. (1995) Immunity 2:167-175 (BAGE); and U.S. Pat. Nos. 5,610,013 and 5,648,226 (GAGE). Many of these tumor antigens have been the focus of cancer immunotherapy. Unfortunately, for a variety of reasons, many of the tumor antigens known in the art are not useful in cancer immunotherapy.

Thus, a need still exists for effective and accurate cancer diagnostics and therapies.

SUMMARY OF THE INVENTION

The present invention generally relates to a retinoblastoma binding protein-related gene encoding an antigenic epitope and methods of using thereof.

In some embodiments, the present invention relates to a retinoblastoma binding protein-related gene that encodes a polypeptide comprising SEQ ID NO:3 or a variant thereof. The variant may specifically bind to an antibody raised against the polypeptide comprising SEQ ID NO:3 or an antibody obtained from a subject having cancer, such as breast, lung, colon, pancreas, or ovarian cancer. In some embodiments, the polynucleotide comprises a SEQ ID NO:1 or a fragment or variant thereof. In other embodiments, the polynucleotide consists of SEQ ID NO:1 or a fragment thereof. In some embodiments, the polypeptide comprises SEQ ID NO:2 or a fragment or variant thereof. In other embodiments, the polypeptide consists of SEQ ID NO:2 or SEQ ID NO:3. In some embodiments, the polynucleotide sequence is at least about 80% identical to SEQ ID NO:1. In some embodiments, the polynucleotide sequence is at least about 90% identical to SEQ ID NO:1. In some embodiments, the polypeptide is at least about 80% identical to SEQ ID NO:2 or SEQ ID NO:3. In some embodiments, the polypeptide is at least about 90% identical to SEQ ID NO:2 or SEQ ID NO:3.

In some embodiments, the present invention relates to a polypeptide encoded by the polynucleotide of the present invention. In some embodiments, the polypeptide comprises SEQ ID NO:2 or SEQ ID NO:3. In other embodiments, the polypeptide consists of SEQ ID NO:2 or SEQ ID NO:3. In some embodiments, the polypeptide is at least about 80% identical to SEQ ID NO:2 or SEQ ID NO:3. In some embodiments, the polypeptide is at least about 90% identical to SEQ ID NO:2 or SEQ ID NO:3.

In some embodiments, the present invention relates to a vector comprising a polynucleotide of the present invention.

In some embodiments, the present invention relates to a host comprising a polynucleotide of the present invention.

In some embodiments, the present invention relates to a fusion protein comprising a polypeptide of the present invention.

In some embodiments, the present invention relates to an antibody or fragment thereof that specifically binds a polypeptide of the present invention. In some embodiments, the antibody was raised against a polypeptide comprising SEQ ID NO:2 or SEQ ID NO:3.

In some embodiments, the present invention relates to a pharmaceutical composition comprising a polypeptide or an antibody or fragment of the present invention and a pharmaceutically acceptable vehicle.

In some embodiments, the present invention relates to an immunogenic composition comprising a polypeptide of the present invention.

In some embodiments, the present invention relates to a vaccine comprising a polypeptide of the present invention. In preferred embodiments, the vaccine is effective for treating or preventing cancer, such as breast, lung, colon, pancreas, or ovarian cancer.

In some embodiments, the present invention relates to a method of inducing an immune response against a cancer or a tumor in a subject which comprises administering to the subject at least one polypeptide of the present invention. The cancer may be breast, lung, colon, pancreas, or ovarian cancer.

In some embodiments, the present invention relates to a method of treating, preventing, or inhibiting a cancer or a tumor in a subject which comprises administering to the subject at least one polypeptide of the present invention, at least one antibody raised against a polypeptide of the present invention, or both. In preferred embodiments, the cancer is breast, lung, colon, pancreas, or ovarian cancer.

In some embodiments, the present invention relates to a marker for diagnosing a cancer or susceptibility of obtaining the cancer in a subject comprising a polynucleotide of the present invention. In preferred embodiments, the cancer is breast, lung, colon, pancreas, or ovarian cancer.

In some embodiments, the present invention relates to a marker for diagnosing a cancer or susceptibility of obtaining the cancer in a subject comprising a polypeptide of the present invention.

In some embodiments, the present invention relates to a method for detecting the presence of a cancer in a subject which comprises obtaining a biological sample from the subject; contacting the biological sample with a binding agent that binds to a polypeptide of the present invention; detecting in the sample an amount of polypeptide that binds to the binding agent; and comparing the amount of polypeptide to a control and therefrom determining the presence of a cancer in the subject.

In some embodiments, the present invention relates to a method for detecting the presence of a cancer in a subject which comprises obtaining a biological sample from the patient; contacting the biological sample with a polynucleotide of the present invention; detecting in the sample an amount of a second polynucleotide that hybridizes to the polynucleotide; and comparing the amount of the second polynucleotide that hybridizes to the polynucleotide to a control, and therefrom determining the presence of the cancer in the patient.

In some embodiments, the present invention relates to a diagnostic kit comprising at least one reagent selection from the group consisting of: a polynucleotide that encodes a polypeptide comprising SEQ ID NO:3 or a variant thereof; the polypeptide comprising SEQ ID NO:3 or a variant thereof; a polypeptide comprising SEQ ID NO:2 or a fragment or variant thereof; or an antibody that specifically binds the polypeptide of the present invention; and instructions for use.

In some embodiments, the present invention relates to a method for inhibiting the development of a cancer in a subject which comprises incubating CD4$^+$ T cells, CD8$^+$ T cells, or both with at least one component selected from the group consisting of: at least one polynucleotide that encodes a polypeptide comprising SEQ ID NO:3 or a variant thereof; the polypeptide comprising SEQ ID NO:3 or a variant thereof; at least one polypeptide comprising SEQ ID NO:2 or a fragment or variant thereof; and antigen presenting cells that express the polypeptide of the present invention, such that T cell proliferate; and administering to the subject an effective amount of the proliferated T cells, and thereby inhibiting the development of a cancer in the subject.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 11B illustrates the expression of immunopositive fusion proteins in *Escherichia coli* and is depicted in sodium dodecyl sulfate-polyacrylamide gel electrophoresis followed by Western blot analysis with the purified human IgG. Lane a=lysate of isopropyl β-D-thiogalactopyranoside (IPTG)-induced lysogen from clone 131; lane b=lysate of IPTG-induced lysogen from clone 151. The band at 128 kDa represents the fusion protein containing a 107-amino acid insert. Molecular mass markers (kDa) are indicated to the right.

FIG. 2 shows the complete nucleotide sequence (SEQ ID NO:1) and deduced amino acid sequence of RBP1L1 gene (SEQ ID NO:2). The amino acids in the epitope are underlined (SEQ ID NO:3).

FIG. 3 is an alignment of the sequences of the RBP1L1 protein and the RBP1 protein (SEQ ID NO:4). The dotted line indicates absent sequence. The amino acids in the epitopes are underlined.

DETAILED DESCRIPTION OF THE INVENTION

Figure 1:
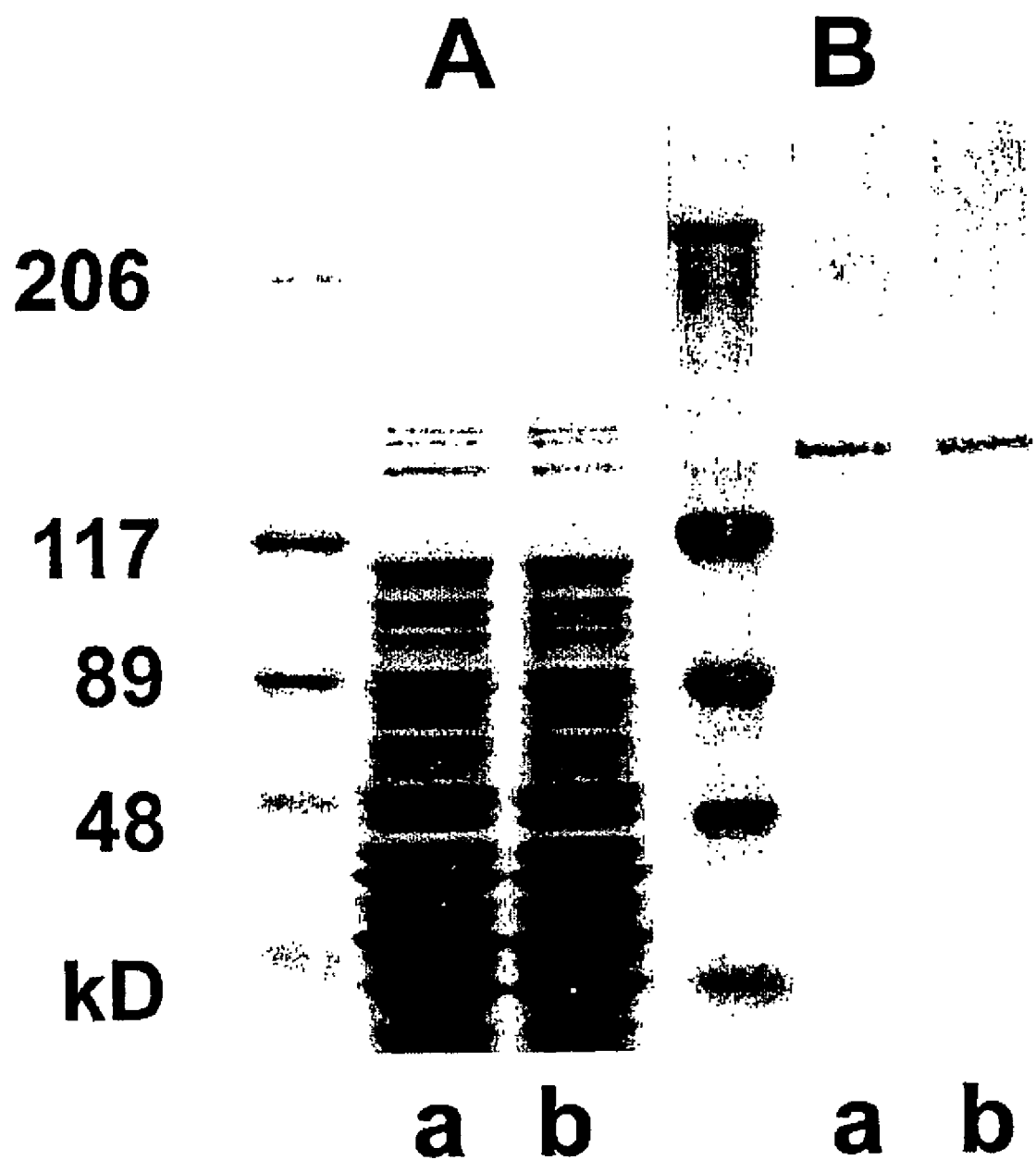
FIG. 1A illustrates the expression of immunopositive fusion proteins in *Escherichia coli* and is depicted in sodium dodecyl sulfate-polyacrylamide gel electrophoresis followed by Coomassie brilliant blue staining. Lane a=lysate of isopropyl β-D-thiogalactopyranoside (IPTG)-induced lysogen from clone 131; lane b=lysate of IPTG-induced lysogen from clone 151. The band at 128 kDa represents the fusion protein containing a 107-amino acid insert. Molecular mass markers (kDa) are indicated to the right.

The present invention provides a retinoblastoma-binding protein-1-like protein-1 (RBP1L1), a novel polypeptide that is differentially expressed in breast, lung, colon, pancreas, and ovarian cancer cells as compared to normal cells.

"RBP1L1" denotes a polypeptide encoded by a retinoblastoma-binding protein-1-like protein-1 gene having a polynucleotide sequence (1) set forth in SEQ ID NO:1, (2) has substantial identity to the sequence set forth in SEQ ID NO:1, (3) that encodes the polypeptide of SEQ ID NO:2 or SEQ ID NO:3, (4) that encodes a polypeptide having substantial identity to the sequence of SEQ ID NO:2 or SEQ ID NO:3, and (5) variants thereof. RBP1L1 is differentially expressed in cancer cells, such as breast, lung, colon, pancreas, and ovarian cancer cells, at a level that is greater than the level of expression in a normal tissue, as determined by conventional methods known in the art. RBP1L1 may be obtained from any species, particularly mammalian, including bovine, ovine, porcine, murine, equine, and preferably human, from any source whether natural, synthetic, semi-synthetic, or recombinant.

In a previous study, a tumor-associated antigen corresponding to the retinoblastoma binding protein-1 (RBP1) was identified by using an allogeneic IgG antibody prepared from the serum of a patient with breast cancer to screen a complementary DNA (cDNA) expression library of MCF-7 breast cancer cells. See Cao, J, et al. (1999) Breast Cancer Res. Treat. 53:279-290, which is herein incorporated by reference. Although the RBP1 gene was present in normal human cells, as well as cancer cells, expression of the antigenic epitope was restricted to certain types of cancer, such as breast, prostate, and renal cancers. See Fattaey, A. R., et al. (1993) Oncogene 8:3149-3146, which is herein incorporated by reference.

In humans, RBP1 contains a heptameric antibody-binding peptide epitope, KASIFLK (SEQ ID NO:5), corresponding to RBP1 amino acids 250-256 and two overlapping decameric peptide epitopes, GLQKASIFLK (SEQ ID NO:6) and KASIFLKTRV (SEQ ID NO:7), corresponding to RBP1 amino acids 247-256 and 250-259, respectively. These epitopes were highly immunogenic and induced both specific antibody and cytotoxic T-lymphocyte (CTL) responses. CTL responses induced by the decameric peptide epitopes exhibited strong cytotoxic activity against HLA-A2- and HLA-A3-positive breast cancer cells. See Takahashi, T., et al. (1999) Br. J. Cancer 81:342-349, which is herein incorporated by reference. The investigation of the KASIFLK epitope (SEQ ID NO:5) led to the discovery of the present invention—the RBP1L1 polynucleotide that encodes a polypeptide comprising an antigenic nonameric peptide epitope, IKPSLGSKK (SEQ ID NO:3).

As disclosed herein, the RBP1L1 gene was isolated from a MCF-7 cDNA expression library screened with purified human IgG from a patient with breast cancer. The complete 5802 bp RBP1L1 cDNA encodes a 1226 amino acid polypeptide comprising the epitope, IKPSLGSKK (SEQ ID NO:3). The polypeptide sequence of RBP1L1 shares 74% amino acid identity with that of the partial cDNA sequence of the retinoblastoma-binding protein and 37% identity with retinoblastoma binding protein-1 (RBP1), which reportedly suppress cell growth by interacting with the retinoblastoma family members and histone deacetylases to repress transcriptional activity.

Little or no expression of RBP1L1 transcripts was detected in normal adult pancreas, prostate, ovary, adrenal medulla, thyroid, adrenal cortex, spleen, thymus, colon, stomach, and peripheral blood mononuclear cells (PBMCs), although expression was detected in normal testis. Consistent with this observation, RT-PCR analysis of normal tissues did not detect RBP1L1 mRNA, except in testis. However, in human breast, lung, colon, ovaries, and pancreas cancers, high levels of RBP1L1 mRNA were detected. Thus, RBP1L1 mRNA is expressed abundantly in cancer cells and in normal testicular cells. This restricted pattern of expression or differential expression pattern may be used to diagnose a broad range of human cancers.

As provided in the Examples below, purified human IgG from an individual having breast cancer binds to a nonameric peptide antigen, IKPSLGSKK (SEQ ID NO:3), encoded by the RBP1L1 polypeptide. Immunohistochemical and cytological studies with this antibody reveal that the antigen is located in the cytoplasm. Because of the extensive sequence conservation between RBP1L1 and RBP1 (64% identity in the N-terminal 450 amino acids and 42% identity in C-terminal 300 amino acids) it is likely that the functional pathway of RBP1L1 in part mirrors that of RBP1. Like RBP1, RBP1L1 also comprises an ARID and a BRIGHT DNA binding domain. Both antigens, IKPSLGSKK (SEQ ID NO:3) and KASIFLK (SEQ ID NO:5) are over-expressed in human cancer cells that are detected by human antibodies. The cellular localization of both antigens is localized to present mainly in the cytoplasm of cancer cells.

Previous studies show that serologically identified antigens are recognized by HLA class I-restricted CTLs and can induce antibody responses in subjects with tumors. See Morioka, N., et al. (1994) J. Immunol. 153:5650-5658; Takahashi, T., et al. (1997) Cell Immunol. 178:162-171; and Chen, Y. T., et al. (1997) PNAS USA 94:1914-1918, which are herein incorporated by reference. Since the antigenic peptide KASIFLK (RBP1 amino acids 250-256) (SEQ ID NO:5) is serologically similar to the antigenic peptide of the present invention, IKPSLGSKK (SEQ ID NO:3), it is expected that in vitro stimulation of HLA-A2- and HLA-A3-positive PBMCs with peptides comprising the IKPSLGSKK antigen (SEQ ID NO:3) will generate peptide-specific CTLs that are highly cytotoxic to HLA-A2- and HLA-A3-positive cancer cells but not to normal cells. See Chen, J. L., et al. (2000) J. Immunol. 165:948-955; and Takahashi, T., et al. (1999) Br. J. Cancer 81:342-349, which are herein incorporated by reference. Therefore, the IKPSLGSKK antigenic epitope (SEQ ID NO:3) of the present invention may be used as a target for cancer cell destruction via a dual-effector immune system.

Since MAGE, TRP-2, and gp100 tumor-associated antigens have been shown to elicit strong antibody responses to their respective recombinant antigens in melanoma patients immunized with an antigen-containing melanoma cell vaccine, the present invention provides an antigenic epitope, IKPSLGSKK (SEQ ID NO:3), which may be used in immunotherapies for treating cancer.

Because of the protein sequence identity and similar immunological features between RBP1L1 and RBP1, RBP1L1 may associate with the pRB-pocket and regulate the transcription of genes that control the cell cycle, differentiation, proliferation, and apoptosis. Specifically, since (1) RBP1 binds to the pocket of pRB, (2) RBP1 represses transcriptional activity by interacting with p130-E2F and pRB-E2F complexes during cell cycle arrest, (3) RBP1 represses E2F-dependent transcription by recruitment of histone deacetylases complex, and (4) over-expression of RBP1 inhibits E2F-dependent gene expression and suppresses cell growth (Lai, A., et al. (1999) Oncogene 18:2091-2100; Dyson, N. (1998) Genes Dev. 12:2245-2262; and Lai, A., et al. (2001) Mol. Cell. Biol. 21(8):2918-2932), RBP1L1 may also bind the pocket of pRB, repress transcriptional activity, or affect the cell cycle and growth of a cell, or a combination thereof.

Genes with high mRNA expression in human testis and tumor cells are not unique and mRNAs of many of the genes for human cancer-associated antigens, identified by using human antibodies to screen recombinant cDNA expression libraries, are also overexpressed in the testis. See Chen, Y. T., et al. (1997) PNAS USA 94:1914-1918; Van der Bruggen, P., et al. (1991) Science 254:1643-1647; and Gure, A. O., et al. (2000) Int. J. Cancer 85:726-732, which are herein incorporated by reference. The present invention provides the first retinoblastoma binding-related protein gene that encodes a cancer-associated antigen and is highly expressed by various cancer types (and normal testicular cells). The RBP1L1 polynucleotide sequence shows no homology to any reported cancer/testis genes.

The high expression of RBP1L1 in normal testicular cells, does not diminish the use of RBP1L1 in immunotherapy because the testis is an immunologically privileged site. Thus, the testicular cells expressing the tumor antigen will escape direct contact by antigen-presenting cells, and CTLs and antibody responses induced by peptide antigens derived from cancer/testis antigen genes may attack autologous cancer cells without killing normal testicular cells. The lack of HLA class I expression on the surface of testicular cells also favors their ability to escape from CTL recognition and killing. Thus, the present invention provides methods of using the antigenic epitope, IKPSLGSKK (SEQ ID NO:3), or a peptide containing this epitope, in cancer and tumor immunotherapy.

The present invention is generally directed to compositions and methods for using the compositions in the diagnosis and treatment of cancer, such as breast, lung, colon, pancreas, and ovarian cancer. The compositions of the present invention include RBP1L1 polypeptides, polynucleotides encoding such polypeptides, binding agents such as antibodies, antigen presenting cells (APCs), immune system cells (e.g., T cells), and combinations thereof.

The present invention provides RBP1L1 polynucleotides and variants thereof. In preferred embodiments the polynucleotides are isolated. As used herein, "isolated" polynucleotide refers to a DNA molecule that is isolated from its native environment. An "isolated" polynucleotide may be substantially isolated away from, or purified free from, total genomic DNA of the species from which the DNA segment is obtained. An "isolated" polynucleotide may include a DNA segment that is separated from other DNA segments with which is normally or natively associated at either the 5' end, 3' end, or both. An "isolated" polynucleotide may include a DNA segment that is substantially away from other coding sequences, and does not contain large portions of unrelated coding DNA, such as large chromosomal fragments or other functional genes or polypeptide coding regions. "Nucleic acid sequence", "nucleic acid molecule", and "polynucleotide" are used interchangeably to refer to an oligonucleotide, nucleotide, or polynucleotide, and fragments or portions thereof, and to DNA or RNA of genomic or synthetic origin and may be single- or double-stranded, and represent the sense or antisense strand.

The polynucleotides of the present invention may include genomic sequences, extra-genomic and plasmid-encoded sequences and smaller engineered gene segments that express, or may be adapted to express, proteins, polypeptides, peptides, and the like. The polynucleotides of the present invention may be in its native form or synthetically modified. The polynucleotides of the present invention may be single-stranded (coding or antisense) or double-stranded, and may be DNA (genomic, cDNA or synthetic) or RNA molecules. RNA molecules include mRNA molecules, which contain introns and correspond to a DNA molecule in a one-to-one manner, and mRNA molecules, which do not contain introns. Additional coding or non-coding sequences may be present within a polynucleotide of the present invention, and a polynucleotide may be linked to other molecules, support materials, or both.

The polynucleotides of the present invention may comprise a native sequence, i.e., an endogenous sequence that encodes the RBP1L1 polypeptide or a portion thereof, or may comprise a variant or a biological or antigenic functional equivalent thereof. Polynucleotide variants may contain one or more substitutions, additions, deletions, insertions, or combinations thereof so long as the biological activity, such as immunogenicity, of the encoded polypeptide is not diminished, relative to the RBP1L1 polypeptide. A "variant" of a polynucleotide refers to the chemical modification of a nucleic acid encoding RBP1L1 or the encoded RBP1L1. Illustrative of such modifications would be replacement of hydrogen by an alkyl, acyl, or amino group. A nucleic acid variant encodes a polypeptide that retains essential biological characteristics of the natural molecule.

The term "biologically active", as used herein, refers to a polypeptide or polynucleotide having structural, regulatory, or biochemical functions of a naturally occurring molecule.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art.

As used herein, "stringent conditions" refers to the "stringency" which occurs within a range from about 5° C. below the melting temperature (Tm) of the probe to about 20° C. to about 25° C. below Tm. As will be understood by those of skill in the art, the stringency of hybridization may be altered in order to identify or detect identical or related polynucleotide sequences. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at about 50° C. to about 65° C., 5×SSC, overnight; followed by washing twice at about 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Alternatively, the polypeptides of the present invention may be made by conventional recombinant DNA techniques such as those disclosed in the Examples below. Thus, the present invention provides polynucleotides that encode the polypeptides of the present invention. In preferred embodiments, the polynucleotides are isolated.

A polynucleotide that encodes a polypeptide having substantial identity to either SEQ ID NO:2 or SEQ ID NO:3 can be made by introducing one or more nucleotide substitutions, insertions, or deletions into the nucleotide sequence that encodes SEQ ID NO:1, SEQ ID NO:2, or SEQ ID NO:3 such that one or more amino acid substitutions, insertions, or deletions are introduced into the encoded polypeptide. Mutations can be introduced by standard techniques, such as site-directed mutagenesis and PCR-mediated mutagenesis.

In other embodiments of the present invention, the polynucleotide sequences provided herein can be used as probes or primers for nucleic acid hybridization. As such, nucleic acid segments that comprise a sequence region of at least about a 15 nucleotide long contiguous sequence that has the same sequence as, or is complementary to, a 15 nucleotide long contiguous sequence disclosed herein are contemplated. Longer contiguous identical or complementary sequences up to full-length sequences are also contemplated.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotides having sequence regions consisting of contiguous nucleotide stretches of 10-14, 15-20, 30, 50, or even of 100-200 nucleotides or so (including intermediate lengths as well), identical or complementary to SEQ ID NO:1 or SEQ ID NO:15, are particularly contemplated as hybridization probes in recombinant DNA and molecular biology techniques. The total size of fragment, as well as the size of the complementary sequence, will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used.

Small polynucleotide fragments of the present invention may be readily prepared by conventional methods known in the art, for example, directly synthesizing the fragment with an automated oligonucleotide synthesizer, PCR technology, and recombinant DNA techniques.

The polynucleotides of the present invention may be identified, prepared, or manipulated by conventional methods known in the art. For example, a polynucleotide may be identified by screening a microarray of cDNAs for tumor-associated expression, i.e., differential expression as compared to the expression in normal tissue, as determined by conventional methods such as that provided in the Examples herein. See e.g. Schena et al. (1996) PNAS USA 93:10614-10619, and Heller et al. (1997) PNAS USA 94:2150-2155, which are herein incorporated by reference. Alternatively, the polynucleotides of the present invention may be amplified from cDNA prepared from cells expressing the proteins described herein, such as breast tumor cells.

Polypeptides and polypeptide fragments of the present invention comprise at least one immunogenic portion of RBP1L1 or a variant thereof. "Amino acid sequence", "amino acid molecule", "polypeptide", "protein", and "peptide", are used interchangeably to refer to an oligopeptide, peptide, polypeptide, or protein sequence, and fragments or portions thereof, and to naturally occurring or synthetic molecules.

RBP1L1 polypeptides will react with antibodies raised against a polypeptide comprising SEQ ID No: 2 or SEQ ID NO:3 and may react detectably within an immunoassay (such as an ELISA) with antisera from a patient with having breast, lung, colon, pancreas, or ovarian cancer. Polypeptides of the present invention may be of any length. Additional sequences derived from the native protein and/or heterologous sequences may be present, and such sequences may possess further immunogenic or antigenic properties.

As used herein an "immunogenic portion" is a portion of a protein that is recognized by a B-cell and/or T-cell surface antigen receptor. Such immunogenic portions include the antigenic epitope, IKPSLGSKK (SEQ ID NO:3), or variants thereof. Variants of IKPSLGSKK (SEQ ID NO:3) are polypeptides that exhibit a similar sequence homology and bioactivity (immunogenicity) to IKPSLGSKK (SEQ ID NO:3). Immunogenic portions may generally be identified using well-known techniques. See Paul, Fundamental Immunology, 3rd ed., 243-247 (Raven Press, 1993) and references cited therein, which are herein incorporated by reference. The terms "antigenic determinant" or "antigenic epitope" or "epitope" are used interchangeably to refer to a region of a molecule with the ability or potential to elicit, and combine with, an antibody or fragment thereof.

The polypeptides of the present invention need not be identical to those exemplified herein so long as the subject polypeptides are able to induce an immune response against the antigenic epitope or immunogenic portion of the present invention. Thus, as used herein "variants" of the polypeptides of the present invention refer to polypeptides having insignificant changes. "Insignificant changes" refer to modifications in the amino acid sequence of a given polypeptide that do not change the biological activity, such as the immunological activity, of the polypeptide. Such insignificant changes include a methionine as the first amino acid residue at the amino terminus, conservative amino acid substitutions, deletions, or insertions, and co-translational or post-translational surface modifications such as the addition of covalently attached sugars, lipids, or combinations thereof. "Immunologically activity" refers to the capability of the natural, recombinant, or synthetic RBP1L1, or any oligopeptide thereof, to induce a specific immune response in appropriate animals or cells and to bind with specific antibodies.

A polypeptide "variant" of the present invention also includes a polypeptide that differs from RBP1L1 (SEQ ID NO:2) by one or more substitutions, deletions, additions, insertions, or a combination thereof such that the immunogenicity of the polypeptide is not substantially diminished. For example, the ability of a variant to react with antibodies specific for IKPSLGSKK (SEQ ID NO:3) may be enhanced or unchanged, relative to the native protein, or may be diminished by less than 50%, and preferably less than 20%, relative to the native protein.

As used herein, a "variant" of RBP1L1 a polypeptide is altered by one or more amino acids. The variant may have "conservative" changes, wherein a substituted amino acid has similar structural or chemical properties, e.g. replacement of leucine with isoleucine. More rarely, a variant may have "nonconservative" changes, e.g., replacement of a glycine with a tryptophan. Similar minor variations may also include amino acid deletions, insertions, or both. Guidance in determining which amino acid residues may be substituted, inserted, or deleted without abolishing biological or immunological activity may be found using computer programs well known in the art, for example, LASERGENE software. Polypeptide variants encompassed by the present invention include those exhibiting at least about 80%, 85%, 90%, 91%, 92%, 93%, 94%, 95%, 96%, 97%, 98%, or 99% or more identity to the polypeptides disclosed herein.

The polypeptides of the present invention may also be modified to provide a variety of desired attributes, e.g., improved pharmacological characteristics, while increasing or at least retaining substantially all of the immunological activity of the antigenic epitope. By using conventional methods in the art, one of ordinary skill will be readily able to make a variety of polypeptides having substantial identity to those explicitly provided for herein, and then screen the polypeptides for stability, toxicity, and immunogenicity according to the present invention.

Additionally, single amino acid substitutions, deletions, or insertions can be used to determine which residues are relatively insensitive to modification. Amino acid substitutions are preferably made between relatively neutral moieties, such as alanine, glycine, proline, and the like. Substitutions with different amino acids, of either D or L isomeric forms, or amino acid mimetics can be made. The number and types of substitutions, deletions, and insertions depend on the functional attributes that are sought such as hydrophobicity, immunogenicity, three-dimensional structure, and the like.

An "amino acid mimetic" as used herein refers to a moiety other than a naturally occurring amino acid residue that conformationally and functionally serves as a suitable substitute for an amino acid residue in a polypeptide of the present invention. A moiety is a suitable substitute for an amino acid residue if it does not interfere with the ability of the peptide to elicit an immune response against the polypeptide of the present invention. Examples of amino acid mimetics include cyclohexylalanine, 3-cyclohexylpropionic acid, L-adamantyl alanine, adamantylacetic acid, and the like. See e.g. Morgan and Gainor, (1989) Ann. Repts. Med. Chem. 24:243-252, which is herein incorporated by reference.

Individual amino acid residues may be incorporated in the polypeptides of the present invention with peptide bonds or peptide bond mimetics. "Peptide bond mimetics" include peptide backbone modifications of the amide nitrogen, the α-carbon, amide carbonyl, complete replacement of the amide bond, extensions, deletions or backbone crosslinks. See e.g. Spatola (1983) CHEMISTRY AND BIOCHEMISTRY OF AMINO ACIDS, PEPTIDES AND PROTEINS, Vol. VII, Weinstein ed., which is herein incorporated by reference. The polypeptides of the present invention may include an additional methionine as the first amino acid residue on the protein amino terminus. The polypeptides may be truncated or contain co-translational or post-translational surface modifications, such as the addition of covalently attached sugars or lipids.

In preferred embodiments, the polypeptides of the present invention have a substantial sequence identity to the amino acid sequence set forth in SEQ ID NO:2 or SEQ ID NO:3. As used herein "sequence identity" means that two sequences are identical over a window of comparison. The percentage of sequence identity is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan).

The polypeptides of the present invention may comprise a signal or leader sequence at the N-terminal end of the polypeptide, which co-translationally or post-translationally directs transfer of the protein. The polypeptide may also be conjugated to a linker or other sequence for ease of synthesis, purification or identification of the polypeptide such as a histidine tag, or to enhance binding of the polypeptide to a solid support. For example, a polypeptide may be conjugated to an immunoglobulin Fc region.

The polypeptides of the present invention and fragments thereof may be made by conventional methods known in the art. The polypeptides of the present invention may be manually or synthetically synthesized using conventional methods and devices known in the art. See e.g., Stewart and Young (1984) SOLID PHASE PEPTIDE SYNTHESIS, 2 ed. Pierce, Rockford, Ill.; Merrifield, (1963) J. Am. Chem. Soc. 85:2149-2146, which are herein incorporated by reference. Equipment for automated synthesis of polypeptides is commercially available from suppliers such as Perkin Elmer/Applied BioSystems Division (Foster City, Calif.), and may be operated according to the manufacturer's instructions. The composition of the synthetic peptides may be confirmed by conventional methods in the art, such as amino acid analysis or sequencing.

The polypeptides of the present invention may be purified from natural sources using conventional protein purification techniques such as reverse phase high-performance liquid chromatography (HPLC), ion-exchange or immunoaffinity chromatography, filtration or size exclusion, or electrophoresis. See e.g., Scopes (1982) PROTEIN PURIFICATION, Springer-Verlag, N.Y., which is herein incorporated by reference.

In some embodiments, the polypeptides of the present invention may be substantially purified. As used herein, a "substantially purified" compound refers to a compound that is removed from its native environment and is at least about 60% free, preferably about 75% free, and most preferably about 90% free from other macromolecular components with which the compound is naturally associated. A polypeptide of the present invention may be substantially purified by preparative high performance liquid chromatography or other comparable techniques available in the art. See e.g., Creighton, T. (1983) Proteins, Structures and Molecular Principles, WH Freeman and Co., New York, which is herein incorporated by reference.

In other embodiments of the invention, polynucleotide sequences or fragments thereof which encode RBP1L1 polypeptides, or fusion proteins or functional equivalents thereof, may be used in recombinant DNA molecules to direct expression of the polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life that is longer than that of a transcript generated from the naturally occurring sequence.

Sequences encoding a desired polypeptide may be synthesized, in whole or in part, using conventional methods known in the art. See Caruthers, M. H., et al. (1980) Nucl. Acids Res. Symp. Ser. 215-223; Horn, T., et al. (1980) Nucl. Acids Res. Symp. Ser. 225-232; and Roberge, J. Y., et al. (1995) Science 269:202-204, which are herein incorporated by reference. Commercially available automated synthesizers, such as ABI 431A Peptide Synthesizer (Perkin Elmer), may be used. Moreover, the polynucleotide sequences of the present invention can be engineered using methods generally known in the art in order to alter polypeptide encoding sequences which modify the cloning, processing, or expression of the gene product, or a combination thereof. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, introduce mutations, and the like.

In some embodiments, the polypeptide may be a fusion protein that comprises multiple polypeptides as described herein, or that comprises at least one polypeptide as described herein and an unrelated sequence, such as a known tumor protein. Fusion proteins may generally be prepared using standard techniques, including recombinant techniques and chemical conjugation. A fusion protein may also be engineered to contain a cleavage site located between the polypeptide-encoding sequence and the heterologous protein sequence, so that the polypeptide may be cleaved and purified away from the heterologous moiety. A fusion partner may, for example, assist in providing T helper epitopes (an immunological fusion partner), preferably T helper epitopes recognized by humans, or may assist in expressing the polypeptide (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea, et al. (1985) Gene 40:39-46; Murphy, et al. (1986) PNAS USA 83:8258-8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

In order to express the polypeptides of the present invention, the nucleotide sequences encoding the polypeptide, or functional equivalents, may be inserted into appropriate expression vector or a cell, such as a breast cancer cell that naturally contains the RBP1L1 polynucleotide sequence, may be induced to express the polypeptide by methods known in the art.

A polynucleotide encoding a polypeptide of the present invention is then inserted in to a vector such as a cloning vector or an expression vector. An expression vector allows the polypeptide to be expressed when present in a host. Either the expression vector or the host may comprise the regulatory sequences necessary for expression of the polypeptide. Where the regulatory sequences are within the expression vector, the regulatory sequences are operatively linked to the sequence encoding the polypeptide. As used herein, "operably linked" means that the nucleotide sequence of interest is linked to at least one regulatory sequence in a manner that allows the polypeptide to be expressed in an in vitro transcription/translation system or in a host cell. Regulatory sequences include promoters, enhancers and other expression control elements (e.g., polyadenylation signals). See e.g., Goeddel (1990) GENE EXPRESSION TECHNOLOGY: METHODS IN ENZYMOLOGY, Academic Press, San Diego, Calif., which is herein incorporated by reference. It will be appreciated by those skilled in the art that the design of the expression vector can depend on such factors as the choice of the host cell to be transformed, the desired expression levels of the polypeptide, the compatibility of the host cell and the expressed polypeptide, and the like.

The vectors can be designed for expressing the polypeptides of the present invention in prokaryotic or eukaryotic host cells such as bacterial cells, insect cells, plant cells, yeast cells, or mammalian cells. In preferred embodiments, the host cells are bacterial cells. Suitable host cells are discussed further in Goeddel supra; Baldari, et al. (1987) EMBO J. 6:229-234; Kurjan and Herskowitz (1982) Cell 30:933-943; Schultz, et al. (1987) Gene 54:113-123; Smith, et al. (1983) Mol. Cell Biol. 3:2156-2165; Lucklow and Summers (1989) Virology 170:31-39; Seed (1987) Nature 329:840; Kaufman, et al. (1987) EMBO J. 6:187-6195; Sambrook, et al. (2000) MOLECULAR CLONING: A LABORATORY MANUAL. Cold Spring Harbor Laboratory, Cold Spring Harbor Laboratory Press, Cold Spring Harbor, N.Y., all of which are herein incorporated by reference.

Thus, the present invention also provides host cells comprising polynucleotides that encode the polypeptides of the present invention. Host cells include the progeny or potential progeny of the primary cell in which the polynucleotide was introduced. Because certain modifications may occur in succeeding generations due to either mutation or environmental influences, such progeny may not, in fact, be identical to the parent cell, but are still included within the scope and meaning of host cell.

The present invention also provides antibodies and fragments specific for the polypeptides, polynucleotides, and fragments thereof of the present invention and compositions comprising such. A polypeptide of the present invention may be used to prepare antibodies specific for cancerous cells and tumors by immunizing a suitable subject, e.g., rabbit, goat, mouse or other mammal with the polypeptide by conventional methods known in the art. Large quantities of neutralizing antibodies could be generated and then used in cancer immunotherapies by methods known in the art. The antibodies raised against the polypeptides of the present invention may be used to treat cancer by providing passive immunity or by creating immunotoxic compositions that are targeted to cancerous cells and tumors. Thus, the present invention provides antibodies that are raised against or derived from the polypeptides, polynucleotides, and fragments thereof of the present invention, and methods of using thereof.

Antibodies of the present invention may be produced by conventional methods known in the art. See e.g., Coligan (1991) CURRENT PROTOCOLS IN IMMUNOLOGY. Wiley/Greene, N.Y.; and Harlow and Lane (1989) ANTIBODIES: A LABORATORY MANUAL, Cold Spring Harbor Press, NY; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler and Milstein (1975) Nature 256:495-497, which are herein incorporated by reference. Therapeutic antibodies may be produced specifically for clinical use in humans by conventional methods known in the art. See Chadd, H. E. and S. M. Chamow (2001) Curr. Opin. Biotechnol. 12:188-194 and references therein, all of which are herein incorporated by reference.

As used herein, "antibody" refers to immunoglobulin molecules and immunologically active fragments that comprise an antigen binding site which specifically binds an antigen, such as the epitope of the present invention, IKPSLGSKK (SEQ ID NO:3). Examples of immunologically active fragments of immunoglobulin molecules include F(ab) and F(ab')$_2$ fragments which may be generated by treating the antibody with an enzyme such as pepsin. Polyclonal and monoclonal antibodies against the polypeptides of the present invention may be made by conventional methods known in the art.

The present invention also provides binding agents, which include antibodies and antigen-binding fragments thereof, that specifically bind to the polypeptide of the present invention. As used herein, an antibody, or antigen-binding fragment thereof "specifically binds" the polypeptides of the present invention if the reaction is detectable with convention assay methods known in the art and reactions, if any, with unrelated proteins under similar conditions are not detectable. As used herein, "binding" refers to a noncovalent association between two separate molecules such that a complex is formed. The ability to bind may be evaluated by, for example, determining a binding constant for the formation of the complex using methods known in the art.

Binding agents may be further capable of differentiating between individuals with and without a cancer, such as breast, lung, colon, pancreas, and ovarian cancer, using the assays provided herein and known in the art. Binding agents that indicate that an individual has cancer will bind to a target antigen to generate a signal that is greater than a signal, if any, of a control. To determine whether a binding agent satisfies this requirement, biological samples from patients with and without a cancer, as determined using standard clinical tests, may be assayed. Binding agents may be used alone or in combination to improve sensitivity or selectivity.

In preferred embodiments, the binding agent is an antibody or an antigen-binding fragment thereof that is specific for the RBP1L1 polypeptide of the present invention and fragments thereof. Antibodies and fragments thereof may be prepared by any of a variety of techniques known to those of ordinary skill in the art. See e.g., Harlow and Lane, Antibodies: A Laboratory Manual, Cold Spring Harbor Laboratory, 1988. Monoclonal antibodies specific for an antigenic polypeptide of interest may be prepared, for example, using the technique of Kohler and Milstein (1976) Eur. J. Immunol. 6:511-519, and improvements thereto, which are herein incorporated by reference.

Antibodies of the present invention may be coupled to one or more therapeutic agents, such as drugs, differentiation inducers, toxins, and the like. Suitable drugs include methotrexate, and pyrimidine and purine analogs. Suitable differentiation inducers include phorbol esters and butyric acid. Suitable toxins include ricin, abrin, diphtheria toxin, cholera toxin, gelonin, *Pseudomonas* exotoxin, *Shigella* toxin, and pokeweed antiviral protein. The therapeutic agent may be coupled (e.g., covalently bonded) to the antibody either directly or indirectly. In some embodiments multiple molecules of a therapeutic agent are coupled to one antibody molecule. In some embodiments, more than one type of agent may be coupled to one antibody.

A linker group may be used to couple the therapeutic agent and the antibody. A linker group can function as a spacer to distance an antibody from an agent in order to avoid interference with binding capabilities. A linker group can also serve to increase the chemical reactivity of a substituent on an agent or an antibody, and thus increase the coupling efficiency. A variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues using conventional methods known in the art. Where a therapeutic agent is more potent when free from the antibody portion of the immunoconjugates of the present invention, it may be desirable to use a linker group that is cleavable during or upon internalization into a cell. A number of different cleavable linker groups are known in the art. Carriers may be used to couple the binding agent to the therapeutic agent or encapsulate the agents together. Suitable carriers include proteins such as albumins, peptides and polysaccharides such as aminodextran, and the like.

The compositions of the present invention also include T-cells specific for the RPB1L1 polypeptide of the present invention. The T-cells may be prepared by conventional methods known in the art. The T-cells may be stimulated with the RBP1L1 polypeptide, RBP1L1 polynucleotide, an antigen presenting cell (APC) that expresses the RBP1L1 polypeptide, or a combination hereof. APCs may be transfected ex vivo or in vivo with a polynucleotide of the present invention such that the polypeptide, or an immunogenic portion thereof, is expressed on the cell surface by conventional methods known in the art. See e.g. WO 97/24447; and Mahvi, et al. (1997) Immunol. Cell Biol. 75:456-460, which is herein incorporated by reference. Stimulation is performed under conditions and for a time sufficient to permit the generation of T-cells that are specific for the RBP1L1 polypeptide. T cells are considered to be specific for the polypeptides of the present invention if the T cells specifically proliferate, secrete cytokines or kill target cells coated with the polypeptide or expressing a gene encoding the polypeptide. T cell specificity may be evaluated using any of a variety of conventional techniques.

The polypeptides, polynucleotides, antibodies, or fragments thereof of the present invention may be used as an active agent in pharmaceutical compositions used to treat, prevent, inhibit, or modulate cancer. Preferred pharmaceutical compositions are those comprising at least one polypeptide, polynucleotide, antibody, or fragment thereof of the present invention in a therapeutically effective amount, and a pharmaceutically acceptable vehicle. Supplementary active agents can also be incorporated into the compositions. Suitable supplementary active agents include pacitaxel, coumarin compounds, other tumor antigens such as HOM-MEL-40, NY-ESO-1, MAGE-1, GAGE, BAGE, antibodies against other tumor antigens, and the like. The pharmaceutical compositions of the present invention may also include an adjuvant. As used herein, an "adjuvant" refers to any substance which, when administered with or before the polypeptide, polynucleotide, or antibody of the present invention, aids the polypeptide, polynucleotide, or antibody in its mechanism of action.

As used herein, "vehicle" and "carrier" are used interchangeably to indicate any and all solvents, dispersion media, vehicles, coatings, diluents, antibacterial and antifungal agents, isotonic and absorption delaying agents, buffers, carrier solutions, suspensions, colloids, and the like. As used herein, "pharmaceutically acceptable" vehicle or carrier is intended to include any and all solvents, dispersion media, coatings, antibacterial and antifungal agents, isotonic and absorption delaying agents, and the like, compatible with pharmaceutical administration. The use of such media and agents for pharmaceutical active substances is well known in the art. See e.g. REMINGTON: THE SCIENCE AND PRACTICE OF PHARMACY. $20^{th}$ ed. (2000) Lippincott Williams & Wilkins. Baltimore, Md., which is herein incorporated by reference. Except insofar as any conventional media or agent is incompatible with the active ingredient, its use in the therapeutic compositions is contemplated. Pharmaceutical carriers are preferably biocompatible, and may also be biodegradable.

The compositions described herein may be administered as part of a sustained release formulation that provides a slow release of the active agent following administration. Time-delay or time-release material is known in the art and includes glyceryl monostearate or glyceryl distearate alone or with a wax, ethylcellulose, hydroxypropylmethylcellulose, methylmethacrylate, and the like. The use of such media and agents for pharmaceutically active substances is well known in the art. Likewise, the sustained release formulations may be prepared by conventional methods in the art. See e.g. Coombes et al. (1996) Vaccine 14:1429-1438, which is herein incorporated by reference. The sustained-release formulations may contain a polypeptide, polynucleotide or antibody dispersed in a carrier matrix, contained within a reservoir surrounded by a rate controlling membrane, or a combination thereof. Other delayed-release vehicles include supramolecular biovectors, which comprise a non-liquid hydrophilic core and, optionally, an external layer comprising an amphiphilic compound, such as a phospholipid. The amount of active agent contained within a sustained release formulation depends upon the site of implantation, the rate and expected duration of release and the nature of the condition to be treated or prevented.

The pharmaceutical compositions of the present invention may include pharmaceutically acceptable salts, multimeric forms, prodrugs, active metabolites, precursors and salts of such metabolites of the polypeptides, polynucleotides, antibodies, or fragments thereof described herein.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids and bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acids glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See e.g., Lee et al., (1984) Biochem. 23:4255, which is herein incorporated by reference. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism of a specified compound or salt thereof in the body. Prodrugs and active metabolites of a compound may be identified using routine techniques known in the art. See e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res. 13:224-331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991), which are herein incorporated by reference.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Suitable pharmaceutical formulations for particular routes of administration are well known in the art. See e.g. REMINGTON: THE SCIENCE AND PRACTICE OF PHARMACY. $20^{th}$ ed. (2000) Lippincott Williams & Wilkins. Baltimore, Md., which is herein incorporated by reference.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active agents.

The pharmaceutical compositions of the present invention may be provided in dosage unit forms in unit-dose or multi-dose containers, such as sealed ampoules or vials. Such containers are preferably hermetically sealed to preserve sterility of the formulation until use. In general, the compositions of the present invention may be stored as suspensions, solutions or emulsions in oily or aqueous vehicles. Alternatively, the compositions may be stored in a freeze-dried condition requiring only the addition of a sterile liquid carrier prior to use. As used herein, "dosage unit form" refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

It will be appreciated that the actual dosages of the polynucleotides, polypeptides, antibodies, and fragments thereof used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of experimental data. Administration of prodrugs may be dosed at weight levels that are chemically equivalent to the weight levels of the fully active forms.

The biological activity of the polynucleotides, polypeptides, antibodies, fragments thereof, and compositions of the present invention may be measured by any of the methods available to those skilled in the art, including in vitro and in vivo assays and those provided herein. Other pharmacological methods may also be used to determine the efficacy of the polynucleotides, polypeptides, antibodies, fragments thereof, and compositions of the present invention as antineoplastic agents and cancer immunotherapeutics.

Toxicity and therapeutic efficacy of such compounds can be determined by standard pharmaceutical procedures in cell cultures or experimental animals. For example, the $LD_{50}$ (the dose lethal to 50% of the population), and the $ED_{50}$ (the dose therapeutically effective in 50% of the population) may be determined by conventional methods in the art. The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to normal, non-cancerous, or benign cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions of the present invention include immunogenic compositions. The immunogenic compositions include an active immunizing agent, such as a polypeptide of the present invention, or a passive immunizing agent, such as an antibody raised against or specifically binds the polypeptide of the present invention. The immunogenic composition may elicit an immune response that need not be protective or the immunogenic composition may provide passive immunity. A vaccine elicits a local or systemic immune response that is protective against subsequent challenge by the immunizing agent such as the polypeptides of the present invention, or an immunologically cross-reactive agent. Accordingly, as used herein, an "immunogenic composition" can refer to vaccines as well as antibodies. A protective immune response may be complete or partial, i.e. a reduction in symptoms as compared with an unvaccinated mammal. Conventional methods in the art may be used to determine the feasibility of using the polypeptides of the present invention as a cancer or tumor vaccine.

Thus, the present invention provides immunogenic compositions comprising the polypeptides, polynucleotides, antibodies, or fragments thereof of the present invention that may be used to treat, prevent, inhibit, or modulate cancer. As used herein, an "immunogenic amount" is an amount that is sufficient to elicit an immune response in a subject and depends on a variety of factors such as the immunogenicity of the polypeptide, the manner of administration, the general state of health of the subject, and the like. The typical immunogenic amounts for initial and boosting immunization for therapeutic or prophylactic administration ranges from about 0.01 mg to about 0.1 mg per about 65-70 kg body weight of a subject. Examples of suitable immunization protocols include initial immunization injections at time 0 and 4 or initial immunization injections at 0, 4, and 8 weeks, which initial immunization injections may be followed by further booster injections at 1 or 2 years.

A variety of immunostimulants may be employed in the immunogenic compositions of the present invention. For example, an immunostimulant may be included. An "immunostimulant" is any substance that enhances or potentiates an immune response (antibody and/or cell-mediated) to an exogenous antigen. Examples of immunostimulants include adjuvants, biodegradable microspheres (e.g., polylactic galactide), liposomes, cytokines, interleukins, and chemokines. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKlineGlaxo); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; and cytokines, such as GM-CSF or interleukin-2, -7, or -12, may be used as adjuvants. Other suitable adjuvants include Montanide ISA 720 (Seppic, France), SAF (Chiron, Emeryville, Calif.), ISCOMS (CSL), MF-59 (Chiron), the SBAS series of adjuvants, such as SBAS-2 or SBAS-4 (SmithKlineGlaxo), Detox, RC-529, other aminoalkyl glucosaminide 4-phosphates (AGPs); incomplete N-acetyl-muramyl-L-threonyl-D-isoglutamine (thr-MDP); N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE); and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by conventional methods in the art.

The vaccines of the present invention may be prepared by conventional methods known in the art. See e.g. M. F. Powell and M. J. Newman, eds. VACCINE DESIGN Plenum Press (NY, 1995), which is herein incorporated by reference. The immunogenic compositions of the present invention may further comprise other agents, which may be biologically active or inactive. For example, one or more immunogenic portions of other tumor antigens, either incorporated into a fusion polypeptide or as a separate compound, may be included in the compositions.

A variety of delivery vehicles may be employed within pharmaceutical compositions and vaccines to facilitate production of an antigen-specific immune response that targets tumor cells. Suitable delivery vehicles include antigen presenting cells (APCs), such as dendritic cells, macrophages, B cells, monocytes and other cells that may be engineered to be efficient APCs. Such cells may be genetically modified to increase the capacity for presenting the antigen, to improve activation of the T cell response, maintenance of the T cell response, to have anti-tumor effects per se, to be immunologically compatible with the receiver, or a combination thereof. APCs may generally be isolated from any of a variety of biological fluids and organs, including tumor and peritumoral tissues, and may be autologous, allogeneic, syngeneic, or xenogeneic cells by methods known in the art.

The present invention also provides polypeptides, polynucleotides, antibodies, or compositions of the present invention that may be provided in kits along with instructions for use. A kit comprising a pharmaceutical composition may include the pharmaceutical composition as a single dose or multiple doses. The kit may include a device for delivering the pharmaceutical composition. The device may be a multi-chambered syringe for intramuscular delivery, a microneedle or set of microneedle arrays for transdermal delivery, a small balloon for intranasal delivery, or a small aerosol generating device for delivery by inhalation.

The polynucleotides, polypeptides, antibodies, and compositions of the present invention may be used as active agents in therapeutic methods to treat cancer in a subject. Generally, these therapeutic methods comprise administering to the subject a therapeutically effective amount of at least one active agent.

As used herein, a "therapeutically effective amount" refers to an amount of an active agent that may be used to treat cancer in a subject as compared to a control. As used herein, "treating cancer" includes inhibiting, preventing, modulating, or reducing the growth or spread of cancer as well as reducing or maintaining the amount of cancerous cells in a subject or biological sample as compared to a control. Again, the skilled artisan will appreciate that certain factors may influence the dosage required to effectively treat a subject, including the severity and stage of the cancer, previous treatments, the general health and age of the subject, and the like. A therapeutically effective amount may be readily determined by conventional methods known in the art. It should be noted that treatment of a subject with a therapeutically effective amount of a polypeptide, a polynucleotide, or an antibody of the present invention can include a single treatment or, preferably, can include a series of treatments.

The polynucleotides, polypeptides, antibodies, and compositions of the present invention may be used in cancer immunotherapies. In preferred embodiments, the cancer is breast, lung, colon, pancreas, or ovarian cancer. In particular, the polynucleotides, polypeptides, antibodies, and compositions of the present invention may be administered to a subject, preferably human. The subject may or may not be afflicted with cancer. Accordingly, the polynucleotides, polypeptides, antibodies, and compositions of the present invention may be used to prevent the development of a cancer in a subject or to treat a subject afflicted with a cancer. A cancer may be diagnosed using criteria generally accepted in the art, including the presence of a malignant tumor, or the methods described herein. The polynucleotides, polypeptides, antibodies, and compositions of the present invention may be administered prior to, during, or after surgical removal of primary tumors or treatment such as administration of radiotherapy or conventional chemotherapeutic drugs, or a combination thereof. Administration may be by any suitable method, including administration by intravenous, intraperitoneal, intramuscular, subcutaneous, intranasal, intradermal, anal, vaginal, topical and oral routes.

The polynucleotides, polypeptides, antibodies, and compositions of the present invention may be used in combination with or as a substitution for conventional cancer therapies. For example, the polynucleotides, polypeptides, antibodies, and compositions of the present invention may also be used alone or in combination with a supplementary active compound such as methotrexate, taxol, and the like, to treat breast, lung, colon, pancreas, or ovarian cancer in a subject. Likewise, the polynucleotides, polypeptides, antibodies, and compositions of the present invention may be used in combination with or in place of surgical procedures.

Cancer immunotherapies of the present invention may be broadly classified as adoptive, passive, and active. The therapeutic methods of the present invention may be active immunotherapy, in which treatment relies on the in vivo stimulation of the endogenous host immune system to react against tumors with the administration of immune response-modifying agents, such as the polypeptides and polynucleotides of the present invention. Active immunotherapies of the present invention include administering the antigenic epitope of the present invention, a polynucleotide encoding the antigenic epitope, adjuvants, immunostimulants, and the like. In some embodiments, other tumor associated antigens, such as HOM-MEL-40, NY-ESO-1, MAGE-1, GAGE, BAGE, KASIFLK (SEQ ID NO:5), GLQKASIFLK (SEQ ID NO:6), KASIFLKTRV (SEQ ID NO:7), and the like, may be administered along with the IKPSLGSKK (SEQ ID NO:3) or variants thereof. In some preferred embodiments, the IgM antibody response in the subject being treated is activated or enhanced.

Alternatively, the therapeutic methods of the present invention may be passive immunotherapy, in which treatment involves the delivery of agents with established tumor-immune reactivity (such as effector cells or antibodies) that can directly or indirectly mediate antitumor effects and does not necessarily depend on an intact host immune system. The T cell receptors and antibody receptors specific for the polypeptides of the present invention may be cloned, expressed, and transferred into other vectors or effector cells for adoptive immunotherapy. The polypeptides provided herein may also be used to generate antibodies or anti-idiotypic antibodies for passive immunotherapy by methods known in the art. Passive immunotherapies of the present invention include administering antibodies against IKPSLGSKK (SEQ ID NO:3) or a variant thereof alone or coupled to toxins, chemotherapeutic agents, radioactive isotopes, and the like. In some embodiments, antibodies against other tumor associated antigens, such as HOM-MEL-40, NY-ESO-1, MAGE-1, GAGE, BAGE, KASIFLK (SEQ ID NO:5), GLQKASIFLK (SEQ ID NO:6), KASIFLKTRV (SEQ ID NO:7), and the like, may be administered along with the antibodies against IKPSLGSKK (SEQ ID NO:3) or variants thereof. In some embodiments, lymphokines and other types of immunostimulants may be administered. See e.g., Bajorin et al. (1988) Proc. Annu. Meet. Am. Soc. Clin. Oncol. 7:A967.

Adoptive immunotherapies of the present invention include isolating a subject's circulating lymphocytes or tumor infiltrated lymphocytes and activating the lymphocytes by conventional methods known in the art and then administering the activated lymphocytes to a subject to be treated.

In some embodiments, the present invention provides methods of enhancing the immune response in a subject comprising the steps of contacting at least one lymphocyte with a polypeptide comprising IKPSLGSKK (SEQ ID NO:3) or a variant thereof. In some embodiments, other antigenic polypeptides, such as HOM-MEL-40, NY-ESO-1, MAGE-1, GAGE, BAGE, KASIFLK (SEQ ID NO:5), GLQKASIFLK (SEQ ID NO:6), KASIFLKTRV (SEQ ID NO:7), and the like, may be contacted with the lymphocyte along with the a polypeptide comprising IKPSLGSKK (SEQ ID NO:3) or a variant thereof. Additional compounds, such as immunostimulants may be administered to the subject.

Routes and frequency of administration of the therapeutic compositions described herein, as well as dosage, will vary from individual to individual, and may be readily established using standard techniques. In general, the pharmaceutical compositions and vaccines may be administered by injection, intranasally, or orally. Preferably, between 1 and 10 doses may be administered over a 52-week period. Preferably, 6 doses are administered, at intervals of 1 month, and booster vaccinations may be given periodically thereafter. Alternate protocols may be appropriate for individual patients.

A suitable dose is an amount of a polynucleotide, polypeptide, antibody, or composition of the present invention that, when administered as described above, is capable of promoting an anti-tumor immune response, and is at least about 10% or more above the basal level. In general, for pharmaceutical compositions and vaccines comprising one or more polypeptides, the amount of each polypeptide present in a dose ranges from about 25 µg to about 5 mg per kg of the subject. Suitable dose sizes will vary with the size of the subject, but will typically range from about 0.1 ml to about 5 ml. Methods of using the vaccines of the present invention are also contemplated. Suitable vaccines are capable of causing an immune response that leads to an improved clinical outcome, such as more frequent remissions, complete or partial or longer disease-free survival, in vaccinated patients as compared to non-vaccinated patients.

Responses to the therapeutic methods of the present invention can be monitored by measuring the anti-tumor antibodies in a patient or by vaccine-dependent generation of cytolytic effector cells capable of killing the patient's tumor cells in vitro. Immune responses may generally be evaluated using standard proliferation, cytotoxicity or cytokine assays, which may be performed using samples obtained from a subject before and after treatment. Other methods known in the art for monitoring the effect of a given therapeutic method are also contemplated.

As used herein, a "therapeutically effective amount" of a polynucleotide, polypeptide, antibody, or composition of the present invention is an amount which treats cancer in a subject as compared to a control. As defined herein, a therapeutically effective amount of a compound of the present invention may be readily determined by one of ordinary skill by routine methods known in the art. For example, a therapeutically effective amount of a compound of the invention ranges from about 0.1 to about 1000 mg/kg body weight, such as, about 1 to about 750 mg/kg body weight, about 1 to about 500 mg/kg body weight, about 1 to about 350 mg/kg body weight, about 1 to about 200 mg/kg body weight, about 1 to about 100 mg/kg body weight, about 1 to about 50 mg/kg body weight, about 1 to about 10 mg/kg body weight, about 1 to about 5 mg/kg body weight, and the like. The skilled artisan will appreciate that certain factors may influence the dosage required to effectively treat a subject, including but not limited to the severity of the disease or disorder, previous treatments, the general health and/or age of the subject, and other diseases present.

Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present.

The therapeutic methods of the present invention may include a single treatment or a series of treatments. For example, a subject may be treated with an immunogenic composition of the invention at least once. However, the subject may be treated with the immunogenic composition from about one time per week to about once daily for a given treatment period. The length of the treatment period will depend on a variety of factors such as the stage and aggressiveness of the cancer. It will also be appreciated that the effective dosage of the compound used for treatment may increase or decrease over the course of a particular treatment. Changes in dosage may result and become apparent by standard diagnostic assays known in the art. In some instances chronic administration may be required.

The polynucleotides, polypeptides, antibodies, and fragments thereof of the present invention may be used to detect, diagnose, or monitor cancer in a subject. Specifically, a cancer may be detected or monitored in a subject based on the presence or amount of one or more polynucleotides, polypeptides, or fragments thereof of the present invention in a biological sample obtained from the patient. Thus, the polynucleotides, polypeptides, antibodies, and fragments thereof of the present invention may be used as markers to indicate the presence or absence of a cancer, such as breast, lung, colon, pancreas, and ovarian cancer, as well as other cancers. The binding agents provided herein generally permit detection of the level of antigen that binds to the agent in the biological sample. Polynucleotide primers and probes may be used to detect the differential expression of mRNA encoding a tumor protein using assays known in the art, The differential expression of the epitope of the present invention is indicative of the presence or absence of a cancer. Generally, the presence or absence of a cancer in a subject may be determined by contacting a biological sample obtained from a subject with a binding agent and determining whether the antigenic epitope of the present invention is differentially expressed in the biological sample as compared to a control. As sample wherein the antigenic epitope is differentially expressed is indicative of cancer.

In some embodiments, the binding agent used in the assays of the present invention is immobilized on a solid support to bind to and remove the polypeptide from the remainder of a sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A, or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use in assays include full-length RBP1L1 polypeptide and fragments thereof to which the binding agent binds.

The solid support may be any material known to those of ordinary skill in the art to which a polypeptide may be attached. For example, the solid support may be a test well in a microtiter plate or a nitrocellulose or other suitable membrane. Alternatively, the support may be a bead, fiber, or disc, such as glass, fiberglass, latex, or plastic such as polystyrene or polyvinylchloride. The support may also be a magnetic particle or a fiber optic sensor. The binding agent may be immobilized on the solid support by conventional methods known in the art. As used herein, "immobilization" refers to both noncovalent association, such as adsorption, and covalent attachment (which may be a direct linkage between the agent and functional groups on the support or may be a linkage by way of a cross-linking agent). Adsorption may be achieved by contacting the binding agent, in a suitable buffer, with the solid support for a suitable amount of time sufficient to immobilize an adequate amount of binding agent. Covalent attachment of binding agent to a solid support may be achieved by first reacting the support with a bifunctional reagent that will react with both the support and a functional group, such as a hydroxyl or amino group, on the binding agent. See e.g. PIERCE IMMUNOTECHNOLOGY CATALOG AND HANDBOOK (1991) at A12-A13, which is herein incorporated by reference.

The presence of T cells that specifically react with RBP1L1 polypeptides in a biological sample may indicate a cancer in a subject. A cancer may also be detected based on the level of mRNA encoding RBP1L1 in a biological sample. Techniques for both PCR based assays and hybridization assays are well known in the art. See e.g. Mullis et al. (1987) Cold Spring Harbor Symp. Quant. Biol., 51:263; and Erlich ed., PCR TECHNOLOGY, Stockton Press, NY, 1989, which are herein incorporated by reference.

The compositions of the present invention may be used as markers for the progression of cancer. In this embodiment, the assays as described above for the diagnosis of a cancer may be performed over time, and the change in the level of at least one reactive polypeptide or polynucleotide is evaluated. For example, the assays may be performed every 24 to 72 hours for a period of 6 months to 1 year, and thereafter performed as needed. In general, a cancer is progressing in those subjects in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding RBP1L1 in a biological sample. Such kits generally comprise at least one oligonucleotide probe or primer that hybridizes to a polynucleotide encoding RBP1L1. Such an oligonucleotide may be used, for example, within a PCR or hybridization assay. Additional components that may be present within such kits include a second oligonucleotide and/or a diagnostic reagent or container to facilitate the detection of a polynucleotide encoding RBP1L1.

In some embodiments, antibodies that specifically bind RBP1L1 may be used for the diagnosis of cancer, or in assays to monitor patients being treated with RBP1L1, agonists, antagonists or inhibitors. The antibodies useful for diagnostic purposes may be prepared in the same manner as those described above for therapeutics. Diagnostic assays for RBP1L1 include methods that utilize the antibody and a label to detect RBP1L1 in human body fluids or extracts of cells or tissues. The antibodies may be used with or without modification, and may be labeled by joining them, either covalently or non-covalently, with a reporter molecule. A wide variety of reporter molecules that are known in the art may be used.

A variety of protocols including ELISA, RIA, and FACS for measuring RBP1L1 are known in the art and provide a basis for diagnosing altered or abnormal levels of RBP1L1 expression. Normal or standard values for RBP1L1 expression are established by combining body fluids or cell extracts taken from normal mammalian subjects, preferably human, with antibody to RBP1L1 under conditions suitable for complex formation. The amount of standard complex formation may be quantified by various methods known in the art, but preferably by photometric methods. Quantities of RBP1L1 expressed in subject, control and disease samples from biopsied tissues are compared with the standard values. Deviation between standard and subject values establishes the parameters for diagnosing disease.

In another embodiment of the invention, the polynucleotides encoding RBP1L1 may be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of RBP1L1 may be correlated with disease. The diagnostic assay may be used to distinguish between absence, presence, and excess expression of RBP1L1, and to monitor regulation of RBP1L1 levels during therapeutic intervention.

In one aspect, hybridization with PCR probes which are capable of detecting polynucleotide sequences, including genomic sequences, encoding RBP1L1 or closely related molecules, may be used to identify nucleic acid sequences that encode RBP1L1. The specificity of the probe will determine whether the probe identifies only naturally occurring sequences encoding RBP1L1, alleles, or related sequences.

Probes may also be used for the detection of related sequences, and should preferably contain at least 50% of the nucleotides from any of the RBP1L1 encoding sequences. The hybridization probes of the subject invention may be DNA or RNA and derived from the polynucleotide sequence of SEQ ID NO:1 or from genomic sequence including promoter, enhancer elements, and introns of the naturally occurring RBP1L1.

Means for producing specific hybridization probes for DNAs encoding RBP1L1 include the cloning of nucleic acid sequences encoding RBP1L1 or RBP1L1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radiolabels such as $^{32}P$ or $^{35}S$, or enzymatic labels, such as alkaline phosphatase coupled to the probe via avidin/biotin coupling systems, and the like.

Polynucleotide sequences encoding RBP1L1 may be used for the diagnosis of cancer, such as breast, lung, colon, pancreas, and ovarian cancer. The polynucleotide sequences encoding RBP1L1 may be used in Southern or Northern analysis, dot blot, or other membrane-based technologies; in PCR technologies; or in dip stick, pin, ELISA or chip assays utilizing fluids or tissues from patient biopsies to detect altered RBP1L1 expression. Such qualitative or quantitative methods are well known in the art.

In order to provide a basis for the diagnosis of cancer associated with expression of RBP1L1, a normal or standard profile for expression is established. This may be accomplished by combining body fluids or cell extracts taken from normal subjects, either animal or human, with a sequence, or a fragment thereof, which encodes RBP1L1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once cancer is diagnosed and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual to clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding RBP1L1 may involve the use of PCR. Such oligomers may be chemically synthesized, generated enzymatically, or produced from a recombinant source. Oligomers will preferably consist of two nucleotide sequences, one with sense orientation (5' 3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods that may also be used to quantitate the expression of RBP1L1 include radiolabeling or biotinylating nucleotides, coamplification of a control nucleic acid, and standard curves onto which the experimental results are interpolated. See Melby, P. C., et al. (1993) J. Immunol. Methods 159:235-244; and Duplaa, C., et al. (1993) Anal. Biochem. 229-236, which are herein incorporated by reference. The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences that encode RBP1L1 may also be used to generate hybridization probes that are useful for mapping the naturally occurring genomic sequence. The sequences may be mapped to a particular chromosome or to a specific region of the chromosome using well known techniques including FISH, FACS, or artificial chromosome constructions, such as yeast artificial chromosomes, bacterial artificial chromosomes, bacterial P1 constructions or single chromosome cDNA libraries. See Price, C. M., (1993) Blood Rev. 7:127-134; and Trask, B. J., (1991) Trends Genet. 7:149-154; Verma, et al. (1988) HUMAN CHROMOSOMES: A MANUAL OF BASIC TECHNIQUES, Pergamon Press, New York, which are herein incorporated by reference. Correlation between the location of the gene encoding RBP1L1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, RBP1L1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between RBP1L1 and the agent being tested, may be measured.

Another technique for drug screening that may be used provides for high throughput screening of compounds having suitable binding affinity to the protein of interest as described in published PCT application WO84/03564 and by using cells described in WO 99/15650. In another embodiment, one may use competitive drug screening assays in which neutralizing antibodies capable of binding RBP1L1 specifically compete with a test compound for binding RBP1L1.

A variety of protocols for detecting and measuring the expression of polynucleotide-encoded products, using either polyclonal or monoclonal antibodies specific for the product are known in the art. See Hampton, R., et al. (1990) SEROLOGICAL METHODS, A LABORATORY MANUAL, APS Press, St Paul, Minn.; and Maddox, D. E., et al. (1983) J. Exp. Med. 158:1211-1216, which are herein incorporated by reference.

A wide variety of labels and conjugation techniques are known by those skilled in the art and may be used in various nucleic acid and amino acid assays. Methods for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits such as those available from Amersham Pharmacia Biotech, Promega and US Biochemical Corp. Suitable reporter molecules or labels, which may be used, include radionuclides, enzymes, fluorescent, chemiluminescent, or chromogenic agents as well as substrates, cofactors, inhibitors, magnetic particles, and the like.

The following examples are intended to illustrate but not to limit the invention.

EXAMPLE 1

Human IgG Purification and MCF-7 cDNA Library Immunoscreening

An IgG antibody fraction was prepared from serum of a patient with breast cancer. See Cao, J., et al. (1999) Breast Cancer Res. Treat. 53:279-290, which is herein incorporated by reference. Antibodies against *Escherichia coli* proteins and the heptapeptide KASIFLK (SEQ ID NO:5) in the IgG fraction were, respectively, removed first with an affinity column containing an immobilized bacterial lysate from *E. coli* Y1090 and then with a KASIFLK peptide affinity column. A λgt11 cDNA expression library from MCF-7 cells was screened with the resulting purified IgG (at 20 μg/ml, about a 1:400 dilution of the original serum) by the method of Young and Davis. See Young and Davis (1983) PNAS USA 80:1194-1198, which is herein incorporated by reference.

$4 \times 10^6$ plaques of the λgt11 MCF-7 cDNA expression library were screened with human IgG purified from the serum of a patient with breast cancer and two immunopositive clones, 131 and 151, were detected. PCR analysis of both clones using λgt11 forward and reverse primers revealed a 4.0-kilobase (kb) insert. DNA from clones 131 and 151 was transfected into lysogenic *E. coli* Y1089 and expression of the β-galactosidase fusion protein induced with IPTG.

Western blot analysis of the whole cell lysates with the purified IgG detected a fusion protein of about 128 kDa for each clone. Given that β-galactosidase is 116 kDa, the size of the open reading frame of each clone would be about 12 kDa. Therefore, only a small portion of the insert of about 4.0-kb appeared to encode the protein detected by the purified IgG.

EXAMPLE 2

Expression and Analysis of Fusion Proteins

*E. coli* Y1090 and Y1089 were used for screening and protein expression of λgt11 recombinants, respectively. After immunopositive recombinants clones 131 and 151 were detected and plaques purified, the λgt11 recombinants were infected in lysogenic bacterial strain Y 1089 that enhances the frequency of phage lysogeny. Fusion proteins were expressed in *E. coli* Y1089 as described by Oka, T., et al. (1994) Cancer Res. 54:3511-3515, which is herein incorporated by reference. Protein samples were separated by sodium dodecyl sulfate-polyacrylamide gel electrophoresis (SDS-PAGE) on 4%-20% gradient gels, and proteins were stained with Coomassie blue R-250 or electrotransferred to nitrocellulose membranes for Western blot analysis. The Western blot method of assessing IgG antibody reactivity against the β-galactosidase fusion-protein antigens has been described by Kikumoto, Y., et al. (1995) Hybridoma 14:45-50, which is herein incorporated by reference. Peroxidase-conjugated rabbit anti-human IgG (Pierce, Rockford, Ill.) was used as the secondary antibody.

FIG. 1 provides the results of expression of immunopositive fusion proteins in *E. coli*. The lanes designated as "A" in FIG. 1 provide the sodium dodecyl sulfate-polyacrylamide gel electrophoresis (SDS-PAGE) followed by Coomasie brilliant blue staining. The lanes designated as "B" in FIG. 1 provide the Western blot analysis with the purified human IgG. The lanes designated "a" are the lysate of isopropyl β-D-thiogalactopyranoside (IPTG)-induced lysogen from clone 131. The lanes designated "b" are the lysate of IPTG-induced lysogen from clone 151. The band at 128 kDa represents the fusion protein containing a 107 amino acid insert. Molecular mass markers (in kDa) are indicated in the left lane.

EXAMPLE 3

Sequence Analysis of Immunoreactive Clones

DNA inserts from immunoreactive λgt11 clones 131 and 151 were amplified by polymerase chain reaction (PCR) with λgt11 forward and reverse primers and cloned into the PCRII plasmid using the TA cloning strategy (Invitrogen Corp., Carlsbad, Calif.). Total RNA from MCF-7 and peripheral blood mononuclear cells (PBMCs) were amplified by reverse transcription RT-PCR, and cDNA from human ovarian cells (Marathon-Ready™ kit, Clontech, Palo Alto, Calif.) was amplified by PCR. Products from all reactions were cloned into the PCRII plasmid and sequenced completely. DNA and amino acid sequences were compared with sequences in GenBank using the BLAST tool at National Center for Biotechnology Information (NCBI). Publication output for RBP1 and RBP1L1 protein sequences alignment was generated with the Baylor College of Medicine search launcher BOXSHADE program.

Northern blot analysis was performed on human multiple tissue northern (MTN II) and human endocrine system MTN blots (Clontech). On these blots, each lane contained about 2 μg of poly(A)+ RNA from human spleen, thymus, prostate, testis, ovary, small intestine, colon, peripheral blood leukocyte, pancreas, adrenal medulla, thyroid, adrenal cortex, or stomach. Membranes were hybridized with a $^{32}$P-labeled 441-base-pair (bp) fragment of RBP1L1 cDNA that was amplified by PCR from the immunopositive clone 151. Blots were washed twice in 0.1% standard saline citrate (SSC) and 0.1% SDS for 20 minutes and then exposed to Kodak BIOMAX film at –80° C. with an intensifying screen for 36 hours. As a loading control, blots were stripped and reprobed with the control glyceraldehyde 3-phosphoate dehydrogenase (G3PDH) gene to prove RNA integrity.

A stop codon at nucleotide 322 in clone 151 was investigated to determine whether it was due to a somatic mutation in the gene or caused by mispairing during cDNA synthesis by sequencing RT-PCR products amplified from MCF-7 and PBMC RNA. Total RNA (1 μg) from MCF-7 cells and PBMCs was primed with (dT) 12-18 and reverse transcribed with SuperScript RT (Gibco, Rockville, Md.). A 470-bp segment of RBP1L1, spanning the region, which contained the stop codon in clone 151, was amplified by PCR with the following sequence-specific primers:

sense=5'-ATGGAGGAGGAGAGGAATATAATAC-CAAG-3' (SEQ ID NO: 8)

antisense=5'-CTGAAATGGTGGTTTGGACAAGCGC-CGA-3' (SEQ ID NO:9) (Operon Technologies, Alameda, Calif.).

PCR was performed to denature it at 94° C., 2 minutes; followed by 35 amplification cycles of the denatured product at 94° C., 30 seconds; annealing temperature at 68° C. for 30 seconds and extension at 72° C., 1 minutes with a final extension at 72° C., 5 minutes in a Perkin-Elmer thermal cycler. Several RT-PCR products were sequenced to determine whether they also encoded a stop codon at the same position. In order to identify the remaining 5' coding sequence of RBP1L1 and the 5'-untranslated region (UTR), rapid amplification of 5' cDNA ends (5' RACE) was performed on cDNA from human ovarian cells (Marathon-Ready™, Clontech) using a 5' primer that had been designed based on the sequence of the rat retinablastoma binding protein-1-related gene (rRBP1-R), which shares 84% sequence identity with the partial RBP1L1 sequence.

PCR was performed to denature it at 94° C., 2 minutes; followed by 35 amplification cycles of the denatured product at 94° C., 30 seconds; annealing temperature at 68° C. for 30 seconds and extension at 72° C., 1 minutes with a final extension at 72° C., 5 minutes in a Perkin-Elmer thermal cycler. Several RT-PCR products were sequenced to determine whether they also encoded a stop codon at the same position. In order to identify the remaining 5' coding sequence of RBP1L1 and the 5'-untranslated region (UTR), rapid amplification of 5' cDNA ends (5' RACE) was performed on cDNA from human ovarian cells (Marathon-Ready™, Clontech) using a 5' primer that had been designed based on the sequence of the rat retinablastoma binding protein-1-related gene (rRBP1-R), which shares 84% sequence identity with the partial RBP1L1 sequence.

A sense primer:

5'-AGAGTCACCATGAAGGCCCTTGATGATGAGC-3' (SEQ ID NO:10)

corresponding to the 5' end of rRBP1-R (nucleotides 30-57) and an antisense primer:

5'-TGGGATTATATTCCTCTCCTCCTCCATC-3' (SEQ ID NO:11)

corresponding to the 5' end of the incomplete human RBP1L1 sequence (nucleotides 12-39 of clone 151) were used. Sequencing of the resulting reaction product identified the remaining 5' cDNA sequence of human RBP1L1.

To obtain the 5' UTR sequence, the region was amplified by using an adaptor primer 1 (AP1, Clontech) and an antisense primer:

5'-ATACGGCATCAGGCTTTGGTGCAGTGTCAC-3' (SEQ ID NO:12)

corresponding to the 5' sequence of rRBP1-R (nucleotides 741-771). PCR denature was performed at 94° C., 2 minutes; followed by 35 amplification cycles of denature at 94° C., 30 seconds; annealing at a temperature of 68° C., 30 seconds and extension at 72° C., 3 minutes with a final extension 72° C., 7 minutes in a thermal cycler (Perkin-Elmer).

To examine the expression level of RBP1L1 mRNA, quantitative PCR was performed on cDNA panels from human normal and cancer tissues (MTC II and Tumor MTC respectively, Clontech). These panels contain first-strand cDNA from human cancers of the breast, lung, colon, lung, prostate, colon, ovary, and pancreas and from normal human thymus, prostate, testis, ovary, small intestine, colon, and peripheral blood leukocytes. A set of RBP1L1-specific oligonucleotides:

sense=5'-AGGGAATAGCTCGCCAGCAG-GTTTTGATG-3' (SEQ ID NO:13)

antisense=5'-TCGGCACTTGTCATATTTTCCAGGTC-CGAC-3' (SEQ ID NO:14);

spanning a 441-bp cDNA segment was used for PCR with 1 ng of cDNA from each tissue. PCR was performed denature at 94° C., 2 minutes; followed by 35 amplification cycles of denature at 94° C., 30 seconds; annealing at temperature of 68° C., 30 seconds and extension at 72° C., 1 minute with a final extension 72° C., 7 minutes. Reaction products (6 µl) were evaluated by gel electrophoresis and bands were visualized with ethidium bromide. As a loading control, amplified product from a set of G3PDH control PCR primers (Clontech) was included to assure integrity of cDNA samples of each tissue.

After amplifying the cDNA inserts of the immunopositive clones 131 and 151 and cloning into a PCRII vector, the inserts were sequenced. The 4032-bp sequence of the two clones was identical. Beyond the β-galactosidase sequence, each clone contained an open reading frame of 107 amino acids ending at a stop codon (TAA) at nucleotides 322-324. Investigation of the premature stop codon by sequencing RT-PCR products amplified from total RNA from MCF-7 cells and PBMCs, around nucleotide 322, showed that none of the 10 cDNA clones examined had a TAA stop codon at nucleotides 322-324 and that all had the sequence AAA. Consequently, the stop codon likely resulted from a mutation that was introduced during the synthesis of MCF-7 cDNA. Correction of this mutation extended the open reading frame an additional 683 nucleotides and predicted that the full-length protein was 790 amino acids long, consistent with the length of other RB binding proteins.

Figure 2:
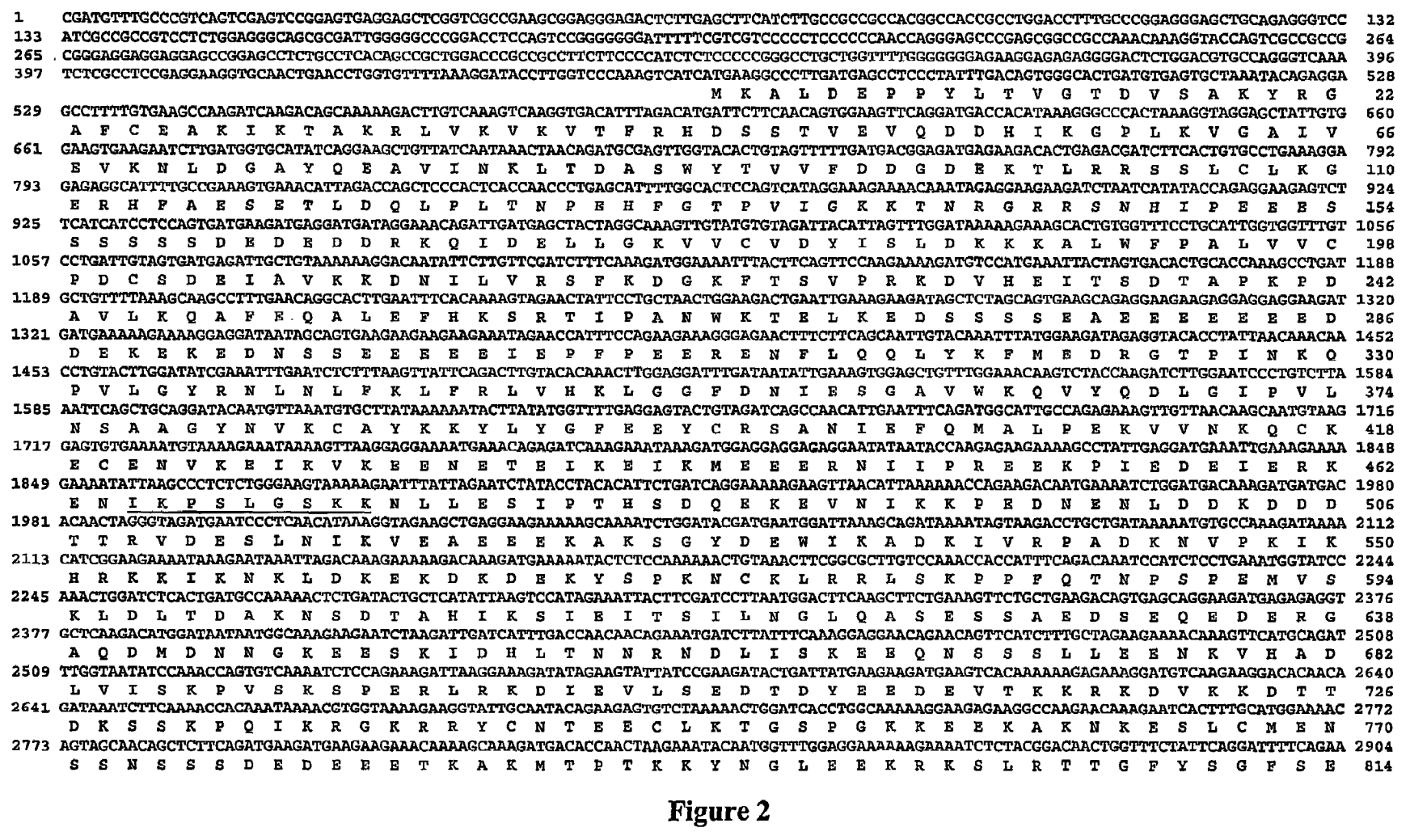
Figure 2:
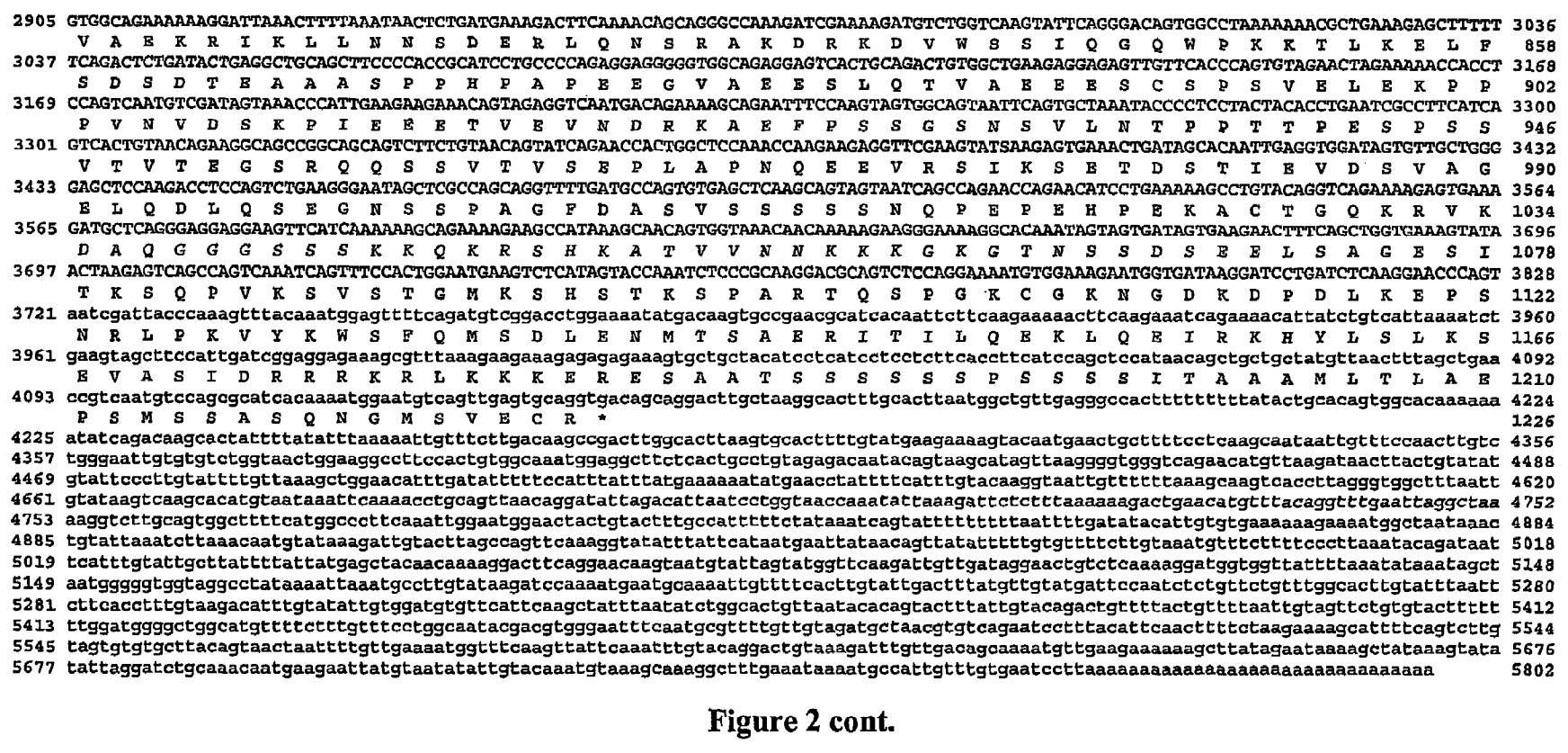

5' RACE identified additional 1770 nucleotides at the 5' end of clone 151 that contained the 5' UTR and the rest of the 5' cDNA sequence of RBP1L1. The complete cDNA sequence (5802 bp) (SEQ ID NO:1) and the predicted amino acid sequence (1226 amino acids) (SEQ ID NO:2) are shown in FIG. 2. The GenBank accession number of the partial (BCAA) and complete RBP1L1 cDNA sequence is AF214114 (SEQ ID NO:15) which encodes the polypeptide sequence set forth in SEQ ID NO:16.

NCBI BLAST search results revealed that the following four protein sequences are similar to RBP1L1: (1) human RB binding protein (hRBP; accession number AF083249); (2) human RBP1-like protein (hRBP1-L; accession number NP057485); (3) rat RBP1-related protein (rRBP1-R; accession number AF245512); and (4) human RBP1 (hRBP1; accession number NM002892). Only partial sequences of the RB binding protein and RBP1-like protein gene were available. The derived amino acid sequence alignment of RBP1L1 and hRBP1 is shown in FIG. 3. RBP1L1 shares 74%, 72%, 86%, and 37% amino acid sequence identity with hRBP, hRBP1-L, rRBP1-R, and hRBP1, respectively.

EXAMPLE 3

Fusion Protein and Antibody Purification

GST-RBP1L1 fusion protein (1.5 mg) was purified with the glutathione-argarose beads (Pharmacia Biotech, Alameda, Calif.) from 50 mg of total protein extracted from *E. coli* bacterial lysate. The purified fusion protein (2 mg/ml) was coupled to CNBr-activated Sepharose 4B as per the manufacturer's instructions (Pharmacia Biotech). Three milliliters of purified IgG (1.5 mg/ml) was passed over the fusion-protein affinity column, and the column was washed extensively with phosphate-buffered saline (PBS) to remove nonspecifically adsorbed proteins. Specifically, bound IgG was eluted with 0.1 M acid glycine at pH 3.0, and the pH was adjusted immediately with 1.0 M Tris buffer (pH 9.0).

Human IgG, isolated from a human hybridoma cell line that was not immunoreactive to MCF-7 cells was used as a negative control antibody. Control human IgG was prepared by growing human hybridoma cells in RPMI medium 1640 (Life Technologies, Inc., Rockville, Md.) comprising 10% fetal bovine serum until senescence. Conditioned culture medium was removed from the cultures, and debris was removed by centrifugation at 1,000×g for 10 minutes. IgG was purified with a protein A-Sepharose 4B Fast Flow column (Pharmacia Biotech) and eluted with 0.1 M acid glycine at pH 3.0, and the pH was adjusted immediately with 1 M Tris buffer a, pH 9.0. The purified IgG was dialyzed against PBS.

EXAMPLE 4

Carboxyl-Terminal Truncation of Glutathione S-Transferase (GST)-RBP1L1 and Expression of GST Fusion Proteins To identify the site of the immunogenic epitope within the first 107 residues of clone 151, a series of carboxyl-terminal deletion constructs were generated by amplifying and cloning overlapping 5' DNA fragments of clone 151 (construct 1:1-105, 2:1-114, 3: 1-142, 4: 1-154, 5: 1-208, 6: 1-235, and 7: 1-279) into the GST expression vector, pGEX2. The sense 5' PCR primer contained a BamHI and all antisense primers contained an EcoRI site (indicated in bold in the primer sequences shown below), allowing amplified products to be cloned into the respective sites of pGEX-2T. Primers for each of the constructs were as follows:

1: sense=5'-TGACGGATCCTGCGGCCGCAAAG-3' (SEQ ID NO:17);
antisense=5'-TCTGGAATTCCTTCCCA-GAGAGAGGGC-3' (SEQ ID NO:18);
2: antisense=5'-TCTGGAATTCATTCTTTTTACTTCC-3' (SEQ ID NO:19);
3: antisense=5'-TCTGGAATTCCCTGATCAGAATGT-GTAGG-3' (SEQ ID NO:20);
4: antisense=5'-TCTGGAATTCCCCAGATTTTCAT-TGTCTTC-3' (SEQ ID NO:21);
5: antisense=5'-TCTGGAATTCCCTACCCTAGTTGT-GTC-3' (SEQ ID NO:22);
6: antisense=5'-TCTGGAATTCGCTTTAATCCAT-TCATC-3' (SEQ ID NO:23); and
7: antisense=5'-TCTGGAATTCGCTTTTTCTTCCT-CAGC-3' (SEQ ID NO:24);

Expression of GST-RBP1L1 fusion proteins was induced with 0.1 mM isopropyl β-D-thiogalactopyranoside (IPTG). Bacterial lysates were subjected to SDS-PAGE and subsequently transferred to nitrocellulose membranes for Western blot analysis with the purified specific IgG antibody. See Kikumoto, Y., et al. (1995) Hybridoma 14:45-50, which is herein incorporated by reference.

EXAMPLE 5

Synthetic Peptides

Peptides were synthesized based on the deduced amino acid sequence of the immunoreactive clone and enriched by HPLC to greater than 80% purity. (Research Genetics, Inc., Huntsville, Ala.).

For clone 151, the following eight peptide residues were derived and synthesized:
1. Residues 29-37 (464-473 of RBP1L1): IKPSLGSKK (SEQ ID NO:3)
2. Residues 29-38 (464-474 of RBP1L1): IKPSLGSKKN (SEQ ID NO:25)
3. Residues 30-38 (465-474 of RBP1L1): KPSLGSKKN (SEQ ID NO:26)
4. Residues 29-36 (464-472 of RBP1L1): IKPSLGSK (SEQ ID NO:27)
5. Residues 30-36 (465-472 of RBP1L1): KPSLGSK (SEQ ID NO:28)
6. Residues 31-37 (466-473 of RBP1L1): PSLGSKK SEQ ID NO:29)
7. Residues 29-35 (464-471 of RBP1L1): IKPSLGS (SEQ ID NO:30)
8. Residues 32-38 (467-474 of RBP1L1): SLGSKKN (SEQ ID NO:31)

The C-terminal end of the synthetic peptides contained a carboxyl group and the N-terminal end contained a free amino group. High pressure liquid chromatography (HPLC) was used to purify these peptides (greater than about 80% purity).

EXAMPLE 6

Inhibition of Antibody Activity by Synthetic Peptides

To determine the minimal number of amino acids necessary for antibody binding, synthetic peptides of various lengths were tested for their ability to inhibit the binding of purified specific IgG to GST-RBP1L1 fusion protein by Western blot analysis. The synthetic peptides tested were:
IKPSLGSKK (SEQ ID NO:3);
IKPSLGSKKN (SEQ ID NO:25);
KPSLGSKKN (SEQ ID NO:26);
IKPSLGSK (SEQ ID NO:27);
KPSLGSK (SEQ ID NO:28);
PSLGSKK (SEQ ID NO:29);
IKPSLGS (SEQ ID NO:30);
SLGSKKN (SEQ ID NO:31); and
KPSLGSKK (SEQ ID NO:32).

The final concentration of each peptide was 100 μg/ml, and the concentration of purified IgG was 1.5 μg/ml. The antigen and purified IgG mixture was agitated at 4° C. overnight, and the inhibition of antibody binding was assessed by Western blotting using GST-RBP1L1 fusion protein as the target antigen.

EXAMPLE 7

Enzyme-Linked Immunosorbent Assay (ELISA) with Synthetic Peptide Antigens

The binding of purified specific IgG to synthetic peptides was assessed by ELISA. 96-well polystyrene plates (Reacti-Bind maleic anhydride-activated plates, Pierce) coated with each of the peptides (100 μl of 5 μg/ml) in PBS, incubated overnight at 4° C., and then blocked with 1% bovine serum albumin. Purified specific IgG (200 μg/ml) was serially diluted 1:250, 1:500, 1:1000, 1:2000, and 1:4000, then added in triplicate to peptide-coated wells (500 ng per well), and incubated for 3 hours at room temperature. Peroxidase-conjugated goat anti-human IgG (Pierce) was added at room temperature for 1 hour, followed by the addition of 400 μg/ml of o-phenylenediamine dihydrochloride in peroxide substrate solution. Reactivity was measured at 490 nm. Background absorbance without the primary antibody was subtracted from each sample's absorbance.

EXAMPLE 8

Immunoperoxidase Staining of MCF-7 Cells and PBMCs

PBMCs were centrifuged onto glass slides using a cytocentrifuge, and MCF-7 cells were plated on slide chambers and incubated in $CO_2$ incubator for 2 days. Cells were fixed in 2% paraformaldehyde. Slides were dipped in PBS for 5 minutes and then treated sequentially with 0.1% Triton X-100 for 10 minutes to make cell membranes permeable and 3% hydrogen peroxide for 10 minutes to quench endogenous peroxidase activity. Next, the slides were washed in running water for 5 minutes, and cells were immunocytochemically stained with VECTASTAIN ABC (Vector laboratories, Inc. Burlingame, Calif.). Slides that had been blocked with goat serum were incubated overnight with either the purified RBP1L1-specific IgG (10 μg/ml), a human monoclonal IgG (10 μg/ml) as a MCF-7 negative control, or PBS as a PBMC negative control. After washing with PBS, the slides were incubated with biotin-labeled goat anti-human IgG at room temperature for 1 hour. After washing, slides were incubated with ABC reagent for 30 minutes, and then added with horseradish peroxidase substrate for color development. The slides were counterstained with hematoxylin-eosin.

EXAMPLE 9

Expression of RBP1L1 in Human Normal Testis and Cancer Tissues

Figure 4A:
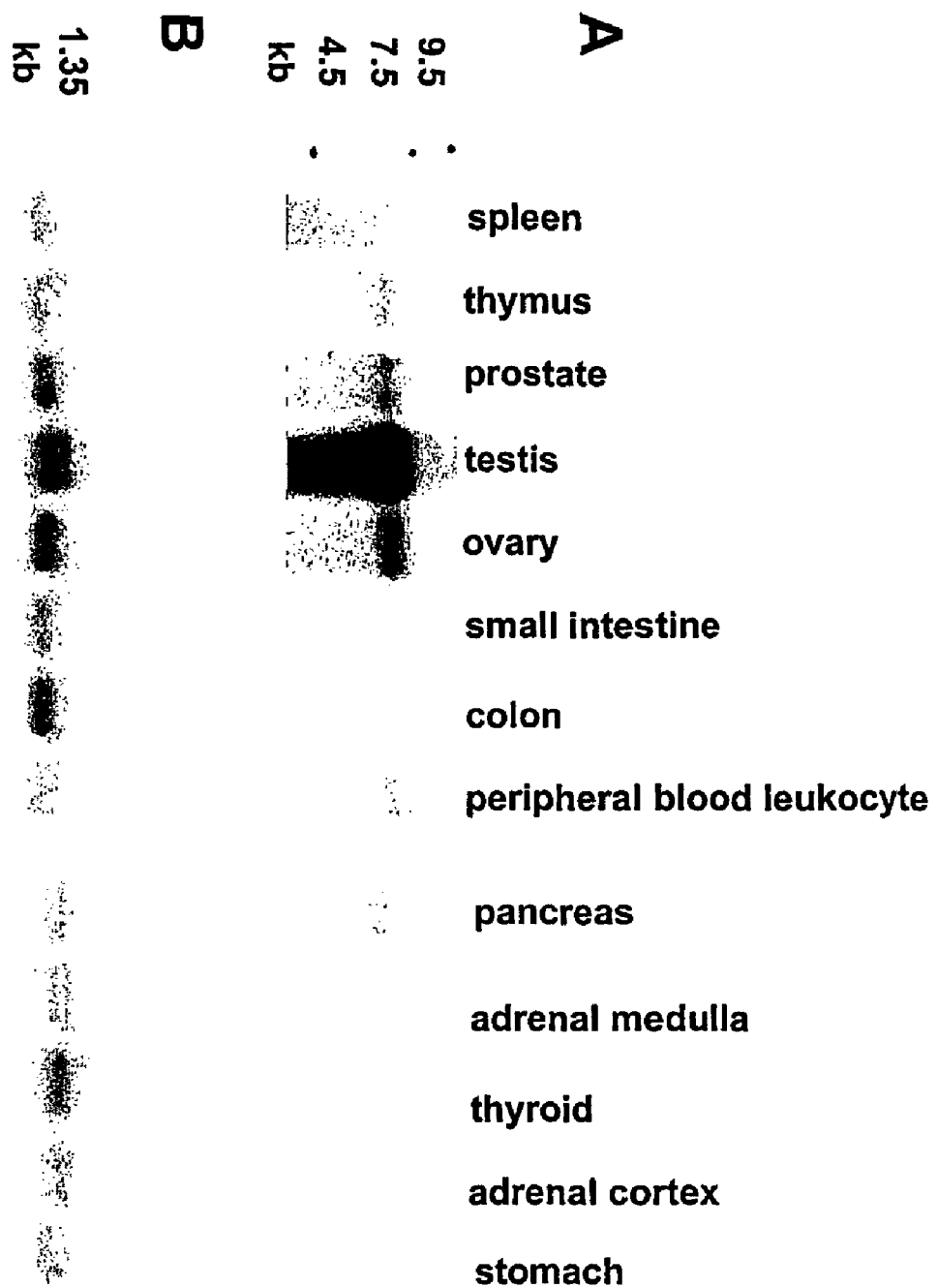
FIG. 4A provides the Northern blot analysis of RBP1L1 mRNA expression in 13 normal human tissues.

Expression of RBP1L1 mRNA in normal human tissues was analyzed by Northern blotting with RBP1L1-specific probes. Abundant expression of a 7.5-kb transcript was detected in the testis, with reduced levels in the thymus, prostate, and ovary. FIG. 4A shows the Northern blot analysis of RBP1L1 mRNA expression in 13 normal human tissues. Poly(A)+ RNAs (2 µg per lane) were transferred to a nylon membrane and hybridized with $^{32}$P-labeled RBP1L1 cDNA probes. Blots were stripped and reprobed with a 1.35-kb radiolabeled G3PDH cDNA as a loading control to evaluate the integrity of RNA. Expression was absent or very low in nine other adult tissues examined. The 1.35-kb G3PDH band was used as a loading control.

Figure 4B:
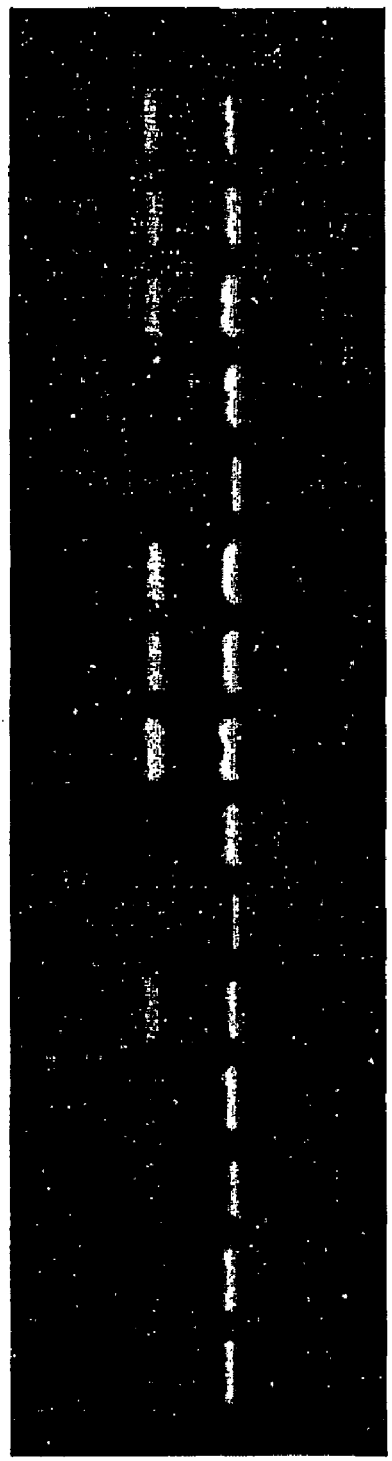
FIG. 4B shows the differential expression of the RBP1L1 gene. The 983-bp band is the G3PDH PCR product. The 441-bp band is the RBP1L1 PCR product.

To determine the level of RBP1L1 mRNA expression in a variety of cancers, a quantitative RT-PCR was performed with a set of RBP1L1-specific primers. Of the six histologic types of cancers examined, five (breast, ovary, lung, colon, and pancreas) expressed substantially higher levels of RBP1L1 mRNA as compared to the six normal tissues. FIG. 4B provides the results of the quantitative reverse transcriptase-polymerase chain reaction (PCR) assay that shows differential expression of RBP1L1 gene. RBP1L1 expression is restricted to testis as shown by PCR products after 28 PCR cycles (6 µl of product per lane). In contrast, RBP1L1 transcripts are detected in many cancers. G3PDH PCR primers were used as a positive loading control to confirm the integrity of cDNA. The 983-bp band is the G3PDH PCR product. The 441-bp band is the RBP1L1 PCR product.

Thus, expression of RBP1L1 in the testis and cancer cells was comparable. Essentially no expression was detected in prostate cancer cells. Therefore, RBP1L1 has a very restricted tissue distribution, being expressed predominately in cancer tissues where it may contribute to the pathophysiology.

EXAMPLE 10

Antigen Epitope Mapping in Recombinant Protein from Clone 151

Peptide sequences that contain the antigenic epitope were identified by testing the GST-RBP1L1 fusion constructs of Example 4. Western blot analysis revealed that the purified IgG recognized GST-RBP1L1 fusion-constructs 2-7 but not GST-RBP1L1 fusion-construct 1, suggesting that constructs 2-7 contained the antigen epitope. Because constructs 1 and 2 differed by only three residues at the carboxyl-terminal end, the epitope was expected to be located between nucleotides 84 and 114 in clone 151 within a 10-amino acid stretch.

The minimum number of amino acids required for the antibody binding was determined by testing various truncated synthetic peptides in ELISAs and on Western blots. The following set of peptides was generated by sequentially reducing the 10-amino acid peptide by one amino acid from either the amino terminus or the carboxyl terminus:

IKPSLGSKK (SEQ ID NO:3);
IKPSLGSKKN (SEQ ID NO:25);
KPSLGSKKN (SEQ ID NO:26);
IKPSLGSK (SEQ ID NO:27);
KPSLGSK (SEQ ID NO:28);
IKPSLGS (SEQ ID NO:30);
KPSLGSKK (SEQ ID NO:32); and
PSLGSKKN (SEQ ID NO:33).

Figure 5:
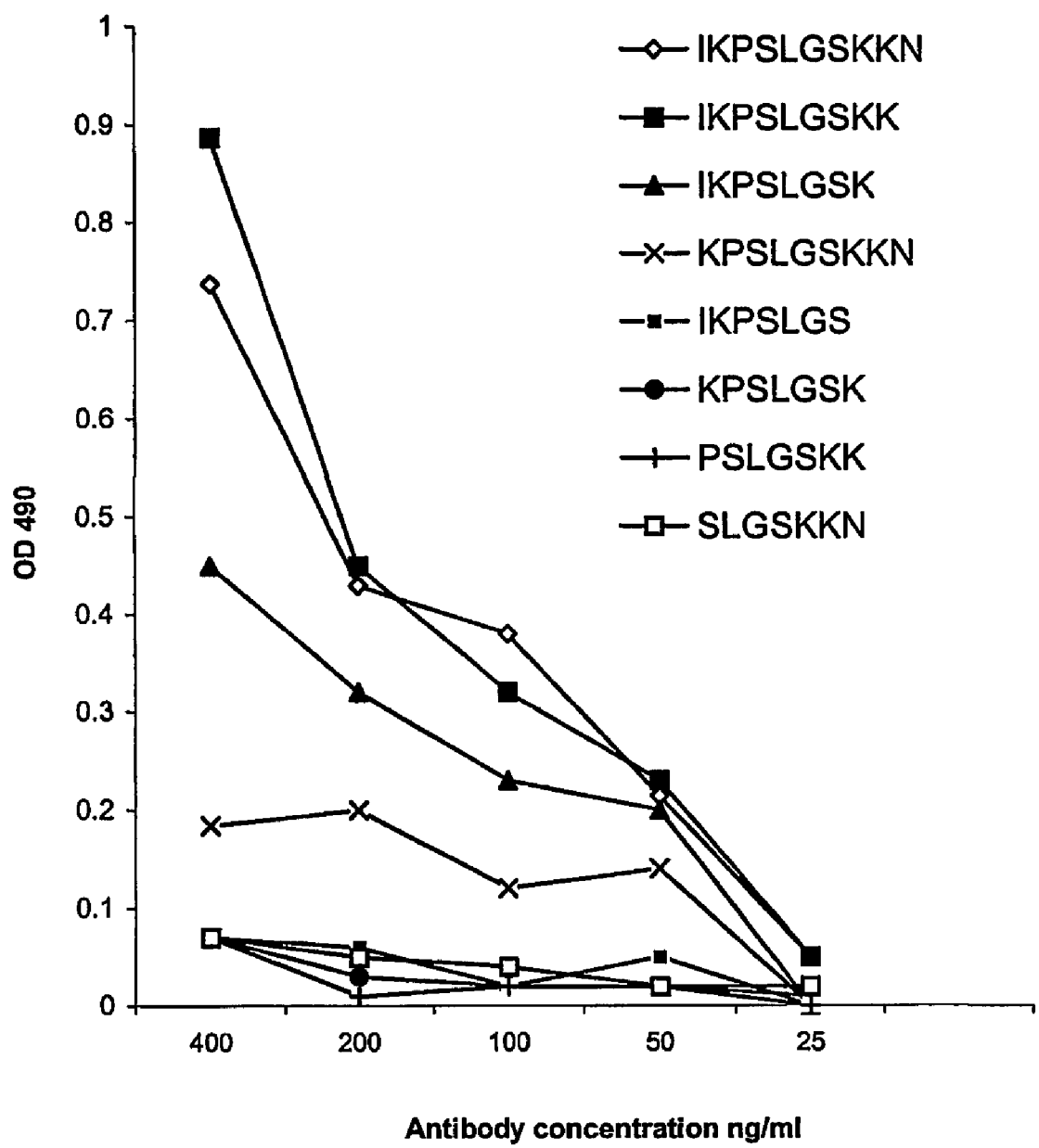
FIG. 5 shows the concentration of specific IgG purified from the serum of a patient with breast cancer that binds to various synthetic peptides in an enzyme-linked immunosorbent assay (ELISA). The sequence identifiers from top to bottom are SEQ ID NO:25, SEQ ID NO:3, SEQ ID NO:27, SEQ ID NO:26, SEQ ID NO:30, SEQ ID NO:28, SEQ ID NO:29, and SEQ ID NO:31

The antigenic activity of each peptide (5 µg/ml) was tested for its ability to competitively inhibit the binding of purified specific IgG (0.5 µg/ml) to the GST-RBP1L1 fusion protein on Western blots. The peptides IKPSLGSKKN (SEQ ID NO:25) and IKPSLGSKK (SEQ ID NO:3) completely inhibited the purified specific IgG from binding to the GST-RBP1L1 fusion protein from clone 151, indicating that the C-terminal asparagine (N) is not essential for the antibody binding. However, deletion of the C-terminal lysine (K) from IKPSLGSKK (SEQ ID NO:3) substantially reduced the inhibition, and deletion of N-terminal isoleucine (I) from IKPSLGSKK (SEQ ID NO:3) eliminated the inhibition. This result was verified with an ELISA. FIG. 5 shows that RBP1L1 specific IgG purified from the serum of a subject with breast cancer binds to various synthetic peptides in an ELISA. The wells of a 96-well ELISA plate were coated with 100 µl of a peptide (5 µg/ml). The specific human IgG (200 µg/ml) was serially diluted from 1:250 to 1:4,000. Thus, IKPSLGSKK (SEQ ID NO:3), residues 465-473 of the full-length RBP1L1 protein sequence, represent the minimal epitope recognized by the purified specific human IgG.

EXAMPLE 11

Cytological and Immunocytochemical Analysis of Antigen

Figure 6:
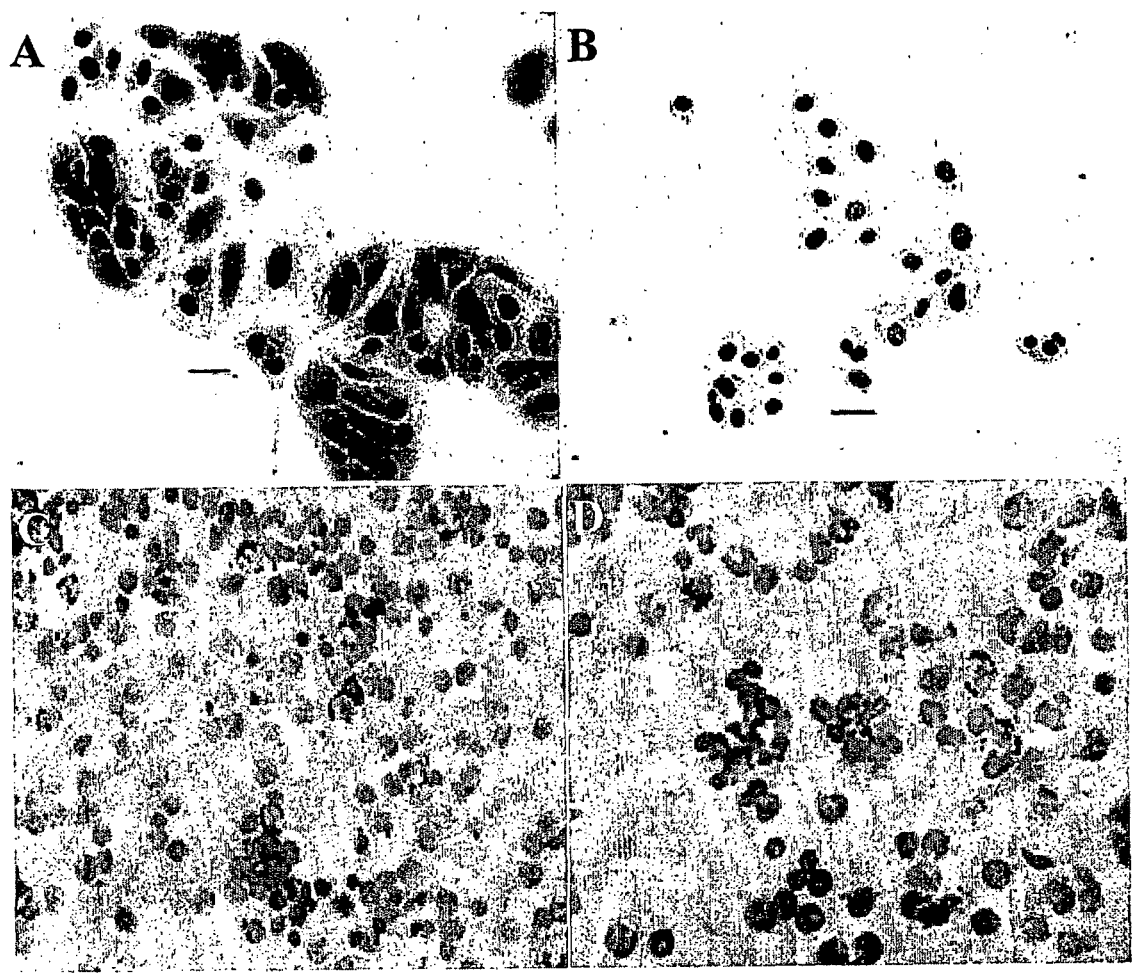
FIG. 6A shows the immunoperoxidase staining of MCF-7 breast cancer cells in the cytoplasm.
FIG. 6B shows no staining of MCF-7 cells with irrelevant human IgG monoclonal antibody alone.
FIG. 6C shows only membrane staining in human PBMCs with the purified RBP1L1 specific IgG.
FIG. 6D shows membrane staining of PBMCs with only the second antibody. Scale bars=100 μm.

Purified specific IgG that had been affinity purified on the GST-RBP1L1 fusion-protein affinity column was used to determine the cellular location of the IKPSLGSKK antigen (SEQ ID NO:3) in MCF-7 cells and in PBMCs. Immunocytochemical staining with the purified specific IgG was strong in the cytoplasm, with little or no staining of other cellular components. See FIG. 6. FIG. 6A shows staining of the cytoplasm of MCF-7 cells, FIG. 6B shows that no staining of MCF-7 cells was observed with the irrelevant human IgG monoclonal antibody alone, FIG. 6C shows only membrane staining of human PBMCs with the purified IgG, and FIG. 6D shows membrane staining of PBMCs only with the second antibody, thereby suggesting that membrane staining is due to non-specific binding of the second antibody. Thus, antigen-specific staining was not observed in PBMCs from healthy donors. See FIGS. 6C and D.

EXAMPLE 12 mRNA Microarray

Figure 7A:
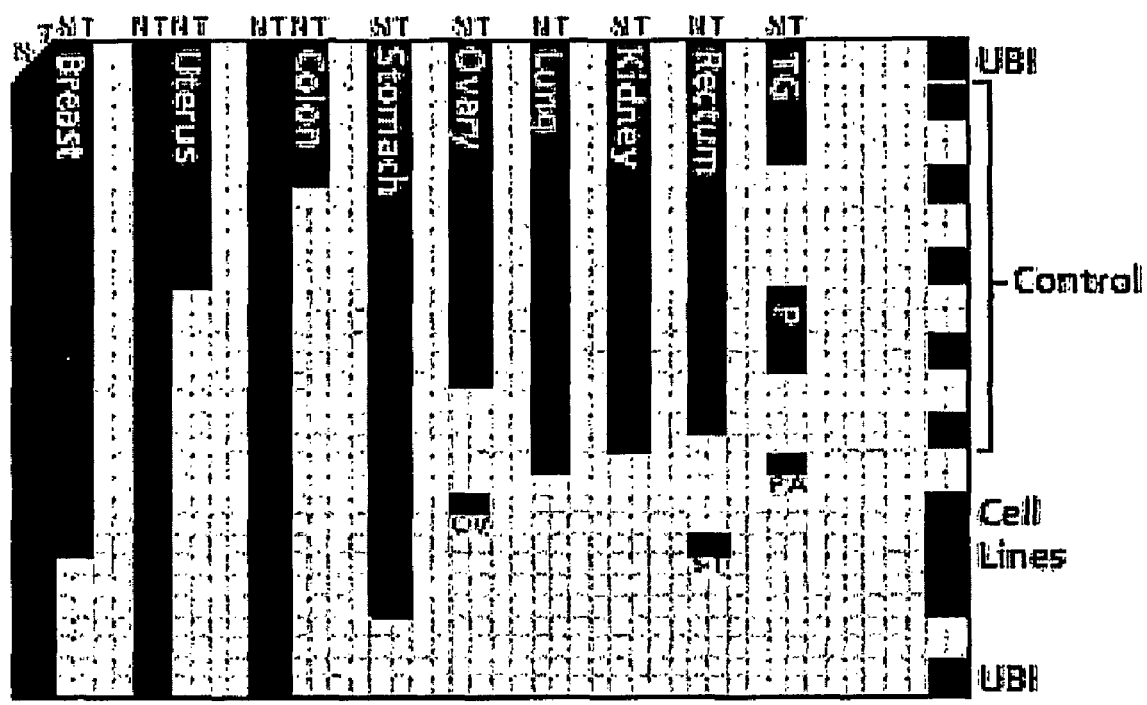
FIG. 7 shows a mRNA microarray that shows that RBP1L1 is differentially expressed in cancer cells as compared to normal cells.

Analysis of gene expression across multiple tumor samples and of expression from tumor and normal tissue of the same subject was performed on Cancer Profiling Expression Array on nylon membrane that together contain more than 241 cDNA pairs, each pair representing tumor and normal tissue from a single subject. These arrays provide a high-throughput format for analyzing differential gene expression (Clontech). The microarray contains cDNA from normal and carcinoma of breast, uterus, colon, stomach, ovary, lung, kidney, rectum, thyroid gland, cervix, small intestine, pancreas, and prostate. The legend to the microarray is shown in FIG. 7A.

Figure 7B:
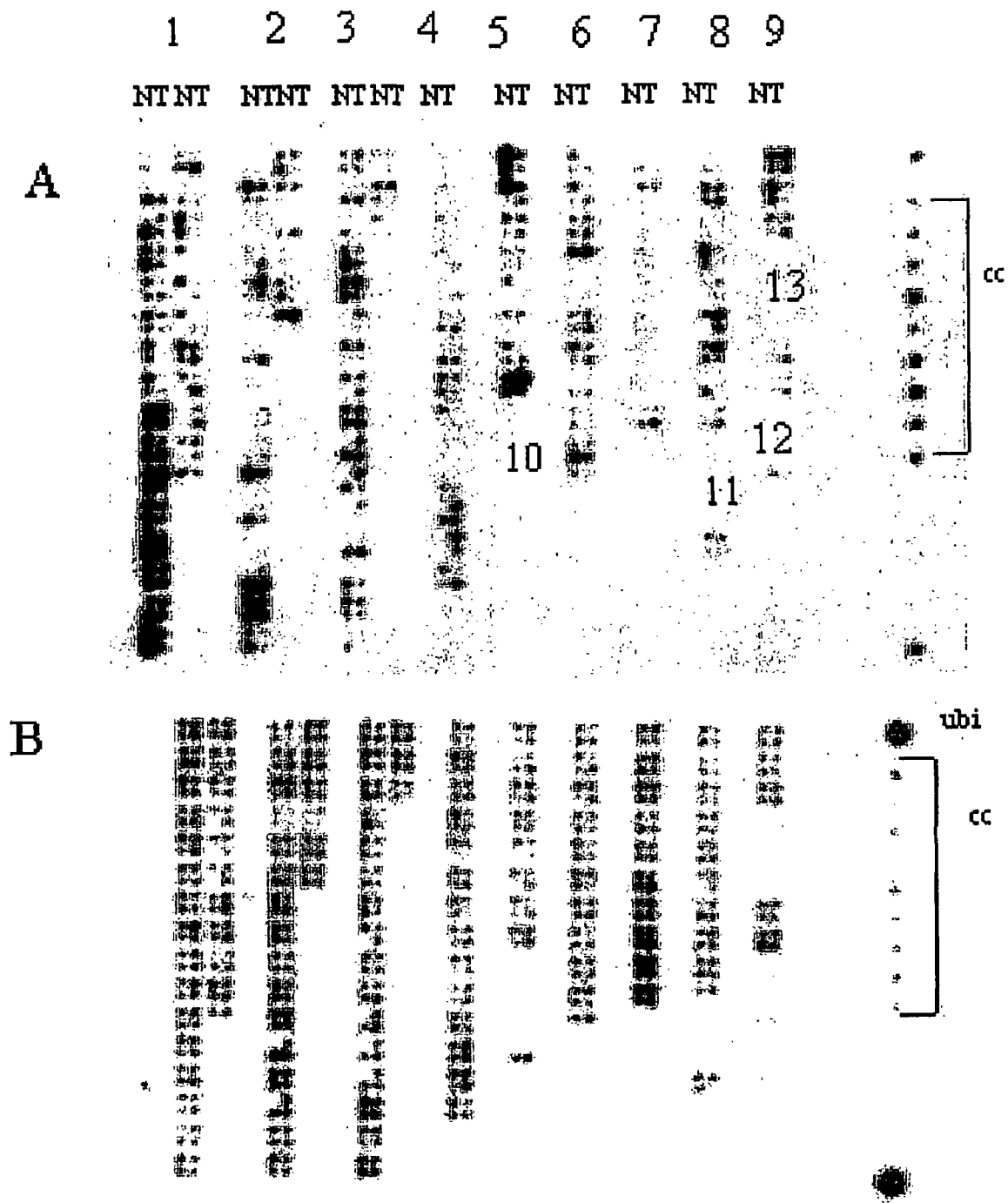

Membranes were hybridized with a $^{32}$P-labeled 441-bp fragment of RBP1L1 cDNA that was amplified by PCR from the immunopositive clone 151. Blots were washed twice in 0.1% standard saline citrate (SSC) and 0.1% SDS for 20 minutes and then exposed to Kodak BIOMAX film at −80° C. with an intensifying screen for 24 hours. As a loading control, blots were stripped and reprobed with the control ubiquitin cDNA (Clontech) to prove equal quantity of cDNA distribution in each pair of normal and cancer tissue. See Zhumabayeva and Adhikari (2001) "Cancer Profiling Array: A New Approach for Evaluating Differential Gene Expressions in Various Cancer Tissues" CLONTECHniques (Clontech), which is herein incorporated by reference. See FIG. 7B.

The cancer profiling array shows the tissue specific expression of RBP1L1. The cancer profiling array was hybridized separately with a radiolabeled RBP1L1 probe for RBP1L1, as shown in panel A, and a radiolabeled probe for the housekeeping gene ubiquitin, as shown in panel B. Numbers indicate tissue types in columns as follows: 1=breast, 2=uterus, 3=colon, 4=stomach, 5=ovary, 6=lung, 7=kidney, 8=rectum, 9=thyroid gland, 10=cervix, 11=small intestine, 12=pancreas, and 13=prostate. N=normal, T=tumor, Ubi=ubiquitin cDNA, cc=cancer cell line cDNAs.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

I claim:

1. A purified polypeptide consisting of SEQ ID NO:3.
2. A purified polypeptide consisting of SEQ ID NO:25.
3. A composition comprising the polypeptide of claim 1.
4. A composition comprising the polypeptide of claim 2.

* * * * *